United States Patent
Pearlman et al.

(10) Patent No.: US 9,334,508 B2
(45) Date of Patent: May 10, 2016

(54) METHODS OF PRODUCING CARBOXYLIC ACIDS

(75) Inventors: Paul S. Pearlman, Thornton, PA (US); Changlin Chen, Ingleby Barwick (GB); Adriana L. Botes, Rosedale East (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 13/525,034

(22) Filed: Jun. 15, 2012

(65) Prior Publication Data

US 2013/0224807 A1  Aug. 29, 2013

Related U.S. Application Data

(60) Provisional application No. 61/498,404, filed on Jun. 17, 2011, provisional application No. 61/558,718, filed on Nov. 11, 2011.

(51) Int. Cl.
C12P 7/44 (2006.01)
C02F 3/34 (2006.01)
C12N 9/18 (2006.01)
C12P 1/02 (2006.01)
C12P 7/40 (2006.01)
C12P 5/02 (2006.01)
(Continued)

(52) U.S. Cl.
CPC . *C12P 7/44* (2013.01); *C02F 3/342* (2013.01); *C12N 1/16* (2013.01); *C12N 9/18* (2013.01); *C12P 1/02* (2013.01); *C12P 5/02* (2013.01); *C12P 7/18* (2013.01); *C12P 7/40* (2013.01); *C12P 7/42* (2013.01); *C12P 7/46* (2013.01); *C12P 7/52* (2013.01); *C12P 13/001* (2013.01); *C12P 13/005* (2013.01); *C12P 17/10* (2013.01); *Y02P 20/52* (2015.11)

(58) Field of Classification Search
None
See application file for complete search history.

(56) References Cited

U.S. PATENT DOCUMENTS 2,439,513 A   4/1948   Hamblet et al.
2,557,282 A   6/1951   Hamblet et al.
(Continued)

FOREIGN PATENT DOCUMENTS

EP           2647718        10/2013
WO     WO 2008/006037       1/2008
(Continued)

OTHER PUBLICATIONS

Onakunle et al., The formation and substrate specificity of bacterial lactonases capable of enantioselective resolution of racemic lactones., Enzyme and Microbila Technology (1997), vol. 21, pp. 245-251.*

(Continued)

*Primary Examiner* — Alexander Kim
(74) *Attorney, Agent, or Firm* — William J. Simmons; Carla A. Mouta-Bellum

(57) ABSTRACT

The invention relates to methods for enriching monomer content in a cycloalkane oxidation process mixed organic waste stream. In particular, the methods involve combining a biocatalyst with a mixed organic waste stream from a cycloalkane oxidation process, and enzymatically converting dimeric and/or oligomeric components of said waste stream into monomeric components. The methods may enrich the content of diacids, adipic acid, and/or other α,ω-difunctional C6 alkanes in the mixed organic waste stream. Additionally, the treated mixed organic waste streams may have improved burning efficiency.

38 Claims, 21 Drawing Sheets

(51) Int. Cl.
*C12P 7/42* (2006.01)
*C12P 7/52* (2006.01)
*C12P 17/10* (2006.01)
*C12N 1/16* (2006.01)
*C12P 7/18* (2006.01)
*C12P 13/00* (2006.01)
*C12P 7/46* (2006.01)

(56) References Cited

U.S. PATENT DOCUMENTS

| | | |
|---|---|---|
| 2,791,566 A | 5/1957 | Jeffers |
| 2,840,607 A | 6/1958 | Attane, Jr. et al. |
| 2,971,010 A | 2/1961 | Gilby, Jr. et al. |
| 3,023,238 A | 2/1962 | Chapman et al. |
| 3,338,959 A | 8/1967 | Sciance et al. |
| 3,365,490 A | 1/1968 | Arthur et al. |
| 3,515,751 A | 6/1970 | Oberster |
| 3,719,561 A | 3/1973 | Tanaka et al. |
| 4,058,555 A | 11/1977 | Mims |
| 6,255,451 B1 | 7/2001 | Koch et al. |
| 6,372,939 B1 | 4/2002 | Bunnel et al. |
| 8,088,607 B2 | 1/2012 | Buggard et al. |
| 8,361,769 B1 | 1/2013 | Koch et al. |
| 2004/0054235 A1 | 3/2004 | Fodor et al. |
| 2010/0035309 A1 | 2/2010 | Havemen et al. |
| 2010/0151536 A1 | 6/2010 | Baynes et al. |
| 2010/0203600 A1 | 8/2010 | Dubois |
| 2010/0298612 A1 | 11/2010 | Behrouzian et al. |
| 2010/0317069 A1 | 12/2010 | Burk et al. |
| 2011/0171699 A1 | 7/2011 | Raemakers-Franken et al. |
| 2011/0256599 A1 | 10/2011 | Hu et al. |
| 2012/0064252 A1 | 3/2012 | Beatty |
| 2012/0101009 A1 | 4/2012 | Beatty |
| 2013/0065279 A1 | 3/2013 | Burk et al. |
| 2013/0183728 A1 | 7/2013 | Botes |
| 2013/0210090 A1 | 8/2013 | Pearlman et al. |
| 2013/0217081 A1 | 8/2013 | Pearlman et al. |
| 2013/0224807 A1 | 8/2013 | Pearlman et al. |
| 2013/0267012 A1 | 10/2013 | Steen et al. |
| 2014/0186902 A1 | 7/2014 | Botes et al. |
| 2014/0186904 A1 | 7/2014 | Botes et al. |
| 2014/0193861 A1 | 7/2014 | Botes et al. |
| 2014/0193862 A1 | 7/2014 | Botes et al. |
| 2014/0193863 A1 | 7/2014 | Botes et al. |
| 2014/0193864 A1 | 7/2014 | Botes et al. |
| 2014/0193865 A1 | 7/2014 | Botes et al. |
| 2014/0196904 A1 | 7/2014 | Fontenelle et al. |
| 2014/0199737 A1 | 7/2014 | Botes et al. |
| 2014/0248673 A1 | 9/2014 | Botes et al. |
| 2015/0111262 A1 | 4/2015 | Botes et al. |
| 2015/0267211 A1 | 9/2015 | Botes et al. |
| 2015/0320880 A1 | 11/2015 | Schleyer et al. |

FOREIGN PATENT DOCUMENTS

| | | |
|---|---|---|
| WO | WO 2008/145737 | 12/2008 |
| WO | WO 2009/121066 | 1/2009 |
| WO | WO 2009/113853 | 9/2009 |
| WO | WO 2009/113855 | 9/2009 |
| WO | WO 2009/140159 | 11/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/028519 | 2/2013 |
| WO | WO 2013/082542 | 6/2013 |
| WO | WO 2013/090837 | 6/2013 |
| WO | WO 2013/096898 | 6/2013 |
| WO | WO 2014/031724 | 2/2014 |
| WO | WO 2014/093865 | 6/2014 |
| WO | WO 2014/105788 | 7/2014 |
| WO | WO 2014/105793 | 7/2014 |

OTHER PUBLICATIONS

Ingale et al., Waste Treatment of an Aqueous Waste stream From a Cyclohexane Oxidation unit: A Case Study, Trans IChemE (1996), vol. 74, pp. 265-272.*
International Search Report and Written Opinion in International Application No. PCT/US2015/036074, mailed Sep. 9, 2015, 14 pages.
Invitation to Pay Fees in International Application No. PCT/US2015/036086, mailed Sep. 16, 2015, 7 pages.
Invitation to Pay Fees in International Application No. PCT/US2015/036092, mailed Sep. 21, 2015, 8 pages.
Uniprot Accession No. P69909, Sep. 1, 2005, 1 page.
"Enterococcus faecalis V583 bifuntional acetaldehyde-CoA/Alcohol Dehydrogenase," biocyc.org, retrieved on Jun. 19, 2014, http://biocyc.org/EFAE226185/N EW-IMAGE?type=ENZYME &object=GH11-877-MONOMER, 9 pages.
"Information on EC 1.2.1.57—butanal dehydrogenase," brenda-enzymes.org, retrieved on Jun. 19, 2014, http://www.brenda-enzymes.org/php/result_flat.php4?ecno=1.2.1.57, 6 pages.
"BRENDA—The comprehensive Enzyme Information System," Jul. 2011, retrieved on Sep. 19, 2014, http://web.archive.org/web/20111009205602/http://www.brenda-enzymes.org/, 1 page.
Alber et al., "Malonyl-coenzyme A reductase in the modified 3-hydroxypropionate cycle for autotrophic carbon fixation in archaeal *Metallosphaera* and *Sulfolobus* spp," J. Bacteriology, 2006, 188:8551-8559.
Anton et al., Polyamides, Fibers, Encyclopedia of Polymer Science and Engineering, 2001, 11:409-445.
Azuma et al., "Naphthalene—a constituent of Magnolia flowers," Phytochemistry, 1996, 42:999-1004.
Barker et al., "Enzymatic reactions in the degradation of 5-aminovalerate by Clostridium aminovalercum," J Biol Chem., 1987, 262(19):8994-9003.
Becker et al., "Metabolic flux engineering of L-lysine production in Corynebacterium glutamicum—over expression and modification of G6P dehydrogenase," J Biotechnol. 2007, 132(2):99-109.
Bellmann et al., "Expression control and specificity of the basic amino acid exporter LysE of Corynebacterium glutamicum," Microbiology 2001, 147:1765-1774.
Bennett et al., "Purification and properties of ε-caprolactone hydrolases from Acinetobacter NCIB 9871 and Nocardia globevula CL1," Journal of General Microbiology, 1988 134: 161-168.
Bernstein et al., "Transfer of the high-GC cyclohexane caboxylate degradation pathway from Rhodopseudomonas palustris to *Escherichia coli* for production of biotin," Metobolic Engineering, May 2008, 10(3-4):131-140.
Berthold et al., "Structure of the branched-chain keto acid decarboxylase (KdcA) from Lactococcus lactis provides insights into the structural basis for the chemoselective and enantioselective carboligation reaction," Acta Crystallographica Sec. D, 2007, D63:1217-1224.
Binieda et al., "Purification, characterization, DNA Sequence and cloning of a pimeloyl-CoA synthetase from Pseudomonas medocin 35," Biochem J., 1999, 340:793-801.
Bond-Watts et al., "Biochemical and Structural Characterization of the trans-Enoly-CoA Reductase from Treponema denticola," Biochemistry, 2012, 51:6827-6837.

(56) References Cited

OTHER PUBLICATIONS

Bordes et al., "Isolation of a thermostable variant of Lip2 lipase from Yarrowia lipolytica by directed evolution and deeper insight into the denaturation mechanisms," Journal of Biotechnology, 2011, 156: 117-124.
Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.
Boylan et al., "Functional identification of the fatty acid reductase components encoded in the luminescence operon of Vibrio fischeri," Journal of Bacteriology, 1985, 163(3):1186-1190.
Boylan et al., "Lux C, D and E genes of the Vibrio fischeri luminescence operon code for the reductase, transferase, and synthetase enzymes involved in aldehyde biosynthesis," Photochemistry and photobiology, 1989, 49:681-688.
Bramer et al., "The methylcitric acid pathway in Ralstonia eutropha: new genes identified involved in propionate metabolism," Microbiology 2001, 147:2203-2214.
Breithaupt et al., "Crystal structure of 12-oxophytodienoate reductase 3 from tomato: self-inhibition by dimerization," Proc Natl. Acad Sci. USA, 2006, 103:14337-14342.
Brigham et al., "Engineering Ralstonia eutropha for Production of Isobutanol from CO2, H2, and O2," Advanced Biofuels and Bioproducts 2013, Chapter 39, pp. 1065-1090.
Brzostowicz et al., "mRNA differential display in a microbial enrichment culture: simultaneous identification of three cyclohexanonemonooxygenases from three species," Applied and Environmental Microbiology, 2003, 69: 334-342.
Brzostowicz et al., "Identification of two gene clusters involved in cyclohexanone oxidation in Brevibacterium epidermidis strain HCU," Applied and Microbiological Biotechnology, 2002, 58:781-789.
Buckel et al., "Glutaconate CoA-transferase from Acidaminococcus fermentans," Eur J. Biochem, 1981, 118:315-321.
Budde et al., "Roles of Multiple Acetoacetyl Coenzyme A Reductases in Polyhydroxybutyrate Biosynthesis in Ralstonis eutropha H16," J Bacteriol. 2010, 192(20):5319-5328.
Bugg et al., "The emerging role for bacteria in lignin degradation and bio-product formation," Curr Opin Biotechnol 2011, 22(3):394-400.
Buhler et al., "Occurrence and the possible physiological role of 2-enoate reductases," FEBS Letters, 1980, 109:244-246.
Bult et al., "Complete genome sequence of the methanogenicarchaeon, Methanococcus jannaschii," Science, 1996, 273: 1058-1073.
Bunik et al., "Kinetic properties of the 2-oxoglutarate dehydrogenase complex from Azotobacter vinelandii evidence for the formation of a precatalytic complex with 2-oxoglutarate," Eur J Biochem., 267(12):3583-3591, Jun. 2000.
Cantu et al., "Thioesterases: A new perspective based on their primary and tertiary structures," Protein Science 2010, 19:1281-1295.
Chayabutra and Ju, "Degradation of n-hexadecane and its metabolites by Pseudomonas aeruginosa under microaerobic and anaerobic denitrifying conditions," Appl Environ Microbiol., 66(2):493-498, Feb. 2000.
Cheesbrough and Kolattukudy, "Alkane biosynthesis by decarbonylation of aldehydes catalyzed by a particulate preparation from Pisum sativum," PNAS USA, 1984, 81(21):6613-7.
Chen et al., "Termites fumigate their nests with naphthalene," Nature, 1998, 392:558-559.
Cheng et al., "Genetic Analysis of a Gene Cluster for Cyclohexanol Oxidation in *Acinetobacter* sp. Strain SE19 by In Vitro Transposition," Journal of Bacteriology, 2000, 182(17):4744-4751.
Coon, "Omega oxygenases: nonheme-iron enzymes and P450 cytochromes," Biochemical & Biophysical Research Communications, 2005,338:378-385.
Cronan and Lin, "Synthesis of the α,ω-dicarboxylic acid precursor of biotin by the canonical fatty acid biosynthetic pathway," Current Opinion in Chem Biol., 2011, 15:407-413.

Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.
Cryle et al., "Carbon-carbon bond cleavage by cytochrome P450BioI (CYP107H1) EI," Chemical Communications, Jan. 2004, 86-87.
Cryle, "Selectivity in a barren landscape: the P450BioI-ACP complex," Biochemical Society Transactions, Aug. 2010, 38(4):934-939.
Da Silva et al., "Glycerol: A promising and abundant carbon source for industrial microbiology," Biotechnology Advances, 2009, 27:30-39.
Daisy et al., "Naphthalene, an insect repellent, is produced by Muscodor vitigenus, a novel endophytic fungus," Microbiology, 2002, 148:3737-3741.
Dalby, "Optimizing enzyme function by directed evolution," Current Opinion in Structural Biology, 2003, 13, 500-505.
Davis et al., "Overproduction of acetyl-CoA carboxylase activity increases the rate of fatty acid biosynthesis in *Escherichia coli*," J. Biol. Chem., 2000, 275(37): 28593-28598.
Day et al., "Partial purificaton and properties of acyl-CoA reductase from *Clostridum butyricum*," Archives of Biochemistry and Biophysics, 1978, 190(1):322-331.
Deana et al., "Substrate specificity of a dicarboxyl-CoA: Dicarboxylic acid coenzyme . A transferase from rat liver mitochondria," Biochem Int., 1992, 26:767-773.
Dekishima et al., "Extending Carbon Chain Length of 1-Butanol Pathway for 1-Hexanol Synthesis from Glucose by Engineered *Escherichia coli*," J. Am. Chem. Soc., Aug. 2011, 133(30):11399-11401.
Dellomonaco et al., "Engineered reversal of the [beta]-oxidation cycle for the synthesis of fuels and chemicals," Nature, Jan. 2011, 476(7360):355-359.
Deshmukh and Mungre, "Purification and properties of 2-aminoadipate: 2-oxoglutarate aminotransferase from bovine kidney," Biochem J, 1989, 261(3):761-768.
Doan et al., "Functional expression of five Arabidopsis fatty acyl-CoA reductase genes in *Escherichia coli*," J. Plant Physiology, 2009, 166:787-796.
Dobritzsch et al., "High resolution crystal structure of pyruvate decarboxylase from Zymomonas mobilis. Implications for substrate activation in pyruvate decarboxylases," J. Biol. Chem., 1998, 273:20196-20204.
Donoghue and Trudgill, "The Metabolism of Cyclohexanol by Acinetobacter NCIB9871," Eur J Bochem., 1975, 60:1-7.
Drevland et al., "Enzymology and Evolution of the Pyruvate Pathway to 2-Oxobutyrate in Methanocaldococcus jannaschii," J. Bacteriol., Apr. 2007, 189(12):4391-4400.
Drevland et al., "Methanogen homoaconitase catalyzes both hydrolyase reactions in coenzyme B biosynthesis," J Biol Chem., Oct. 2008, 283: 28888-28896.
Egmond et al., "Fusarium solani pisi cutinase," Biochimie, Nov. 2000, 82(11):1015-1021.
Elkins et al., "Substrate Specificity of the RND-Type Multidrug Efflux Pumps AcrB and AcrD of *Esherichia coli* Is Determined Predominately by Two Large Periplasmic Looops," J Bacteriol. 2002, 184(23):6490-6499.
Elshahed et al., "Benzoate Fermentation by the Anaerobic bacterium Syntrophus aciditrophicus in the Absence of Hydrogen-Using Microorganisms," Applied and Environ Microbiology, 2001, 67(12):5520-5525.
Elshahed et al., "Metabolism of Benzoate, Cyclohex-1-ene Carboxylate, and Cyclohexane Carboxylate by Syntrophus aciditrophicus Strain SB in Syntrophic Association with H2-Using Microorganisms," Applied and Environ. Microbiol., Apr. 2001, 67(4):1728-1738.
Eurich et al., "Cloning and characterization of three fatty alcohol oxidase genes from Candida tropicalis strain ATCC 20336," Applied & Environmental Microbiology, 2004, 70(8): 4872-4879.
Ferreira et al. "A member of the sugar transporter family, Stl1p is the glycerol/H= symporter in *Saccharomyces cerevisiae*," Molecular Biology of the Cell, American Society for Cell Biology, Apr. 1, 2005, 16(4):2068-2076.

(56) References Cited

OTHER PUBLICATIONS

Fickers et al., "Carbon and nitrogen sources modulate lipase production in the yeast Yarrowia lipolytica," Journal of Applied Microbiology, 2004, 96:742-9.
Fickers et al., "The lipases from Yarrowia lipolytica: Genetics, production, regulation, biochemical characterization and biotechnological applications," Biotechnology Advances, 2011, 29: 632-644.
Fuchs et al., "Microbial degradation of aromatic compounds—from one strategy to four," Nat Rev Microbiol., Oct. 3, 2011;9(11):803-816, Oct. 2011.
Fukui et al., "Expression and Characterization of ®-Specific Enoly Coenzyme A Hydratase Involved in Polyhydroxyalkanoate Biosynthesis by Aeromonas caviae," J Bacteriol. 1998, 180(3):667-673.
Funhoff et al., "CYP153A6, a Soluble P450 Oxygenase Catalyzing Terminal-Alkane Hydroxylation," J Bacteriol. 2006, 188(14):5220-5227.
Funhoff et al., "Expression and Characterization of (R)-Specific Enoyl Coenzyme A Hydratase Involved in Polyhydroxyalkanoate Biosynthesis by Aeromonas caviae," J. Bacteriol., 2006, 188(14):5220-5227.
Gallus and Schink, "Anaerobic degradation of pimelate by newly isolated denitrifying bacteria," Microbiology, 1994, 140:409-416.
Gasmi et al., "A molecular approach to optimize hIFN α2b expression and secretion in Yarrowia lipolytica," Appl Microbiol Biotechnol, 2011, 89:109-119.
GenBank Accession No. AAA24664.1, Mar. 25, 1993, 1 page.
GenBank Accession No. AAA24665.1, Apr. 26, 1993, 1 page.
GenBank Accession No. AAA57874.1, Nov. 21, 2011, 2 pages.
GenBank Accession No. AAA69178.1, Jul. 1, 1995, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct. 23, 2009, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
GenBank Accession No. AAF02538.1, Oct. 20, 1999, 2 pages.
GenBank Accession No. AAG08191.1, Jan. 31, 2014, 2 pages.
GenBank Accession No. AAK73167.2, retrieved May 19, 2014, 1 page.
GenBank Accession No. AAN37290.1, retrieved May 19, 2014, 1 page.
GenBank Accession No. AAO77182, Mar. 28, 2003, 1 page.
GenBank Accession No. AAQ59697.1, Jan. 31, 2014, 2 pages.
GenBank Accession No. AAS11092.1, Mar. 5, 2010, 1 page.
GenBank Accession No. AAS43086.1, dated Nov. 2011, 1 page.
GenBank Accession No. AAT43726, retrieved May 19, 2014, 1 page.
GenBank Accession No. AAW66853.1, Feb. 12, 2005, 1 page.
GenBank Accession No. AAY39893.1, Jan. 31, 2014, 2 pages.
GenBank Accession No. AB005294, Feb. 2000, 2 pages.
GenBank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
GenBank Accession No. ABE47158.1, Jan. 26, 2014, 1 page.
GenBank Accession No. ABE47159.1, Jan. 28, 2014, 2 pages.
GenBank Accession No. ABE47160.1, Jan. 28, 2014, 1 page.
GenBank Accession No. ABI83656.1, Jan. 3, 2007, 1 page.
GenBank Accession No. ABJ63754.1, dated Mar. 2010, 1 page.
GenBank Accession No. ABK71854.1, Jan. 31, 2014, 2 pages.
GenBank Accession No. ABK75684.1, Jan. 31, 2014, 2 pages.
GenBank Accession No. ACC40567.1, Jan. 31, 2014, 2 pages.
GenBank Accession No. ACJ06772.1, Dec. 4, 2009, 1 page.
GenBank Accession No. ADG98140.1, Jan. 28, 2014, 2 pages.
GenBank Accession No. ADK19581.1, Sep. 20, 2010, 2 pages.
GenBank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
GenBank Accession No. BAB91331.1, retrieved May 19, 2014, 1 page.
GenBank Accession No. BAC06606, Aug. 1, 2002, 1 page.
GenBank Accession No. BAD69624, Sep. 2005, 1 page.
GenBank Accession No. BAF92773, Nov. 27, 2007, 1 page.
GenBank Accession No. BAF94304.1, retrieved May 19, 2014, 1 page.
GenBank Accession No. CAA44858.1, Apr. 28, 1992, 1 page.
GenBank Accession No. CAA81612.1, Apr. 18, 2005, 2 pages.
GenBank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 page.
GenBank Accession No. CAE26094.1, Apr. 17, 2005, 2 pages.
GenBank Accession No. CAE26097.1, Apr. 17, 2005, 2 pages.
GenBank Accession No. CAH04396.1, Apr. 7, 2005, 1 page.
GenBank Accession No. CAH04397.1, Apr. 7, 2005, 2 pages.
GenBank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. EFV11917.1, Sep. 9, 2013, 2 pages.
GenBank Accession No. EIV11143.1, Jun. 19, 2012, 2 pages.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. NM_001246944, Dec. 2011, 2 pages.
GenBank Accession No. NM_001247852, Dec. 2011, 2 pages.
GenBank Accession No. NM_133240, Feb. 25, 2002, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus sphaericus* genes controlling the bioconversion of pimlate into dethiobiotin," Gene, 1990, 87:63-70.
Gloerich et al., "Peroxisomal trans-2-enoyl-CoA reductase is involed in phytol degradation," FEBS Letters 2006, 580:2092-2096.
Gocke et al., "Comparative characterisation of ThPP-dependent decarboxylases," J. Mol. Cat. B: Enzymatic, 2009, 61:30-35.
Gonzalez-Lopez, "Genetic control of extracellular protease synthesis in the yeast Yarrowia lipolytica," Genetics, 2002, 160: 417-427.
Graupner et al., "Identification of the gene encoding sulfopyruvate decarboxylase, an enzyme involved in biosynthesis of coenzyme M," J Bacterial., 2000, 182: 4862-4867.
Guerrillot et al., "Purification and Characterization of Two Aldehyde Dehydrogenases from Pseudomonas aeruginosa," Eur. J. Biochem. 1977, 81:185-192.
Hall, "The Contribution of Horizontal Gene Transfer to the Evolution of Fugi," Duke University Libraries, May 10, 2007, 163 pages.
Hall, "Asymmetric bioreduction of activated alkenes using cloned 12-oxophytodienoate reductase isoenzymes OPR-1 and OPR-3 from

(56) References Cited

OTHER PUBLICATIONS

Lycopersicon esculentum (tomato): a striking change of stereoselectivity," Agnew Chem Int. Ed., 2007, 46:3934-3937.
Han et al., "Oxaloacetate hydrolase, the C-C bond lyase of oxalate secreting fungi," J. Biol. Chem. 2007, 282:9581-9590.
Harrison and Harwood, "The pimFABCDE operon from Phodopseudomonas palustris mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism Alcaligenes eutrophus," FEMS Microbiology Letters 1988, 52(1-2):91-96.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from Bacillus subtilis," J Biol Chem., 275(51):40128-40133, Dec. 22, 2000.
Hermann et al, "Industrial production of amino acids by coryneform bacteria," J Biotechnol. 2003, 104(1-3):155-172.
Hess et al., "Extremely thermostable esterases from the thermoacidophilic euryarchaeon Picrophilus torridus," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from Euglena gracilis defines a new family of enzymes involved in lipid synthesis," J Biol Chem., 280(6):4329-4338. Epub Nov. 29, 2004.
Hofvander et al., "A prokaryotic acyl-CoA reductase performing reductiojn of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of Arabidopsis," Plant J., 1999, 20:1-13.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenicArchaea," Biochemistry, 1989, 37: 10108-10117.
Howell et al., "Identification of enzymes homologous to isocitrate dehydrogenase that are involved in coenzyme Band leucine biosynthesis in methanoarchaea," J Bacteriol., Sep. 2000, 182: 5013-5016.
Hugler et al., "Malonyl-coenzyme a reductase from Chloroflexus aurantiacus, a key enzyme of the 3-hydroxypropionate cycle for autotrophic CO(2) fixation," J. Bacteriology, 2002, 184:2404-2410.
Huhn et al., "Identification of the membrane protein SucE and its role in succinate transport in Corynebacterium glutamicum," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.

International Preliminary Report on Patentability for International Application No. PCT/US 2012/069934, mailed Jun. 17, 2014, 15 pages.
International Preliminary Report on Patentability in International Application No. PCT/US 2012/042777, mailed Jan. 10, 2013, 22 pages.
International Preliminary Report on Patentability in International Application No. PCT/US 2012/044984, mailed Jan. 28, 2014, 11 pages.
International Search Report and Written Opinion for International Application No. PCT/US 2012/069934, mailed Jan. 17, 2014, 21 pages.
International Search Report and Written Opinion in International Application No. PCT/US 2012/042747, mailed Jan. 14, 2013, 19 pages.
International Search Report and Written Opinion in International Application No. PCT/US 2012/042777, mailed Sep. 11, 2012, 9 pages.
International Search Report and Written Opinion in International Application No. PCT/US 2012/044984, mailed Dec. 17, 2013, 17 pages.
International Search Report and Written Opinion in International Application No. PCT/US 2012/071472, mailed Dec. 17, 2013, 17 pages.
International Search Report and Written Opinion in International Application No. PCT/US2013/075058, mailed Sep. 15, 2014, 17 pages.
International Search Report and Written Opinion in International Application No. PCT/US2013/075087, mailed Aug. 4, 2014, 18 pages.
International Search Report and Written Opinion in International Application No. PCT/US2013/077413, mailed Jul. 22, 2014, 20 pages.
International Search Report and Written Opinion in International Application No. PCT/US2013/077419, mailed Jun. 16, 2014, 19 pages.
International Search Report and Written Opinion in International Application No. PCT/US2013/077420, mailed Jul. 21, 2014, 21 pages.
International Search Report and Written Opinion in International Application No. PCT/US2013/077423, mailed Jul. 21, 2014, 22 pages.
International Search Report and Written Opinion in International Application No. PCT/US2013/077445, mailed Sep. 15, 2014, 17 pages.
Invitation to Pay Additional Fees in International Application No. PCT/US2013/075058, mailed Jul. 7, 2014, 7 pages.
Invitation to Pay Additional Fees in International Application No. PCT/US2013/07745, mailed Jul. 7, 2014, 9 pages.
Invitation to Pay Fees in International Application No. PCT/US2013/075087, mailed May 16, 2014, 9 pages.
Invitation to Pay Fees in International Application No. PCT/US2013/077411, mailed Jul. 16, 2014, 9 pages.
Invitation to Pay Fees in International Application No. PCT/US2013/077413, mailed May 12, 2014, 9 pages.
Invitation to Pay Fees in International Application No. PCT/US2013/077419, mailed Apr. 16, 2014, 9 pages.
Invitation to Pay Fees in International Application No. PCT/US2013/077420, mailed May 13, 2014, 9 pages.
Invitation to Pay Fees in International Application No. PCT/US2013/077423, mailed May 13, 2014, 10 pages.
Invitation to Pay Fees in International Application No. PCT/US2013/077430, mailed Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbilogy, 2002, 68:1192-1195.
Ishikawa et al., "The pathway via D-galacturonate/L-galactonate is significant for ascorbate biosynthesis in Euglena gracilis: identification and functional characterization of aldonolactonase," Journal of Biologiocal Chemistry, 2008, 283:31133-31141.
Iwaki et al., "Cloning and Characterization of a Gene Cluster Involved in Cyclopentanol Metabolism in Comamonas sp. Strain

(56) References Cited

OTHER PUBLICATIONS

NCIMB 9872 and Biotransformations Effected by *Escherichia coli*-Expressed Cyclopentanone 1,2-Monooxygenase," Appl Environ Microbiol., 2002, 68(11):5671-5684, 14 pages.

Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.

Izumi et al., "Structure and Mechanism of HpcG, a Hydratase in the Homoprotocatechuate Degradation Pathway of *Escherichia coli*," J. Mol. Biol., 2007, 370:899-911.

Izumi et al., "The pimeloyl-CoA synthetase responsible for the first step in biotin biosynthesis by microorganisms," Agr. Biol. Chem., 1974, 38:2257-2262.

Jacob et al., "Gluconate CoA-transferase from *Acidamiococcus fermentans*: the crystal structure reveals homology with other CoA-transferases," Structure, 1997, 5:415-426.

Jang et al., "Bio-based production of C2-C6 platform chemicals," Biotechnol. & Bioengineering, 2012, 109(10):2437-2459.

Jarboe, "YqhD: a broad-substrate range aldehyde reductase with various applications in production of biorenewable fuels and chemicals," Appl Microbiol Biotechnol., 2011, 89(2):249-257.

Jaremko et al., "The initial metabolic conversion of levulinic acid in *Cupriavidus necator*," J. Biotechnol., 2011, 155(3):293-298.

Jeyakanthan et al., "Substrate specificity determinants of the methanogen homoaconitase enzyme: structure and function of the small subunit," Biochemistry, 2010, 49:2687-2696.

Jing et al., "Phylogenetic and experimental characterization of an acyl-ACP thioesterase family reveals significant diversity in enzymatic specificity and activity," BMC Biochemistry, 2011, 12:44, 16 pages.

Joon-Young et al., "Production of 1,2-Propanediol from Glycerol in *Saccharomyces cerevisiae*," J. Microbiology and Biotechnology, May 19, 2011, 21(8):846-853.

Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.

Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.

Kaulmann et al., "Substrate spectrum of omega-transaminase from *Chromobacterium violaceum* DSM30191 and its potential for biocatalysis," Enzyme Microb Technol. 2007, 41:628-637.

Kikuchi et al., "Characterization of a second lysine decarboxylase isolated from *Escherichia coli*," J Bacteriol, 1997, 179(14): 4486-4489.

Kim et al., "Cloning and characterization of a cyclohexanone monooxygenase gene from *Arthrobacter* sp. L661," Biotechnology Bioprocess Engineering, 2008, 13:40-47.

Kim, "Purification and properties of a diamine alpha-ketoglutarate transaminase from *Escherichia coli*," J Biol Chem 1964, 239(3):783-786.

Kitzing et al., "The 1.3 A crystal structure of the flavoprotein YqjM reveals a novel class of Old Yellow Enzymes," J. Biol. Chem., 2005, 280:27904-27913.

Koch et al., "Products of Enzymatic Reduction of Benzoyl-CoA, A Key Reaction in Anaerobic Aromatic Metabolism," Eur. J. Biochemistry, Jan. 1993, 211(3):649-661.

Koch et al., "In Vivo Evolution of Butane Oxidation by Terminal Alkane Hydroxylases AlkB and CYP153A6," Appl. Environ. Microbiol., 2009, 75(2):337-344.

Kockelkorn and Fuchs, "Malonic semialdehyde reductase, succinic semialdehyde reductase, and succinyl-coenzyme A reductase from Metallosphaera sedula: enzymes of the autotrophic 3-hydroxypropionate/4-hydroxybutyrate cycle in Sulfolobales," J. Bacteriology, 2009, 191:6352-6362.

Kolattukudy, "Enzymatic synthesis of fatty alcohols in *Brassica oleracea*," Archives of Biochemistry and Biophysics, 1971, 142(2):701-709.

Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.

Kulkarni and Kanekar, "Bioremediation of epsilon-caprolactam from nylon-6 waste water by use of Pseudomonas aeruginosa MCM B-407," Curr. Microbiol., 1998, 37:191-194.

Kung et al., "Cyclohexanecarboxyl-coenzyme A (CoA) and cyclohex-1-ene-1-carboxyl-CoA dehydrogenases, two enzymes involved in the fermentation of benzoate and crotonate in Syntrophus aciditrophicus," J Bacteriol., 195(14):3193-3200, Epub May 10, 2013.

Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.

Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.

Le Dall et al., "Multiple-copy integration in the yeast Yarrowia lipolytica," Current Genetics, 1994 26:38-44.

Lee and Meighen, "Cysteine-286 as the site of acylation of the LUX-specific fatty acyl-CoA reductase," Biochim Biophys Acta, 1997, 1338:215-222.

Lee et al., "Metabolic Engineering of Pentose Phosphate Pathway in Ralstonia eutropha for Enhanced Biosynthesis of Poly-β-hydroxybutyrate," Biotechnology Progress, 2003, 19(5):1444-1449.

Lee et al., "Synthesis of pure meso-2,3-butanediol from crude glycerol using an engineered metabolic pathway in *Escherichia coli*," Appl Biochem Biotechnol., 2012, 166(7):1801-1813.

Li et al., "Cupriavidus necator JMP 134 rapidly reduces furfural through a Zn-dependent alcohol dehydrogenase," Biodegradation, 2011, 22:1215-1225.

Lim et al., "Amplification of the NADPH-related genes zwf and gnd for the oddball biosynthesis of PHB in an *E. coli* transformant harboring a cloned phbCAB operon," J Bioscience and Bioengineering, 2002, 93(6):543-549.

Lin and Cronan, "Closing in on complete pathways of biotin biosynthesis," Molecular Biosystems, 2011, 7:1811-1821.

Lin et al., "Biotin Sythesis Begins by Hijacking the Fatty Acid Synthetic Pathway," Nature Chem Biol., Sep. 2010, 6:682-688.

Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.

Lin, "Biotin Synthesis in *Escherichia coli*," PhD Dissertation, University of Illinois at Urbana-Champaign, 2012, 140 pages.

Liu and Chen, "Production and characterization of medium-chain-length polyhydroxyalkanoate with high 3-hydroxytetradecanoate monomer content by fadB and fadA knockout mutant of Pseudomonas putida KT2442," Appl. Microbiol. Biotechnol., 2007, 76(5):1153-1159.

Liu et al., "Two novel metal-independent long-chain alkyl alcohol dehydrogenases from Geobacillus thermodenitrificans NG80-2," Microbiology, 2009, 155:2078-2085.

Lopez-Sanchez et al., "Tetralin-Induced and ThnR-Regulated Aldehyde Dehydrogenase and β-Oxidation Genes in Sphingomonas macrogolitabida Strain TFA," Appl. Environ. Microbiol., 2010, 76(1):110-118.

Luo et al., "Production of 3-hydroxypropionic acid through propionaldehyde dehydrogenase PduP mediated biosynthetic pathway in Klebsiella pneumoniae," Bioresource Technology, 2012, 103:1-6.

Lütke-Eversloh & Steinbüchel, "Biochemical and molecular characterization of a succinate semialdehyde dehydrogenase involved in the catabolism of 4-hydroxybutyric acid in Ralstonia eutropha," FEMS Microbiology Letters, 1999, 181(1):63-71.

Mack and Buckel, "Conversion of glutaconate CoA-transferase from Acidaminococcus fermentans into an acyl-CoA hydrolase by site-directed mutagenesis," FEBS Letters, 1997, 405:209-212.

(56) References Cited

OTHER PUBLICATIONS

Maeda et al., "Purification and characterisation of a biodegradable plastic-degrading enzyme from Aspergillus oryzae," Applied and Environmental Biotechnology, 2005, 67: 778-788.
Mahadik et al., "Production of acidic lipase by Aspergillus niger in solid state fermentation," Process Biochemistry, 2002, 38: 715-721.
Martin and Prather, "High-titer production of monomeric hydroxyvalerates from levulinic acide Pseudomonas putida," J. Biotechnol., 2009, 139: 61-67.
Martinez et al., "Fusarium solani cutinase is a lipolytic enzyme with a catalytic serine accessible to solvent," Nature, 1992, 356:615-618.
Matsumoto et al., "A new pathway for poly(3-hydroxybutyrate) production in *Escherichia coli* and Corynebacterium glutamicum by functional expression of a new acetoacetyl-coenzyme A synthase," Biosci. Biotechnol. Biochem., 2011, 75(2):364-366.
Mawal and Deshmukh, "Alpha-aminoadipate and kynurenine aminotransferase activities from rat kidney. Evidence for separate identity," J. Biol Chem, 1991, 266(4):2573-2575.
McAndrew et al., "Structural basis for substrate fatty acyl chain specificity: crystal structure of human very-long-chain acyl-CoA dehydrogenase," J. Biol. Chem., 2008, 283:9435-9443.
Meijnen et al., "Improved p-hydroxybenzoate production by engineered Pseudomonas putida S12 by using a mixed-substrate feeding strategy," Appl. Microbiol. Biotechnol., 2011, 90:885-893.
Mhetras et al., "Purification and characterization of acidic lipase from Aspergillus niger NCIM 1207," Bioresource Technology, 2009, 100: 1486-1490.
Millar et al., "CUT1, an Arabidopsis Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.
Miyazaki et al., "Alpha-Aminoadipate aminotransferase from an extremely thermophilic bacterium, Thermus thermophilus," Microbiology, 2004, 150(7): 2327-2334.
Mo et al., "Connecting extracellular metabolomic measurements to intracellular flux states in yeast," BMC Systems Biology, 2009, 3(37):1-17.
Mouttaki et al., "Cyclohexane Carboxylate and Benzoate Formation from Crotonate in Sytrophus aciditrophicus," Applied and Environ Microbiology, Feb. 2007, 73(3):930-938.
Murphy et al., "Fusarium polycaprolactone depolymerase is cutinase," Appl. Environm. Microbiol., 1996, 62:456-460.
Naggert et al., "Cloning, sequencing, and characterization of *Escherichia coli* thioesterase II," J. Biol. Chem., 1991, 266(17):11044-11050.
Neyfakh, "The Multidrug Efflux Transporter of Bacillus subtilis is a Structural and Functional Homolog of the *Staphylococcus* NorA Protein," Antimicrob Agents Chemother, 1992, 36(2):484-485.
Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.
Nicol et al., "Bioconversion of crude glycerol by fungi," Applied Microbiology and Biotechnology, Feb. 10, 2012, 93(5):1865-1875.
Nieder and Shapiro, "Physiological function of the Pseudomonas putida PpG6 (Pseudomonas oleovorans) alkane hydroxylase: monoterminal oxidation of alkanes and fatty acids," J. Bacteriol., 1975, 122(1):93-98.
Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.
Ohashi et al., "Continuous production of lactic acid from molasses by perfusion culture of Lactococcus lactis using a stirred ceramic membrane reactor," J. Bioscience and Bioengineering, 1999, 87(5):647-654.
Okuhara et al., "Formation of Glutaric and Adipic Acids from n-Alkanes with Odd and Even Numbers of Carbons by Candida tropicalis OH23," Agr. Biol. Chem., 1971, 35(9):1376-1380.
Onakunle et al., "The formation and substrate specificity of bacterial lactonases capable of enantioselective resolution of racemic lactones," Enzyme and Microbial Technology, 1997, 21: 245-251.
Oppenheim and Dickerson, "Adipic Acid," Kirk-Othmer Encyclopedia of Chemical Technology, 2003.
Ouchi et al., "Dual roles of a conserved pair, Arg23 and Ser20, in recognition of multiple substrates in alpha-aminoadipate aminotransferase from Thermus thermophilus," Biochem Biophys Res Commun, 2009, 388(1):21-27.
Palosaari and Rogers, "Purification and properties of the inducible coenzyme A-linked butyraldehyde dehydrogenase from Clostridium acetobutylicum," J. Bacteriol., 1988, 170(7):2971-2976.
Papanikolaou et al., "Citric acid production by Yarrowia lipolytica cultivated on olive-mill wastewater-based media," Bioresource Technol., 2008, 99(7):2419-2428.
Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.
Pelletier and Harwood et al., "2-Hydroxycyclohexanecarboxyl coenzyme A dehydrogenase, an enzyme characteristic of the anaerobic benzoate degradation pathway used by Rhodopseudomonas palustris," J Bacteriol., 182(10):2753-2760, May 2000.
Pérez-Pantoja et al., "Metabolic reconstruction of aromatic compounds degradation from the genome of the amazing pollutant-degrading bacterium Cupriavidus necator JMP134," FEMS Microbiol. Rev., 2008, 32:736-794.
Peterson et al., "The Thermal Stability of the Fusarium solani pisi Cutinase as a Function of pH," BioMed Research International, 2001, 1.2:62-69.
Pignede et al., "Autocloning and Amplification of LIP2 in Yarrowia lipolytica," Appl. Environ. Microbiol, 2000 66:3283-3289.
Pignede et al., "Characterization of an extracellular lipase encoded by LIP2 in Yarrowia lipolytica," Journal of Bacteriology, 2000, 182: 2802-2810.
Ploux et al., "Investigation of the first step of biotin biosynthsis in Bacillus sphaericus: Purification and characterization of the pimloyl-CoA sythase, and uptake of pimelate," Biochem J., 1992, 287:685-690.
Prybylski et al., "Third-generation feed stocks for the clean and sustainable biotechnological production of bulk chemicals: synthesis of 2-hydroxyisobutyric acid," Energy, Sustainability and Society, 2012, 2:11.
Qian et al., "Metabolic engineering of *Escherichia coli* for the production of cadaverine: a five carbon diamine," Biotechnol Bioeng, 2011, 108(1):93-103.
Qiu et al., "Crystal structure and substrate specificity of the β-ketoacyl-acyl carrier protein synthase III (FabH) from *Staphylococcus aureus*," Protein Sci, 2005, 14(8):2087-2094.
Rajashekhara et al., "Propionyl-coenzyme A synthetases of Ralstonia solanacearum and *Salmonella choleraesuis* display atypical kenetics," FEBS Letters, 2004, 556:143-147.
Ramsay et al., "Use of a Nylon Manufacturing Waste as an Industrial Fermentation Substrate," Applied and Environmental Microbiology, 1986, 52(1):152-156.
Ray et al., "Cocrystal structures of diaminopimelate decarboxylase: mechanism, evolution, and inhibition of an antibiotic resistance accessory factor," Structure, 2002, 10(11):1499-1508.
Rea et al., "Structure and Mechanism of HpcH: A Metal Ion Dependent Class II Aldolase from the Homoprotocatechuate Degradation Pathway of *Eschericia coli*," J. Mol. Biol., 2007, 373:866-876.
Rohdich et al., "Enoate reductases of Clostridia. Cloning, sequencing, and expression," J. Biol. Chem., 2001, 276:5779-5787.
Roje, "Vitamin B biosynthesis in plants," Phytochemistry, 2007, 68:1904-1921.

(56) References Cited

OTHER PUBLICATIONS

Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.
Ryu et al., "A novel synthesis of .beta.-trichlorostannyl ketones from siloxycyclopropanes and their facile dehydrostannation affording 2-methylene ketones," JOC, 1986, 51:2389-2391.
Salcher and Lingens, "Regulation of phospho-2-keto-3-deoxy-heptonate aldolase (DAHP synthase) and anthranilate synthase of Pseudomonas aureofaciens," J Gen Microbiol., 121(2):473-476, Dec. 1980.
Sambrook et al., Molecular Cloning—a Laboratory Manual, Cold Spring Harbor Laboratory Press, 2001.
Samsonova et al., "Molecular cloning and characterization of Escherichia coli K12 ygjG gene," BMC Microbiology, 2003, 3:2.
Sanders et al., "Characterization of the human ω-oxidation pathway for ω-hydroxy-very-long-chain fatty acids," FASEB Journal, 2008, 22(6):2064-2071.
Sanders et al., "Evidence for two enzymatic pathways for ω-oxidation of docosanoic acid in rat liver microsomes," J. Lipid Research, 2005, 46(5):1001-1008.
Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.
Scheller et al., "Generation of the Soluble and Functional Cytosolic Domain of Microsomal Cytochrome P450 52A3," J Biol Chem., 1994, 269(17):12779-12783.
Schirmer et al., "Microbial Biosythesis of Alkanes," Science, 2010, 329:559-562.
Schwartz et al., "A proteomic view of the facultatively chemolithoautotrophic lifestyle of Ralstonia eutropha H16," Proteomics, 2009, 9:5132-5142.
Seedorf et al., "The genome of Clostridium kluyveri, a strict anaerobe with unique metabolic features," Proc. Natl. Acad. Sci. USA, 2008, 105(6):2128-2133.
Shapiro et al., "Remarkable Diversity in the Enzymes Catalyzing the Last Step in Synthesis of the Pimelate Moiety of Biotin," PLoSOne, Nov. 2012, 7(11):e49440, 11 pages.
Shen et al., "Driving Forces Enable High-Titer Anaerobic 1-Butanol Synthesis in Escherichia coli," Appl. Environ. Microbiol., 2011, 77(9):2905-2915.
Shikata et al., "A novel ADP-forming succinyl-CoA synthetase in Thermococcus kodakaraensis structurally related to the archaeal nucleoside diphosphate-forming acetyl-CoA synthetases," J. Biol. Chem, 2007, 282(37):26963-26970.
Siegert et al., "Exchanging the substrate specificities of pyruvate decarboxylase from Zymomonas mobilis and benzoylformate decarboxylase from Pseudomonas putida," Port. Eng. Des. Sel., 2005, 18:345-357.
Simon et al., "Chiral Compounds Synthesized by Biocatalytic Reductions [New Synthetic Methods (51)]," Angew Chem Ed Engl., 1985, 24:539-553.
Simon, "Properties and mechanistic aspects of newly found redox enzymes from anaerobes suitable for bioconversions on preparatory scale," Pure and Appl. Chem, 1992, 64:1181-1186.
Slater et al., "Multiple β-Ketothiolases Mediate Poly(β-Hydroxyalkanoate) Copolymer Synthesis in Ralstonia eutropha," J Bacteriol., 1998, 180(8):1979-1987.
Smith et al., "Complete genome sequence of Methanobacterium thermoautotrophicum deltaH: functional analysis and comparative genomics," J Bacteriol., 1997, 179: 7135-7155.
Smith et al., "Structural analysis of ligand binding and catalysis in chorismate lyase," Archives of Biochemistry and Biophysics, Jan. 2006, 445(1):72-80.
Stok et al., "Expression, Purification, and Characterization of BioI: A Carbon—Carbon Bond Cleaving Cytochrome P450 Involved in Biotin Biosynthesis in Bacillus Subtilis," Archives of Biochemistry and Biophysics, Dec. 2000, 384(2):351-360.

Strassner et al., "A homolog of old yellow enzyme in tomato. Spectral properties and substrate specificity of the recombinant protein," J. Biol. Chem. 1999, 274:35067-35073.
Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.
Suzuki et al., "Acetylputrescine deacetylase from Micrococcus luteus K-11," BBA—General Subjects, 1986, 882(1):140-142.
Suzuki et al., "Antimicrobial Activity of Meropenem Against Main Bacterial Species Isolated from Patient Blood in 2006," J. Antibiot., 2007, 60(6):380-387.
Suzuki et al., "GriC and GriD Constitute a Carboxylic Acid Reductase Involved in Grixazone Biosynthesis in Streptomyces griseus," J. Antibiot., 2007, 60(6):380-387.
Tomita et al., "Mechanism for multiple-substrates recognition of alpha-aminoadipate aminotransferase from Thermus thermophilus," Proteins, 2009, 75(2):348-359.
Tseng et al., "Biosynthesis of chiral 3-hydroxyvalerate from single propionate-unrelated carbon sources in metabolically engineered E. coli," Microbial Cell Factories, 2010, 9:96.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.
Vioque et al., Resolution and purification of an aldehyde-generating and an alcohol-generating fatty-acyl-CoA reductase from Pea leaves (Pisum sativum L), Archives of Biochemistry and Biophysics, 1997, 340(1):64-72.
Wahlen et al., "Purification, characterization and potential bacterial wax production role of an NADPH-dependent fatty aldehyde reductase from Marinobacter aquaeolei VT8," Appl. Environ Microbiol, 2009, 75:2758-2764.
Wang and Kolattukudy, "Solubilization and purification of aldehyde-generation fatty acyl-CoA reductase from green alga Botryococcus braunii," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From Escherichia coli," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of Candida antarctica lipase A," BMC Genomics, 2010, 11:123-130.
Willis et al., "Characterization of a fatty acyl-CoA reductase from Marinobacter aquaeolei VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.

(56) References Cited

OTHER PUBLICATIONS

Wischgoll et al., "Structural basis for promoting and preventing decarboxylation in glutaryl-coenzyme, A dehydrogenases," Biochemistry, 2010, 49:5350-5357.
Woolridge et al., "Efflux of the natural polyamine spermidine facilitated by the Bacillus subtilis multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of Streptomyces griseus: Purification and properties," Eur. J. Biochem., 1985, 146:101-106.
Zhang et al., "Expanding metabolism for biosynthesis of nonnatural alcohols," Proc Natl Acad Sci U S A., 105(52):20653-20658 Epub Dec. 8, 2008.
Zhuang et al., "Divergence of function in the hot dog fold enzyme superfamily: the bacterial thioesterase YciA," Biochemistry, 2008, 47(9):2789-2796.
Zomorrodi et al., "Improving the iMM904 S. Cerevisiae metabolic model using essentiality and synthetic lethality data," BMC Systems Biology, Dec. 2010, 4(1):1-15.
"Metabolic engineering," Wikipedia, Jun. 8, 2014, XP002744570, Retrieved from the Internet: URL:https://en.wikipedia.org/w/index.php?title=Metabolicengineering&oldid=612026466 [Retrieved on Sep. 15, 2015] last paragraph.
Akatsuka et al., "The Serratia marcescens bioH gene encodes an esterase," Gene, Jan. 2003, 302:185-192.
Eriksen et al., "Protein Design for Pathway Engineering," Journal of Structural Biology, Apr. 2013, 185(2):234-242.
Invitation to Pay Fees in International Application No. PCT/US2015/036015, mailed Oct. 2, 2015, 9 pages.
Invitation to Pay Fees in International Application No. PCT/US2015/036067, mailed Sep. 18, 2015, 12 pages.
Klapa and Stephanopoulos, "Bioreaction Engineering: Modeling and Control," 2000, Springer Verlag, Heidelberg, pp. 106-124.
Moreno-Sanchez et al., "Experimental validation of metabolic pathway modeling—An illustration with glycolytic segments from Entamoeba histolytica," FEBS Journal, Jul. 2008, 275(13):3454-3469.
Palsson, "The challenges of in silico biology," Nature Biotechnology, Nature Publishing Group, US, Nov. 2000, 18(1):1147-1150.
Price et al., "Genome-scale models of microbial cells: evaluating the consequences of constraints," Nature Reviews. Microbiology, Nature Publishing Group, GB, Nov. 2004, 2(11):886-897.
Uniprot Accession No. 032472, Jun. 11, 2014, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A953, Jun. 11, 2014, 4 pages.
Uniprot Accession No. P0A6Q6, Jun. 11, 2014, 3 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
Yadav et al., "The future of metabolic engineering and synthetic biology: Towards a systematic practice," Metabolic Engineering, Feb. 2012, 14(3):233-241.
Akita et al., "Highly stable meso-diaminopimelate dehydrogenase from an Ureibacillus thermosphaericus strain A1 isolated from a Japanese compost: purification, characterization and sequencing," AMB Express, 2011, 1:43, 8 pages.
Aursnes et al., ""Total Synthesis of the Lipid Mediator PD1(n-3 DPA): Configurational Assignments and Anti-Inflammatory and Pro-resolving Actions,"" Journal of Natural Products, Feb. 2014, 77:910-916.
Bordeaux et al., "Catalytic, Mild, and Selective Oxyfunctionalization of Linear Alkanes: Current challenges," Angew. Chem. Int. Ed., 2012, 51:10712-10723.
Clomburg et al., ""Integrated engineering of Beta-oxidation reversal and omega-oxidation pathways for the synthesis of medium chain omega-functionalized carboxylic acids,"" Metabolic Engineering, Jan. 2015, 28:202-212.
Gao et al: "A novel meso-diaminopimelate dehydrogenase from Symbiobacterium thermophilum: overexpression, characterization, and potential for D-amino acid synthesis," Applied and Environmental Microbiology, 2012, 78:8595-8600.
International Preliminary Report on Patentability for International Application No. PCT/US2013/075058, mailed Jun. 25, 2015, 11 pages.
International Preliminary Report on Patentability for International Application No. PCT/US2013/075087, mailed Jun. 25, 2015, 11 pages.
International Preliminary Report on Patentability for International Application No. PCT/US2013/077445, mailed Jul. 9, 2015, 11 pages.
International Preliminary Report on Patentability for International Application No. PCT/US2013/077420, mailed Jul. 9, 2015, 14 pages.
International Preliminary Report on Patentability for International Application No. PCT/US2013/077419, mailed Jul. 9, 2015, 13 pages.
International Preliminary Report on Patentability for International Application No. PCT/US2013/077430, mailed Jul. 9, 2015, 18 pages.
International Preliminary Report on Patentability for International Application No. PCT/US2013/077413, mailed Jul. 9, 2015, 13 pages.
International Preliminary Report on Patentability for International Application No. PCT/US2013/077411, mailed Jul. 9, 2015, 12 pages.
International Preliminary Report on Patentability for International Application No. PCT/US2013/077423, mailed Jul. 9, 2015, 14 pages.
International Search Report and Written Opinion in International Application No. PCT/US2014/053222, mailed Mar. 4, 2015, 18 pages.
International Search Report and Written Opinion in International Application No. PCT/US2015/031227, mailed Jul. 31, 2015, 40 pages.
International Search Report and Written Opinion in International Application No. PCT/US2015/036050, mailed Aug. 14, 2015, 38 pages.
International Search Report and Written Opinion in International Application No. PCT/US2015/036057, mailed Aug. 14, 2015, 74 pages.
KEGG Enzyme 1.2.99.6 (last viewed on Aug. 17, 2015).
KEGG Enzyme 3.1.2.14 (last viewed on Aug. 17, 2015).
Kizer, "Application of Functional Genomics to Pathway Optimization for Increased Isoprenoid Production," Applied and Environmental Microbiology, 2008, 74(10)3229-3241.
Prather et al., "De novo biosynthetic pathways: rational design of microbial chemical factories," Current Opinion in Biotechnology, 2008, 19:468-474.
Scheps et al., "Synthesis of omega-hydroxy dodecanoic acid based on an engineered CYP153A fusion construct," Microbial Biotechnology, 2013, 6:694-707.
US Notice of Allowance in U.S. Appl. No. 13/715,981, mailed Apr. 6, 2015, 10 pages.
US Non-Final Office Action in U.S. Appl. No. 14/106,033, mailed Apr. 6, 2015, 37 pages.
US Non-Final Office Action in U.S. Appl. No. 14/138,827, mailed Apr. 24, 2015, 35 pages.
US Non-Final Office Action in U.S. Appl. No. 14/138,971, mailed Jun. 9, 2015, 44 pages.
US Non-Final Office Action in U.S. Appl. No. 14/138,904, mailed Jun. 9, 2015, 50 pages.
US Non-Final Office Action in U.S. Appl. No. 14/490,270, mailed Jul. 17, 2015, 49 pages.
US Non-Final Office Action in U.S. Appl. No. 14/130,117, mailed Aug. 21, 2015, 49 pages.
White et al., ""Carboxylic acid reductase: a new tungsten enzyme catalyses the reduction of non-activated carboxylic acids to aldehydes,"" Eur. J. Biochem., 1989, 184(1):89-96.

(56) References Cited

OTHER PUBLICATIONS

Aimin et al., "*Nocardia* sp. carboxylic acid reductase: cloning, expression, and characterization of a new aldehyde oxidoreductase family," Appl. Environ. Microbiol., 2004, 70:1874-1881.
Aloulou et al., "Purification and biochemical characterization of the LIP2 lipase from Yarrowia lipolytica," Biochim. Biophys. Acta, 2007, 1771:228-237.
Atsumi et al., "Acetolactate synthase from Bacillus subtilisserves as a 2-ketoisovalerate decarboxylase from isobutanol synthesis in *Escherichi coli*," Applied and Environ. Microbiol., 2009, 75(19):6306-6311.
Bergler et al., "Protein EnvM is the NADH-dependent enoyl-ACP reductase (FabI) of *Escherichia coli*," J. Bio Chem, 1993, 269(8):5493-5496.
Eikmanns and Buckel, "Properties of 5-hydroxyvalerate CoA-transferase from Clostridium aminovalericum," Biol. Chem, 1990, 371:1077-1082.
Fonknechten et al., "Clostridium sticklandii, a specialist in amino acid degradation: revisiting its metabolism through its genome sequence," BMC Genomics, 2010, 11:1-12.
GenBank Accession No. AAA23536, Apr. 26, 1993, 1 page.
GenBank Accession No. AAA92347.1, Mar. 15, 1996, 1 page.
GenBank Accession No. AAB99100, Aug. 27, 1996, 2 pages.
GenBank Accession No. AE000666.1, Jan. 5, 2006, 309 pages.
GenBank Accession No. D87518, Jul. 31, 1997, 2 pages.
GenBank Accession No. HQ418483.1, Apr. 4, 2011, 2 pages.
GenBank Accession No. JA114119.1, Apr. 19, 2011, 1 page.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 Pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
Horning et al., "α-Ketoglutaric Acid," Organic Syntheses, 1955, 3: 510-512.
International Search Report and Written Opinion in International Application No. PCT/US2014/052950, mailed Dec. 3, 2014, 15 pages.
International Search Report and Written Opinion in International Application No. PCT/US2013/077411, mailed Sep. 24, 2014, 18 pages.
International Search Report and Written Opinion in International Application No. PCT/US2013/077430, mailed Nov. 10, 2014, 23 pages.
Invitation to Pay Additional Fees in International Application No. PCT/US2014/053222, mailed Dec. 15, 2014, 8 pages.
Klatte et al., "Redox self-sufficient whole cell biotransformation for amination of alcohols," Bioorg & Medicinal Chem, May 2014, 22: 5578-5585.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Mutti et al., "Amination of ketones by employing two new (S)-selective w-transaminases and the His-tagged w-TA from Vibrio fluvialis," Eur. J. Org. Chem, 2012, 1003-1007 (Abstract).
Prabhu et al., "Lactate and Acrylate Metabolism by Megasphaera elsdenii under Batch and Steady-State Conditions," Applied and Environ. Microbiology, Sep. 2012, 78(24): 8564-8570.
Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.
Rizzarelli et al., "Evidence for Selective Hydrolysis of Aliphatic Copolyesters Induced by Lipase Catalysis," Biomacromolecules, 2004, 5:433-444.
Uniprot Accession No. I5YEB8, Sep. 5, 2012, 1 page.
US Non-Final Office Action in U.S. Appl. No. 13/524,883, mailed Nov. 29, 2013, 13 pages.
US Non-Final Office Action in U.S. Appl. No. 13/715,981, mailed Jun. 27, 2014, 23 pages.
US Notice of Allowance in U.S. Appl. No. 13/524,883, mailed May 29, 2014, 7 pages.
US Notice of Allowance in U.S. Appl. No. 13/715,981, mailed Dec. 16, 2014, 23 pages.
US Non-Final Office Action in U.S. Appl. No. 13/715,826, mailed Jan. 30, 2015, 24 pages.
US Notice of Allowance in U.S. Appl. No. 14/106,124, mailed Dec. 24, 2014, 31 pages.
Vyazmensky et al., "Isolation and Characterization of Subunits of Acetohydroxy Acid Synthase Isozyme III and Reconstruction of the Holoenzyme," Biochemistry, 1996, 35:10339-10346.
Zhao et al., "Prediction and characterization of enzymatic activities guided by sequence similarity and genome neighborhood networks," E-Life, Jun. 2014, 3: 1-32.

\* cited by examiner

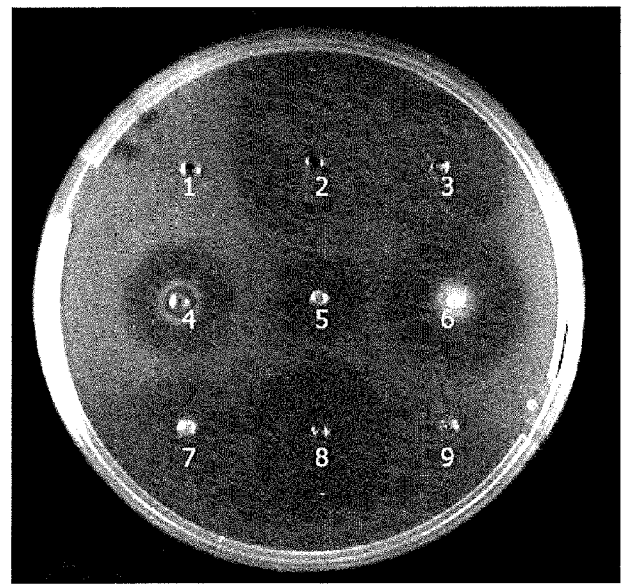
FIG. 4A
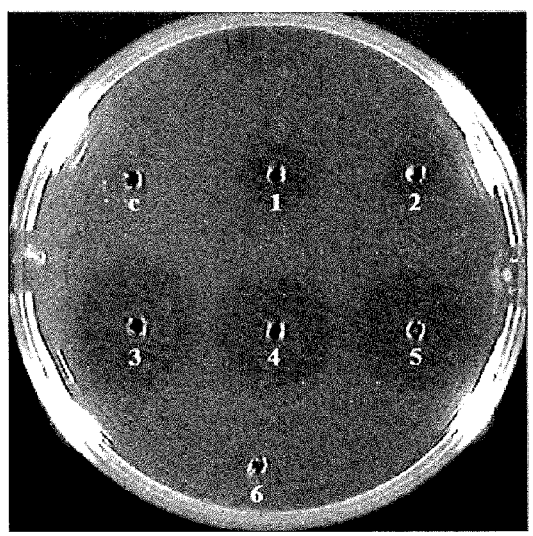 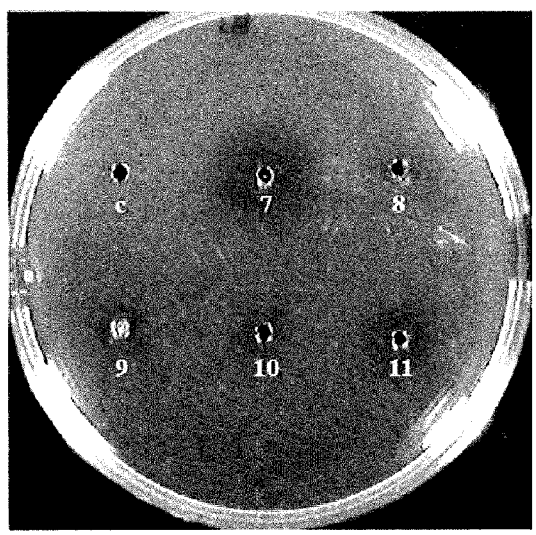
FIG. 4B  FIG. 4C

METHODS OF PRODUCING CARBOXYLIC ACIDS

CROSS-REFERENCE TO RELATED APPLICATIONS

This application claims priority to Provisional Application No. 61/498,404, filed Jun. 17, 2011, and Provisional Application No. 61/558,718, filed Nov. 11, 2011, the disclosures of which are hereby incorporated by reference in its entirety.

FIELD OF THE INVENTION

The invention relates to methods for enriching the monomer components of, diacids and adipic acid concentration of, and/or producing $\alpha,\omega$-difunctional alkanes from waste streams of industrial cycloalkane oxidation.

BACKGROUND OF THE INVENTION

Nylons are polyamides which are generally synthesized by the condensation polymerisation of a diamine with a dicarboxylic acid, ω-aminoacids, or lactams. A common variant of nylon is nylon 6,6 which is formed by the reaction of hexamethylenediamine and hexane-1,6-dioic acid (adipic acid). Alternatively, nylon 6 may be synthesized by a ring opening polymerisation of caprolactam. Hence, hexane-1,6-dioic acid (adipic acid), aminohexanoic acid, hexamethyldiamine and caprolactam are all important intermediates in the production of nylons (Anton, A. and Baird, B. R. 2005. Polyamides, Fibers. Kirk-Othmer Encyclopedia of Chemical Technology).

Industrially, these intermediates have been synthesized using petrochemical-based feedstocks. In currently used commercial processes, the starting material for producing adipic acid and caprolactam is cyclohexane, which is then air oxidized in a series of steps to form a mixture of cyclohexanone (K) and cyclohexanol (A) wherein this mixture is known as KA oil. For adipic acid, the KA oil is oxidized in a subsequent step to adipic acid via nitric acid oxidation. For caprolactam, the cyclohexanone is converted to caprolactam through several well known steps (Oppenheim, J. P. and Dickerson, G. L. 2003. Adipic Acid. Kirk-Othmer Encyclopedia of Chemical Technology). The process and various improvements have been disclosed in U.S. Pat. Nos. 2,439,513; 2,557,282; 2,791,566; 2,840,607; 2,971,010 and 3,338,959.

In the air oxidation of cyclohexane to KA oil, significant volumes of waste streams are produced comprising of mixtures of dicarboxylic acids, monoacids, hydroxy acids, cyclohexanone, cyclohexanol, and esters/oligomers of such. These waste streams are called non-volatile residue (NVR), water wash, or COP acid streams. There have been numerous publications on chemical methods and processes for recovering material from these mixtures such as U.S. Pat. No. 4,058,555. However, the recovery of carbon from these streams suffers from low yields, and a large portion of the carbon is not utilized.

Economic and environmental considerations warrant more efficient carbon utilisation of the petrochemical feedstock cyclohexane. The utilization of the components in NVR from the caustic cyclohexyl hydroperoxide (CHHP) decomposition process as a fermentation substrate was investigated briefly decades ago (Ramsay et al., Applied & Environmental Microbiology, 1986, 52(1):152-156), but to date no biological processes for the treatment of these waste streams or for the utilization of the carbon in these waste streams had been developed due to the highly toxic nature of these streams to microorganisms. Thus, these waste streams need to be disposed of by burning and this may require combustion in specially designed incinerators dependent on the nature of the steams.

Accordingly, there is a need for alternative methods for utilizing the carbon lost in these waste streams more efficiently and/or converting the carbon into useful products, rather than burning it for fuel value or disposing of it.

Summary of Various Embodiments of the Invention

The present invention addresses this and other needs through the use of enzymes, naturally, and non-naturally occurring microorganisms to improve the properties and composition of mixed organic waste streams. In particular, the inventors have surprisingly found that it is possible to use enzymes and microorganisms to convert components of the complex toxic mixture of chemicals present in these mixed organic waste streams (e.g., NVR, COP acid, and water wash waste streams) from commercial cycloalkane oxidation (e.g., cyclohexane oxidation), to produce a stream enriched in monomers that can then be converted into useful compounds such as polyols, diacids, nylon intermediates or precursors that can be converted to nylon intermediates, or polyurethane intermediates, despite the biotoxicity of components in these mixtures. This enables the recovery and/or recycle of by-products from commercial cycloalkane oxidation processes, thus providing a more economic and sustainable process.

In particular, the inventors have identified methods where certain enzymes can be used to convert the substantial amount of unavailable C6 components, present as oligomeric esters in NVR and COP acids, to monomers. Once available as monomers, the components in the hydrolyzed mixture can be chemically converted to useful products such as poyols in a much higher yield.

Alternatively, metabolically engineered microorganisms can be utilized to convert these monomers into useful products, such as a mixture of diacids, 1,6-hexanedioic acid (adipic acid), or other C6 compounds useful for the production of polymers, e.g., 1,6-hexanediol, caprolactone, 6-aminohexanoic acid, hexamethylenediamine, and caprolactam.

The inventors have also identified valerolactone as an inhibitory component in NVR. By treating the mixed organic waste stream to remove or diminish the amount of valerolactone present in the mixture, a host cell, unable to naturally grow in NVR, can grow in the presence of the treated mixture and catalyze conversion of other mixed organic waste stream components into desirable compounds.

Accordingly, the present invention provides methods for enriching monomer content in a cycloalkane oxidation process mixed organic waste stream, e.g., NVR, COP acid, or water wash waste stream, by combining a biocatalyst with a mixed organic waste stream from a cycloalkane oxidation process, and enzymatically converting dimeric and/or oligomeric components of said waste stream into monomeric components.

In some embodiments, the oligomeric ester components in mixed organic waste stream are hydrolyzed to increase the amount of monomer components in the stream. In one aspect, the methods comprise treating the mixed organic waste stream with a biocatalyst that comprises at least one hydrolase enzyme, naturally occurring host cell, or non-naturally occurring host cell, hydrolyzing oligomeric esters in said waste stream into monomers and increasing the amount of monomer components in the mixed organic waste stream.

In another aspect, the methods comprise treating the mixed organic waste stream with a naturally or non-naturally occurring host cell, which alone or in combination, hydrolyzes at least a portion of oligomeric esters in said waste stream into monomers, hydrolyzes at least a portion of lactones in the mixed organic waste stream into hydroxy-acids, or oxidizes at least a portion of linear C4-C6 monoacids, hydroxyacids, and oxo-acids present in said mixed organic waste stream to the corresponding diacids, increasing the amount of monomer components in the mixed organic waste stream.

In one aspect, the biocatalyst is an isolated enzyme or an enzyme secreted by a naturally occurring or non-naturally occurring host cell. In another aspect, the biocatalyst is a non-naturally occurring host cell secreting an endogenous or heterologous hydrolase acting on oligomeric esters or lactones and/or has a ω-hydroxylation pathway to convert monoacids to diacids and/or a cyclohexanol degradation pathway to convert cyclohexanol and cyclohexanone to adipic acid. The biocatalyst may further have an impaired ability to degrade adipic acid, 6-hydroxycaproic acid and/or caproic acid via β-oxidation. The whole cell biocatalyst may further express enzymes to convert hydroxycaproic acid, 6-oxocaproic acid and adipic acid to α,ω-difunctional alkanes where the functional groups are selected from —OH, —COOH and —NH$_2$.

In one aspect, the hydrolysis of oligomeric esters into monomers is catalyzed by an isolated or immobilized hydrolase, or an endogenous or heterologous hydrolase secreted by a natural or non-natural occurring host cell during fermentation and bioconversion.

In another aspect, the hydrolase (EC 3.1.1.-) is a lipase (EC 3.1.1.3), esterase (EC 3.1.1.1), cutinase (EC 3.1.1.74), polyhydroxyalkanoate (PHA) depolymerase (EC 3.1.1.75 & EC 3.1.1.76), lactone hydrolase such as 1,4-lactonases (EC 3.1.1.25) or gluconolactonase (EC 3.1.1.17), or combinations thereof.

In one aspect, hydrolysis of oligomeric esters into monomers is catalyzed by a hydrolase that is active at acidic pH, a physiological pH, or an alkaline pH. In another aspect, the mixed organic waste stream is treated with a non-naturally occurring host cell that can utilze and convert carbon sources in the waste stream at pH 5.0-8.0.

In one aspect, treatment with the hydrolase reduces the viscosity of the mixed organic waste stream to improve the efficiency of burning the stream and/or prepare the stream for further chemical or biological treatment. In particular, the treated mixed organic waste stream can be burned for fuel value or to produce syngas, or one or more components of the treated mixed organic waste stream is used for esterification to produce mixed esters or polyols, hydrogenation to diols, oxidation to diacids, reductive amination, sulfonation, or treatment with NH$_4$OH or polyamines.

In one aspect, the hydrolysis of oligomeric esters into monomers is performed concurrently with additional separation, chemical conversion, or enzymatic conversion by a biocatalyst. Alternatively, hydrolysis of oligomeric esters into monomers is performed prior to additional separation, chemical conversion, or enzymatic conversion by a biocatalyst.

In some embodiments, C4-C6 monoacids and hydroxyacids in the non-volatile residues, COP acid, or water wash are converted to diacids by treating the mixed organic waste stream with a naturally occurring or non-naturally occurring host cell capable of hydrolyzing at least a portion of the oligomeric esters into monomers; hydrolyzing at least a portion of the lactones into hydroxy-acids; and/or oxidizing at least a portion of the linear C4-C6 monoacids, hydroxy-acids and oxo-acids present in said mixed organic acid stream, to the corresponding diacids. In one aspect, the diacids mixture is esterified prior to separation into C4, C5, or C6 diacids.

In another aspect, the mixed organic waste stream is treated with a non-naturally occurring host cell, which alone or in combination, hydrolyzes at least a portion of the oligomeric esters into monomers; hydrolyzes at least a portion of valerolactone to 5-hydroxy-valeric acid; oxidizes at least a portion of caproic acid, 6-hydroxycaproic acid and 6-oxocaproic acid to adipic acid; converts at least a portion of the cyclic C6 components of the waste stream to adipic acid; catabolizes at least a portion of C3, C4 and C5 components present in said mixed organic waste stream; and/or catabolizes C6 components at a lower rate than C3, C4 and C5 components in said mixed organic waste stream. Such treatment increases the relative concentration of adipic acid in the stream and reduces the amount of mono-acids and hydroxyacids in the stream. In one aspect, the diacids mixture is esterified prior to separation into C4, C5, or C6 diacids. Alternatively, adipic acid is crystallized from the mixture.

In yet another aspect, the mixed organic waste stream is treated with a non-naturally occurring host cell, which alone or in combination, hydrolyzes at least a portion of the oligomeric esters into monomers; oxidizes at least a portion of caproic acid to 6-hydroxycaproic acid; converts at least a portion of the cyclic C6 components to 6-hydroxycaproic acid or 6-oxocaproic acid; catabolizes at least a portion of C3, C4 and C5 components present in said mixed organic waste stream; catabolizes C6 components at a lower rate than C3, C4 and C5 components in said mixed organic waste stream; expressing at least one biosynthetic pathway enzyme to convert adipic acid, 6-hydroxycaproic acid or 6-oxohexanoic acid to 1,6-hexanediol, 6-aminocaproic acid, ε-caprolactam or hexamethylenediamine. Such treatment converts C6 components and precursors present in said stream to α,ω-difunctional C6 alkanes.

In one aspect, the non-naturally occurring host cell that converts oligomeric esters, caproic acid, and cyclic C6 compounds to 6-hydroxycaproic acid, 6-oxohexanoic acid, and adipic acid also produces 1,6-hexanediol. In a particular aspect, the host cell producing 1,6-hexanediol expresses an aldehyde dehydrogenase that catalyzes the conversion of 6-oxohexanoic acid to 6-hydroxycaproic acid, and a alcohol dehydrogenase that catalyzes the conversion of 6-hydroxycaproic acid to 1,6-hexanediol.

In another aspect, the non-naturally occurring host cell that converts oligomeric esters, caproic acid, and cyclic C6 compounds to 6-hydroxycaproic acid, 6-oxohexanoic acid, or adipic acid also produces 6-aminocaproic acid. In a particular aspect, the non-naturally occurring host cell producing 6-aminocaproic acid expresses an aminotransferase that converts 6-oxohexanoic acid to 6-aminocaproic acid. In one aspect, the non-naturally occurring host cell producing 6-aminocaproic acid also expresseses an amidohydrolase that converts 6-aminocaproic acid to ε-caprolactam. Alternatively, the non-naturally host cell producing 6-aminocaproic acid also produces hexamethylenediamine via an aldehyde dehydrogenase that converts 6-aminocaproic acid to 6-aminohexanal, and a 1-aminotransferase that converts 6-aminohexanal to hexamethylenediamine.

In one aspect, the naturally or non-naturally occurring host cell that converts C4-C6 or C6 monoacids, hydroxy-acids and oxo-acids to diacids via the oxo-acid, has an endogenous or heterologous ω-oxidation pathway that catalyzes conversion of butyric acid, valeric acid, and/or caproic acid to succinic acid, glutaric acid, and/or adipic acid; conversion of butyric acid, valeric acid, and/or caproic acid to 4-hydroxybutyric acid, 5-hydroxyvaleric acid, and/or 6-hydroxycaproic acid; conversion of 4-hydroxybutyric acid, 5-hydroxyvaleric acid, and/or 6-hydroxycaproic acid to 4-oxobutanoic acid, 5-oxopentanoic acid, and/or 6-oxohexanoic acid; and/or conversion of 4-oxobutanoic acid, 5-oxopentanoic acid, and/or 6-oxohexanoic acid to succinic acid, glutaric acid, and/or adipic acid. In particular, the naturally or non-naturally occurring host cell with an endogenous or heterologous ω-oxidation pathway able to convert aliphatic fatty acids to diacids via hydroxyl-acids and oxo-acids, and the host cell is an n-alkane utilizing yeast or bacterium. In a particular aspect, the n-alkane utilizing yeast is *Yarrowia lipolytica, Candida tropicalis, C. albicans, C. cloacae, C. guillermondii, C. intermedia, C. maltosa, C. parapsilosis, C. zeylenoides*, or combinations thereof, or yeasts of the *Rhodotorula, Rhizopus, Trichosporon, Debaryomyces and Lipomyces* genera or combinations thereof; and wherein the n-alkane utilizing bacteria is *Pseudomonas fluorescens, P. putida, P. aeroginosa, P. oleoverans, Marinobacter hydrocarbonoclasticus, Acinetobacter* sp., such as *A. venetianus, Oleiphilus messinensis, Arthrobacter viscosus, Cupriavidus metallidurans, Rhodococcus* sp., such as *Rhodococcus rhodochrous* and *R. erythropolis, Sphingomona spaucimobilis, Burkholderia cepacia, Delftia acidovorans, Alcanivorax diesolei* or combinations thereof.

In one aspect, the naturally or non-naturally occurring host cell that converts at least a portion of the cyclic C6 components of the waste stream into 6-hydroxycaproic acid, 6-oxohexanoic acid or adipic acid has an endogenous or heterologous pathway that catalyzes conversion of cyclohexanol to 6-oxohexanoic acid; conversion of 1,2-cyclohexanediol to 6-oxohexanoic acid; and/or conversion of 6-oxohexanoic acid to adipic acid.

In one aspect, degradation of adipic acid and/or 6-hydroxycaproic acid and/or caproic acid via β-oxidation is impaired, either by preventing the C6 acids to be activated to the CoA esters, or by deletion of one or more PDX genes encoding acyl-CoA oxidases.

In a particular aspect, conversion of 1,2-cyclohexanediol to 6-oxohexanoic acid includes conversion of cyclohexane-1,2-diol to cyclohexane-1,2-dione and/or conversion of cyclohexane-1,2-dione to 6-oxohexanoic acid.

In another particular aspect, conversion of cyclohexanol to cyclohexanone includes conversion of cyclohexanone to ε-caprolactone; conversion of ε-caprolactone to 6-hydroxyhexanoic acid; and/or conversion of 6-hydroxyhexanoic acid to 6-oxohexanoic acid.

In various embodiments, some of the 6-carbon components including 6-hydroxyhexanoic acid and/or caproic acid in the non-volatile residues or water wash are converted to adipic acid.

In various embodiments, some of the residual cyclohexanone and/or cyclohexanol in the non-volatile residues or water wash are converted to 6-hydroxyhexanoic acid or 6-oxohexanoic acid.

In one aspect, the naturally or non-naturally occurring host cell is tolerant to NVR. In a particular aspect, the host cell is tolerant to at least 1% of the mixed organic waste stream by volume. In another aspect, the tolerance of the host cell to the mixed organic waste stream is improved by reducing the amount of inhibitory compounds in said stream. In a particular aspect, the inhibitory compounds are lactones, and the amount of lactones in the mixed organic waste stream is reduced by treatment of said stream with one or more biocatalysts capable of hydrolyzing the lactones to the corresponding hydroxy-acids before or during treatment of the mixed organic waste stream with the naturally occurring or non-naturally occurring host cell. In another aspect, the biocatalyst is an enzyme expressed by the host cell and secreted during fermentation.

In one aspect, the rate of catabolism of C6 compounds by the host cell is decreased to provide a higher yield of C6 components from the waste stream. In a particular aspect, degradation of caproic acid, hydroxycaproic acid, and adipic acid to acetyl-CoA through β-oxidation by the host cell is reduced. In a more particular aspect, degradation of caproic acid, hydroxycaproic acid and adipic acid through β-oxidation is reduced by deleting or inhibiting enzymes that use caproic acid, hydroxycaproic acid and adipic acid to form CoA esters. In one aspect, degradation of caproic acid, hydroxycaproic acid, and adipic acid through β-oxidation is reduced by deleting or inhibiting enzymes that oxidize CoA esters. Exemplary enzymes that form CoA esters are CoA ligases and CoA transferases. Exemplary enzymes that oxidize CoA esters are acyl-CoA oxidases, and acyl-CoA dehydrogenases.

Advantageously, the methods described herein reduce the use of petrochemical based raw materials and provide a sustainable process that utilizes waste products from a commercial industrial process. Although, these processes can be performed in new facilities if desired, these processes can be performed in existing commercial plants and thus do not require the construction of new, costly plants. Moreover, as the feedstock is generated in situ, transportation costs are minimized because the adipic acid produced may be fed directly into existing purification and/or crystallisation facilities.

In various embodiments, some of the 4-carbon and 5-carbon components of the NVR or water washed streams are catabolized or converted to the corresponding diacids.

The invention also provides for compositions comprising a mixed organic waste stream of a cycloalkane oxidation process and a biocatalyst. In one aspect, the mixed organic waste stream comprises NVR, water wash/COP acid, or caustic wash stream. In another aspect, the biocatalyst is an isolated enzyme or an enzyme secreted by a naturally occurring or non-naturally occurring host cell or a whole cell.

In another aspect, the host cell is tolerant to NVR. In a particular aspect, the host cell is tolerant to at least 1% of the mixed organic waste stream by volume.

In one aspect, the naturally or non-naturally occurring host cell comprises an endogenous or heterologous ω-oxidation pathway that is able to convert aliphatic fatty acids to diacids via hydroxyl-acids and oxo-acids, and the host cell is an n-alkane utilizing yeast or bacterium. In a particular aspect, the n-alkane utilizing yeast is *Yarrowia lipolytica, Candida tropicalis, C. albicans, C. cloacae, C. guillermondii, C. intermedia, C. maltosa, C. parapsilosis, C. zeylenoides*, or combinations thereof or yeasts of the *Rhodotorula, Rhizopus, Trichosporon, Debaryomyces and Lipomyces* genera or combinations thereof; and wherein the n-alkane utilizing bacteria is *Pseudomonas fluorescens, P. putida, P. aeroginosa, P. oleoverans, Marinobacter hydrocarbonoclasticus, Acinetobacter* sp., such as *A. venetianus, Oleiphilus messinensis, Arthrobacter viscosus, Cupriavidus metallidurans, Rhodococcus* sp., such as *Rhodococcus rhodochrous* and *R. erythropolis, Sphingomona spaucimobilis, Burkholderia cepacia, Delftia acidovorans*, or *Akanivorax diesolei* or combinations thereof.

Detailed Description of Various Embodiments of the Invention

The methods of the invention use at least one biocatalyst to enable a higher yield and improved recovery of components from organic waste streams. The term "biocatalyst," as used herein, refers to an isolated or purified enzyme, or an enzyme produced in situ by a host cell that performs a single chemical transformation of an organic molecule, or a whole cell that catalyzes a series of sequential transformations of one or more organic molecules. The isolated or purified enzyme may be purchased from commercial sources, or purified from a host cell that expressed the enzyme either naturally or non-naturally. The host cell can be naturally occurring or non-naturally occurring, e.g., genetically engineered. The host cell may be a prokaryote, such as bacteria or archaea, or a eukaryote, such as yeast or animal cells. The host cell may express and secrete the enzyme, which is capable of catalyzing a particular reaction, e.g., hydrolysis. In addition, the host cell can contain additional enzymatic pathways that catalyze different reactions. By way of example, the host cell can contain a ω-hydroxylation pathway, which catalzyes the oxidation of mono-hydroxy- and oxo-acid components in the mixed organic waste stream, or enzymes that transform a compound formed from components of the waste stream such as 6-oxohexanoic acid, to generate a more commercially valuable product such as 6-aminocaproic acid.

In particular, the biocatalyst hydrolyzes oligomeric esters into monomers. This improves the burn value the waste stream and/or improves the composition of the waste stream by producing monomers that are available for subsequent chemical or enzymatic processing, such as enriching diacids, adipic acid, and difunctional alkanes. An important step in the development of the methods described herein is the identification of a host cell that naturally expresses and/or has been genetically modified to express the various enzymes and pathways necessary for the conversion of the compounds present in the NVR, COP acid, and water wash waste of industrial cyclohexane oxidation into more desirable compounds. In some cases, the naturally and non-naturally occurring host cells can use those compounds present in the NVR and water wash waste (which cannot easily be converted to 6-oxohexanoic acid) as a nutrient source for growth.

The inventors surprisingly discovered that the host cells remain viable and the enzymes active in the presence of mixed organic waste streams, and able to convert the less desirable components of the waste stream into industrially and commercially useful compounds or intermediates. Furthermore, the inventors' discovery that host cells are able to tolerate (and, in some instances, catabolize components of) NVR and water wash waste streams of industrial cyclohexane oxidation, despite the array of inhibitory chemicals present in NVR and water wash waste as by-products of the oxidation process, was also unexpected.

DESCRIPTION OF THE FIGURES

FIG. 4 shows photographs of representative clearance plate assays testing the ability of commercial esterases and lipases to hydrolyze NVR and COP acid oligomers. FIG. 4, panel A shows hydrolysis of COP acid (4% v/v) by esterases: well 1 is a control (no enzyme, phosphate buffer only); well 2 is *Mucor miehei* esterase; well 3 is *Pseudomonas fluorescens* esterase; well 4 is *Pseudomonas* sp. Cholesterol esterase; well 5 is *Bacillus stearothermophilu* esterase; well 6 is Horse liver esterase; well 7 is *Candida lipolytica* esterase; well 8 is Rhozopusoryza esterase; and well, 9 is *Saccharomyces cerevisiae* esterase. FIG. 4, panels B and C show hydrolysis of COP acid (4% v/v) by lipases: c—no enzyme control (phosphate buffer), well 1. *Thermomyceslanuginosus*, well 2. *Burholderia capacia* lipase, well 3. *Mucor miehei* lipase, well 4. *Rhizomucor miehei* lipase, well 5. *Pseudomonas fluorescens* lipase, well 6. *Penicillium camemberti* lipase, well 7. *Aspergillus niger* lipase, well 8. *Aspergillus niger* amano lipase A, well 9. *Candida antartica* lipase A, well 10. *Candida rugosa* lipase type III, and well 11. *Rhizopus niveus* lipase.

MIXED WASTE STREAMS: NON-VOLATILE RESIDUES, WATER WASH WASTE, AND COP ACID

Figure 1:
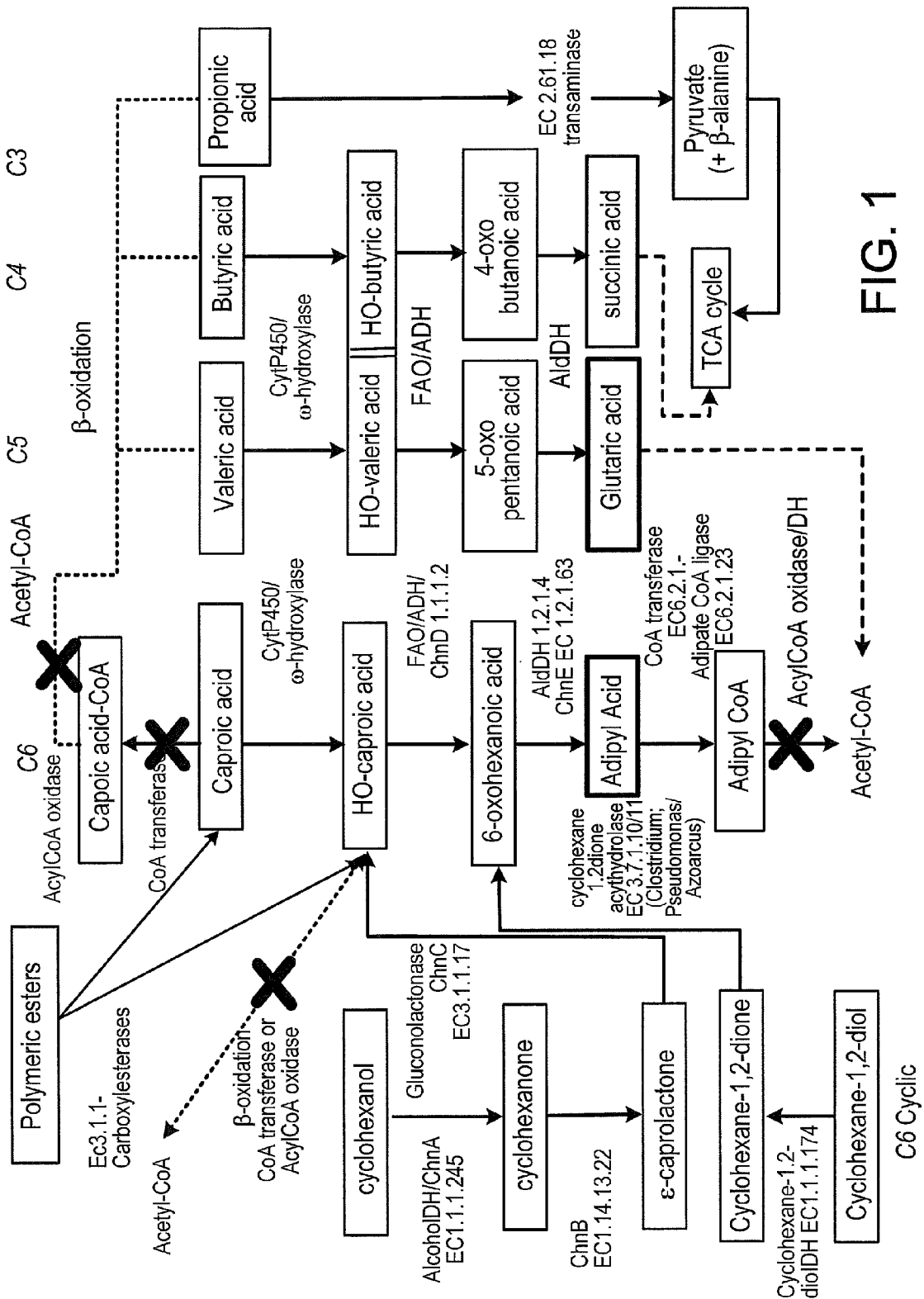
FIG. 1 is a schematic illustration of the enzyme conversions which are involved in the conversion of aliphatic and cyclic C6 components of the NVR and water wash waste of industrial cyclohexane oxidation to adipic acid. The figure also illustrates the conversions necessary to convert C3-C5 components of the NVR and water wash waste into compounds that can be fed into the central metabolism of a cell such that the cell may use those compounds for growth. Further, the figure illustrates those enzyme conversions that may be inhibited in the engineered cells of the invention to increase the overall yield of the desired product. These inhibited pathways are indicated by the presence of a cross over the arrow showing the direction of conversion.

Commercial cycloalkane oxidation to diacid processes generally involves two steps. In the first of these steps, cycloalkane is oxidized using air to produce a mixture of cycloalkanol and cycloalkanone. This mixture is then oxidized to the diacid using nitric acid. Several by-product streams are generated during production of the KA mixture. More specifically, when cyclohexane is oxidized with oxygen or a gas containing oxygen, an intermediate stream which contains cyclohexanol (A), cyclohexanone (K), and cyclohexyl hydroperoxide (CHHP) in cyclohexane is produced. This intermediate stream also includes co-products which interfere with subsequent processing steps intended to convert CHHP to KA. Therefore, commercial processes may include a step wherein the intermediate stream which contains K, A, and CHHP is contacted with water or caustic (such as described in U.S. Pat. No. 3,365,490) to remove the unwanted co-products. This extraction step yields (i) a purified cyclohexane stream which contains K, A and CHHP; and (ii) a water waste stream.

The term "water wash," "water wash waste stream," or "water waste stream" as used herein refers to the aqueous stream produced by water extraction of cyclohexane oxidate (Oppenheim, J. P. and Dickerson, G. L. 2003. Adipic Acid. Kirk-Othmer Encyclopedia of Chemical Technology). The water wash contains various mono- and di-acids, hydroxyacids, and other oxidation byproducts foimed during the initial oxidation of cyclohexane.

Once conversion of CHHP to K and A has been completed, the resulting mixture is refined in order to recover (i) unreacted cyclohexane for recycle, and (ii) to obtain purified K and A for subsequent oxidation to adipic acid or conversion to caprolactam. The term "non-volatile residue stream" or "NVR" as used herein refers to the high-boiling distillation bottoms from distillative recovery of cyclohexane oxidation products cyclohexanol and cyclohexanone having low chromium content, more suitable for combustion (Oppenheim, J. P. and Dickerson, G. L. 2003. Adipic Acid. Kirk-Othmer Encyclopedia of Chemical Technology). NVR comprises several components, including, but not limited to, butyric acid, valeric acid, caproic acid, 5-hydroxyvaleric acid, 6-hydroxycaproic acid, valerolactone, succinic acid, glutaric acid, and adipic acid as well as cylohexanol, cyclohexanediols and cyclohexanone.

To summarize, the co-product streams, sometimes referred to herein as "by-product" streams, available from a cyclohexane oxidation processes include "Water Wash" (the aqueous stream produced by water extraction of cyclohexane oxidate) and "NVR" (the high-boiling distillation bottoms from KA refining, CAS Registry Number 68411-76-7). Concentration of water wash by removal of at least some of the water produces a concentrated water extract stream known as "COP Acid." The term "COP acid" as used herin refers to a water wash stream that had been thermally treated to remove peroxides and concentrated to remove at least some of the water (CAS Registry Number 68915-38-8). See U.S. Pub. No. US 2004/0054235, incorporated herein by reference, describing production of NVR, and U.S. Pub. Nos. US 2012/0064252 and US 2012/0101009, incorporated herein by reference, describing processing of NVR, Water Wash, or COP acid through conversion of free acid functional groups to monomeric esters and oligomeric esters, and converting oligomeric esters to monomeric esters.

In an embodiment, "COP Acid" may be provided by contacting cyclohexane air oxidation products with water in an extraction step and separating the aqueous phase, the extract hereinafter called "Water Wash." In an embodiment, the "Water Wash" is thermally treated to destroy peroxides that may pose difficulties during storage and shipment. The water wash may be concentrated by partial removal of water to reduce storage volume and transportation cost.

In an embodiment, COP Acid generally may contain about 10% to 70% by weight water. In an embodiment, COP Acid may contain about 10% to 50% by weight water. In an embodiment, NVR may contain about 10% to 50% by weight water. In an embodiment, Wash Water may contain about 70% to 90% by weight water. In an embodiment, Wash Water may contain about 85% by weight water.

As starting materials for the methods, a portion of products from an aqueous extract from a cyclohexane oxidation process (or from a system), hereinafter called "Water Wash", a concentrated aqueous extract from a cyclohexane oxidation process, herein after called "COP Acid", the distillation bottoms from KA refining referred to herein as nonvolatile residue or "NVR", or a combination thereof, can be used. In regard to "a combination thereof", any one or a combination of two (e.g., water wash and COP acid; water wash and NVR;

or COP and NVR) or a combination of all three (i.e., water wash, COP acid, and NVR) can be considered a combination thereof.

Components of Mixed Organic Waste Streams

The non-volatile residues and water wash waste streams of cyclohexane oxidation comprise a mixture of compounds, some of which are linear C6 molecules, some are cyclic C6 molecules, and some are polymeric esters comprising linear C6 molecules. Other compounds of shorter chain length are also present in the NVR and water wash waste streams.

In particular, the non-volatile residues and water wash waste streams contain both mono- and poly-functional products. The functional groups which may be present on these products include acids, peroxides, ketones, alcohols, esters, and oligomers. Other functional groups such as aldehydes, lactones and alkenes may also be present. A single molecule may include one or more functional groups (Ramsay et al., Applied & Environmental Microbiology, 1986, 52(1):152-156).

Examples of products which include a hydroxylacid group and which may be present in the non-volatile residue and/or water wash waste streams include but are not limited to hydroxyhexanoic acid, hydroxypentanoic acid, hydroxybutanoic acid, hydroxypropanoic acid and hydroxyacetic acid. In one embodiment, the acid group may be positioned at one end of a linear hydrocarbyl chain, while a hydroxyl group may be present at various positions on the chain.

In one embodiment, the hydroxyhexanoic acid is 2-hydroxyhexanoic acid, 3-hydroxyhexanoic acid, 4-hydroxyhexanoic acid, 5-hydroxyhexanoic acid or 6-hydroxyhexanoic acid.

In one embodiment, the hydroxypentanoic acid is 2-hydroxypentanoic acid, 3-hydroxypentanoic acid, 4-hydroxypentanoic acid or 5-hydroxypentanoic acid.

In one embodiment, the hydroxybutanoic acid is 2-hydroxybutanoic acid, 3-hydroxybutanoic acid or 4-hydroxybutanoic acid.

In one embodiment, the hydroxypropanoic acid is 2-hydroxypropanoic acid or 3-hydroxypropanoic acid.

Examples of products which include a mono-acid group and which may be present in the non-volatile residue and/or water wash waste streams include but are not limited to: formic acid, acetic acid, propanoic acid, butanoic acid, pentanoic acid and hexanoic acid.

Examples of products which include a di-acid group and which may be present in the non-volatile residue and/or water wash waste streams include but are not limited to: malonic acid, succinic acid, glutaric acid, adipic acid, fumaric acid, maleic acid, oxalic acid and hex-2-enedioic acid.

Examples of products which include a keto-acid group and which may be present in the non-volatile residue and/or water wash waste streams include but are not limited to: an alpha-keto acid, for example a 2-oxo acid such as pyruvic acid, a beta-keto acid, for example a 3-oxo acid such as acetoacetic acid, a gamma-keto acid, for example, a 4-oxo acid such as 4-oxo pentanoic acid (also known as levulinic acid) and 5-oxo hexanoic acid.

Examples of products which include an alcohol group and which may be present in the non-volatile residue and/or water wash waste streams include but are not limited to: cyclohexanol, propanol (e.g. 1-propanol, 2-propanol), butanol (e.g. 1-butanol, 2-butanol, etc), pentanol (e.g. 1-pentanol, 2-pentanol etc.), hexanol (e.g. 1-hexanol, 2-hexanol, etc.) and diols such as 1,2-, 1,3- and 1,4-cyclohexanediols, various butanediol isomers and various pentanediol isomers.

Examples of products which include a peroxide group and which may be present in the non-volatile residue and/or water wash waste streams include but are not limited to: cyclohexylhydroperoxide and hydroxyhexanoic hydroperoxide.

Examples of products which include an ester group and which may be present in the non-volatile residue and/or water wash waste streams include but are not limited to: cyclohexylformate and cyclohexylpentanoate.

Examples of products which include a ketone group and which may be present in the non-volatile residue and/or water wash waste streams include but are not limited to: cyclohexanone and cyclopentanone.

Examples of products which include an aldehyde-acid group and which may be present in the non-volatile residue and/or water wash waste streams include but are not limited to: 5-formyl pentanoic acid and 4-formyl butanoic acid.

Examples of products which include a lactone group and which may be present in the non-volatile residue and/or water wash waste streams include but are not limited to: gamma-butyrolactone, delta-valerolactone, gamma-valerolactone and epsilon-carpolactone.

Examples of products which include an alkene group and which may be present in the non-volatile residue and/or water wash waste streams include but are not limited to: cyclohex-ene-1-one, pentenoic acid and cyclohexene-ol.

Examples of products which include ester group and which may be present in the non-volatile residue and/or water wash streams include but are not limited to: esters or oligomers of 6-hydroxyhexanoic acid and cross esters or oligomers containing 6-hydroxyhexanoic acid and dicarboxylic acids such as 1,6-hexandoic acid.

Hydrolysis of Oligomeric Mixed Organic Waste Stream Components by a Biocatalyst

Up to 60% of the available C6 carbon molecules in NVR are present as ester oligomers of hydroxycaproic acid, adipic acid and hexanoic acid, as well as, mixed polymeric esters incorporating C4-C5 hydroxy-acids, monoacids and cyclic alcohols. Similar oligomeric esters are present in COP acid, albeit with lower heterogeneity, consisting predominantly of hydroxy-caproic acid. Hydroxy-caproic acid is the main component of these oligomers, while mono-acids and diacids act as chain terminators, resulting in oligomers of different chain lengths. Commercially viable utilization of NVR and COP acid requires release of the monomers from the oligomeric esters to improve the yield of products such as polyols, C4-C6 dibasic acids or dibasic ester mixtures or $\alpha,\omega$-difunctional C6 alkanes useful for polymer applications that can be derived from these waste streams. The high level of oligomers in NVR also lead to high viscosity and low efficiency of burning where NVR is disposed of as boiler fuel.

Carboxyl ester hydrolases (EC3.1.1.-) are hydrolytic enzymes that hydrolyze esters into alcohols and acids. Lipases (EC 3.1.1.3) are a subclass of these hydrolases which hydrolyze lipids and can act at the interface of aqueous and organic phases. Esterases (EC 3.1.1.1), cutinases (EC 3.1.1.74, polyhydroxyalkanoate (PHA) depolymerases (EC 3.1.1.75 & EC 3.1.1.76), lactone hydrolase such as 1,4-lactonases (EC 3.1.1.25) or gluconolactonases (EC 3.1.1.17) also hydrolyze ester bonds.

Lipases can be classified based on the topography of their binding sites, gene sequence, function or other properties. The Lipase Engineering Database (LED) integrates information on sequence, structure and function of lipases, esterases and related proteins with the $\alpha/\beta$ hydrolase fold to generate a classification system for all lipases (Widmann et al., BMC Genomics 2010, 11:123). Depending on the amino acids involved in forming the oxyanion hole, which, in addition to the catalytic triad (Ser-Asp(Glu)-His), form the active site, lipases from any organism can be categorized into three groups: the GGGX-, GX- and the Y-class. Once lipases with the desired activity against a given substrate had been identified, this database is a useful resource to extrapolate the results to identify additional enzymes with desired specificities and properties.

In one embodiment, the invention provides for the use of one or more enzymes such as a combination of lipases and esterases. For example, in one aspect, the lipase hydrolyzes an oligomeric ester into a smaller oligomer and the esterase hydrolyzes the smaller oligomer into monomers The methods of the present invention provide the means to improve the properties and composition of a mixed organic waste stream from a cyclohexane oxidation process by applying at least one biocatalyst to the waste stream. Organic waste streams are generated by a limited number of sources, and the waste streams are most often burned for fuel value or to produce syngas. As a result of burning the waste streams or converting them into syngas via, e.g., steam reforming, the commercially valuable C6 components of the streams are lost. In addition, as much as 40-60% of the C6 components of the waste streams are "trapped" as oligomers, which results in poor recovery of useful compounds from further chemical or enzymatic processing using the waste streams as input materials and reduces the efficiency of burning the waste streams for fuel, as oligomers do not burn as efficiently as monomers. Without being bound by theory, it is believed that oligomers in NVR increase the viscosity of the stream, which hinders efficient atomisation at the burner tip. Furthermore, it is believed that since the oligomers vary in composition and quantity, it is very difficult to optimize the burning process. Elimination of the oligomers from NVR and COP acid may thus result in lower viscosity of the stream, which results in a more uniform stream, that is easier to dispose of by incineration.

These limitations associated with mixed organic waste streams, e.g., NVR and COP acid, diminishes use of the waste streams and their C6 components in commercially valuable operations, e.g., production of diacids or nylon intermediates.

The present invention provides methods for releasing the C6 components as monomers by applying at least one biocatalyst to the waste stream, wherein the biocatalyst hydrolyzes the oligomers to form monomers. The monomers can be more efficiently burned for fuel and/or used in subsequent chemical and enzymatic processing to provide improved yield.

In one aspect, the biocatalyst is an isolated enzyme, an immobilsed enzyme, a host cell that naturally expresses an enzyme, or a host cell that has been modified to secrete a carboxylesterase from the $\alpha,\beta$-hydrolase fold family (EC 3.1.1.-).

The hydrolase capable of hydrolyzing oligomeric esters into monomers may be an isolated or immobilized enzyme. Alternatively, the hydrolase may be an endogenous or heterologous hydrolase secreted by a naturally occurring or non-naturally occurring host cell during fermentation and bioconversion.

In one aspect, the hydrolase capable of hydrolyzing oligomeric esters into monomers is a carboxylic ester hydrolase (EC 3.1.1.-). In another aspect, the hydrolase is selected from a lipase (EC 3.1.1.3), an esterase (EC 3.1.1.1), a cutinase (EC 3.1.1.74), a polyhydroxyalkanoate (PHA) depolymerase (EC 3.1.1.75 & EC 3.1.1.76), a lactone hydrolase, or combinations thereof. In a particular aspect, the lactone hydrolase is a 1,4-lactonases (EC 3.1.1.25) or a gluconolactonases (EC 3.1.1.17).

Depending on the specific cyclohexane oxidation process from which the NVR, COP acid, water wash or caustic waste streams are generated, and the intended application, hydrolysis of the oligomeric esters may be performed under different pH conditions. For example, NVR, COP acid, and water wash from cyane oxidation is acidic, while the caustic CHHP process results in an alkaline NVR stream and a caustic water wash & COP waste stream. It is thus advantageous to be able to hydrolyze the oligomers present in the different NVR and concentrated water wash stream with different enzymes that can be used under acidic, neutral or basic conditions.

The mixed organic waste stream can be treated with the hydrolase with or without adjusting the pH and water content of the mixture. The hydrolase is selected according to its ability to retain its enzymatic activity at the appropriate pH such that it can hydrolyze oligomeric esters present in the waste stream to monomers at a near neutral pH, an acidic pH, or an alkaline pH. In one aspect, the mixed organic waste stream is treated with a hydrolase that is active at an acidic pH, i.e., pH less than 6. In another aspect, the mixed organic waste stream is treated with a hydrolase that is active at an alkaline pH, i.e., pH greater than 8. In yet another aspect, the mixed organic waste stream is treated with a hydrolase that is active at a physiological pH, i.e., pH 6-8.

Treatment of the mixed organic waste stream with a hydrolase can reduce the viscosity of the stream and improve the efficiency of burning the stream. In addition, hydrolase treatment of the mixed organic waste stream can also prepare the stream for further chemical and/or biological processing.

In one aspect, hydrolase treated mixed organic waste streams, such as NVR, are burned for fuel value or to produce syngas. Without being bound by theory, it is believed that if the monomers are released from oligomeric esters by hydrolysis, the resultant mixture burns more efficiently when disposed of as boiler fuel. In another aspect, at least one component from the hydrolase treated mixed organic waste streams, such as NVR, is used for further chemical processing. Exemplary further chemical processing of the monomers includes esterification to produce mixed esters or polyols, hydrogenation to diols, oxidation to diacids, reductive amination, sulfonation, or treatment with $NH_4OH$ or polyamines.

Where the waste stream treated with a hydrolase is intended to be used as a boiler fuel, or where the waste stream is treated with a hydrolase to prepare it for further chemical processing, it is advantageous to minimize dilution of the waste stream with water and to minimize adjustment of the pH of the mixture prior to or during treatment with the hydrolase. A hydrolase that retains activity at a low pH is most advantageous for the treatment of waste streams resulting from cyane oxidation process while a hydrolase that retains activity at alkaline pH is most advantageous in the case of waste streams resulting from the CHHP process. Where the waste stream is intended to be subjected to biological treatment by host cells to catabolize components of the waste stream and/or convert components in the waste stream to diacids or $\alpha,\omega$-difunctional alkanes, it is most advantageous to employ a hydrolase that is active at near physiological pH (pH 5-8).

For example, the inventors demonstrated that, despite *Y. lipolytica's* broad growth pH range (pH 3.0-9.0), the growth rate of the host cell on carbon sources present in the mixed organic waste streams may be significantly inhibited at an acidic pH and/or an alkaline pH (growth inhibition in NVR at pH>8.0 and pH<5.0). See, Example 2. In one aspect, the mixed organic waste stream is treated with host cell biocatalyst that can utilize carbon sources in the waste stream at pH 5.0-8.0.

Hydrolysis of the oligomeric ester components of the mixed organic waste stream can be performed concurrently with additional separation, chemical conversion, or enzymatic conversion by enzymes that are secreted by a host cell during fermentation. The mixed organic waste stream can be treated with a hydrolase before fermentation by treating the stream with a free or immobilised hydrolase or during fermentation by adding a biocatalyst to the fermentation broth in batch, step-wise, or with the nutrient feed. Alternatively, the host cell can secrete enzymes during fermentation into the fermentation broth, which hydrolyze oligomeric esters present in NVR.

Carboxyl esterases are known that are active at near physiological pH (pH 5-8). Those skilled in the art will know that the pH optimum, substrate specificity, and activity of such hydrolases can be altered by enzyme engineering employing rational design or directed evolution techniques. (Dalby, P. A. (2003). Optimizing enzyme function by directed evolution. Current Opinion in Structural Biology, 13, 500-505). In Example 1, several lipases and esterases are provided that are able to hydrolyze oligomeric esters in NVR and COP acid at pH 5-8. Furthermore, examples of esterases that displayed hydrolytic activity for oligomeric esters in NVR and COP acid at pH 3.5, such as the esterase from *Mucor miehei* (E1) and *Rhizopus oryzae* (E12), and an alkaline esterase that only displayed activity at pH>8 from *Streptomyces diostotochromogenes* (E8) are provided in Example 1.

Carboxyl esterases that are active at very low pH (pH<3.5) are not well documented. However, the inventors identified several hydrolases that can be utilized to treat NVR and COP acid streams to hydrolyze the oligomeric esters at pH<5., such as the lipases from *Aspergillus niger* NCIM 1207 (GenBank An16g01880; SEQ ID NO:6), *Kurtzmanomyces* sp. I-11 (GenBank BAB 91331.1; SEQ ID NO:5), the hyperthermophilic archaeon *Pyrobaculum calidifontis* Val (GenBank BAC06606; SEQ ID NO:8), and *Picrophilus torridus* esterase (GenBank AAT43726; SEQ ID NO:7). It has been shown that *Aspergillus niger* NCIM 1207 produces high levels of extracellular lipase active at pH 2.5 (Mahadik et al., 2002. Process Biochemistry, 38: 715-721). This unique lipase from *A. niger* was purified and characterized under submerged feimentation (Mhetras et al., 2009. Bioresource Technology, 100: 1486-1490). It is a 32.2 kDa protein with a pI of 8.5, an optimum temperature of 50° C., and optimum pH at 2.5. At lower pH (such pH1.5), the activity decreases.

The *Kurtzmanomyces* sp. I-11 strain is a high level producer of mannosylerythritol lipid produced when the cells are grown in a medium containing soybean oil as a sole carbon source. During the initial phase of cultivation, the pH of the culture broth dropped to 3.2 and the soybean oil was rapidly hydrolyzed to the fatty acid and the glycerol at that pH, suggesting that acidophilic lipase(s) was produced in the culture broth. *Kurtzmanomyces* sp. I-11 strain lipase shows a high sequence identity with the *Candida antarctica* A lipase, which had been shown by the inventors to hydrolyze oligomeric esters in NVR and COP acid with high activity (L5 in example 1). An extracellular lipase produced by the yeast *Kurtzmanomyces* sp. I-11 was purified and characterized (Kakugawa et al., 2002. Bioscience Biotechnology Biochemistry, 66(5): 978-985). It is a 49 kda protein with an optimum temperature at 75° C. but the activity is stable at temperatures below 70° C. This acidic lipase has an activity pH range in acidic regions (pH 1.9-7.2) and the activity is stable in the presence of various organic solvents at concentration of 40%.

The hyperthermophilic archaeon *Pyrobaculum calidifontis* Val has been reported to produce a highly active thennostable carboxyesterase. This esterase was found to be one of the most thermostable and thermophilic lipolytic enzymes to be reported. It is a 34.3 kDa protein, showing an optimum temperature at 90° C., and optimum pH at 7. This esterase is stable after incubation with various water-miscible organic solvents at concentration of 80% and exhibits activity in the presence of organic solvents (Hotta et al., 2002. Applied and Environmental Microbiology, 68(8):3925-3931). *Picrophilus torridus* represents an unique model organism to study the genetic and molecular mechanisms responsible for the ability to thrive under extremely harsh conditions (optimal growth at pH 0.7 and 60° C.) and a promising source of extremely stable esterases and lipases. Two genes encoding esterases of *P. torridus* were identified and characterized. One of these esterases (Est B) shows a high ability to hydrolyze fatty acid esters in the presence of various organic solvents. EstB is a 27 kDa esterase with the highest activity measured at 70° C. (Hess et al., (2008). Extremophiles, 12:351-364).

Cutinases differ from lipases in that they do not require interfacial activation since their catalytic site is not covered by a lid and therefore remains accessible to substrates in solution (Martinez et al., 1992). Cutinases are thus active regardless of the presence of an interface and are thus able to hydrolyze both soluble and insoluble substrates. *Aspergillus oryzye* secretes a cutinase (AoC) that is able to hydrolyze oligomers containing C6 carboxylic acids and is stable and active at pH>11 (Maeda, H. et al., (2005). Purification and characterisation of a biodegradable plastic-degrading enzyme from *Aspergillus oryzae*. Applied and Environmental Biotechnology, 67: 778-788).

Other cutinases that is useful to hydrolyze oligomeric esters in NVR and COP acid due to their broad substrate specificity activity and stability across a wide pH range include the cutinases from *Alternaria brassicicola*, (AbC), *Aspergillus fumigatus*, (AfC), *Humicola insolens*, (HiC), and *Fusarium solani*, (FsC). The cutinase from the phytopathogen *Fusarium solani* sp. pisi (Egmond et al. 2000) has been found to degrade a wide range of substrates, including cutin, carboxylic esters, triacylglycerols (TAGs) and phospholipids (15) with both short and long-chain fatty acids. This enzyme is also active on soluble substrates, such as short-chain p-nitrophenyl esters. The *F. solani* cutinase operates within a broad pH range (2-12), having optimal activity at pH 8.5 and was shown to be moderately thermophilic within (40-60° C., Peterson et al., 2001). Moreover, wild type *F. solani* sp. *pisi* was shown to be capable of degrading polycaprolactone and using it as a source of carbon and energy. Cutinase activity was repressed by the presence of glucose (0.5% w/w) in the media and was induced by the enzymatic products of polycaprolactone degradation (Murphy et al., 1996). BLAST search for proteins similar to *F. solani* Cutinase 1 indicated that there are two major groups of organisms which are secreting cutinases. They are either fungi plant pathogens or *Mycobacteria*. Of the fungal cutinases, HiC displays the highest activity for polycaprolactone degradation at elevated temperatures and under all pH values due its high thermal stability. AoC, AfC, and HiC retain a significant amount of hydrolytiv activity under more extreme temperature and pH conditions. By contrast, AbC and FsC are the least thermally stable and retain little activity at high temperatures and low pH values.

The enzymes described in this section may be used in any of the methods described herein or may be included in any of the compositions described herein.

Methods to Increase the Relative Amount of Diacids in Mixed Organic Waste Streams The present invention provides further means for improving the properties and composition of mixed organic waste streams by converting monoacid and hydroxyacid components into diacids. The main components of these waste streams consist of a mixture of C4-C6 monoacids, hydroxyacids, and diacids. However, the diacids, which have many applications, cannot easily be separated from the mono-acid and hydroxyacid components in the waste stream, thereby limiting the usefulness and yields of the waste stream for further chemical or biological processing in addition to other potential applications.

The present methods employ a biocatalyst to enzymatically convert linear C4, C5, and C6 mono-acid and hydroxyacid components in NVR, as well as cyclic C6 components, into a mixture of C4, C5, and C6 diacids. The resulting diacids mixture can be used as is, i.e., without further modification or processing. Alternatively, the diacids mixture can be separated into C4, C5, and C6 diacids, or esterified and then separated into C4, C5, and C6 diacids, or adipic acid can be crystallized out of the diacids mixture. Biocatalysts may be used to increase the monomer components of NVR and COP acid, which contain a significant amount of oligomeric esters that effectively trap monomers from use in other applications, e.g., burn value and/or conversion to adipic acid or difunctional alkanes.

Enzymatic conversion of the mono-acids and hydroxyacids to diacids increases the relative amount of diacids in the waste stream, which increases recovery of diacids from separation from the other waste stream components. In particular, these methods can increase the relative amount of diacids in the mixed organic waste stream by hydrolyzing at least a portion of the oligomeric esters into monomers, hydrolyzing at least a portion of the lactones into hydroxy-acids, oxidizing at least a portion of the linear C4, C5, and C6 monoacids, hydroxyacids, and oxo-acids present in the mixed organic waste streams to the corresponding diacid. Preferably, hydrolases are used to hydrolyze oligomeric esters present in NVR and COP acid waste streams into monomers. A variety of other biocatalysts may be used in NVR and COP acid, as well as water wash waste stream, to hydrolyze lactones into hydroxy-acids and/or oxidize linear C4, C5, and C6 monoacids, hydroxyacids, and oxo-acids to diacids.

The hydrolase capable of hydrolyzing oligomeric esters into monomers may be an isolated or immobilized enzyme. Alternatively, the hydrolase may be an endogenous or heterologous hydrolase that is secreted by a naturally occurring or non-naturally occurring host cell during fermentation and bioconversion.

Preferably, the biocatalyst that enzymatically converts mono-acids and hydroxy-acids into diacids is a naturally occurring or non-naturally host cell. For example, Y lipolytica is a naturally occurring host cell that is capable of utilizing the carbon sources in NVR for growth. Additionally, a naturally occurring or non-naturally occurring host cell biocatalyst can be used for enzymatic converstion of waste stream components into diacids because the conversion involves a cytochrome p450 enzyme, which is an integral transmembrane protein, and thus requires a host cell that comprises the p450 enzyme pathway.

1. Increasing the Relative Concentration of Adipic Acid from 6-Oxohexanoic Acid

6-Oxohexanoic acid can be further converted into various compounds which have use in the synthesis of nylons. For instance, 6-oxohexanoic acid can be converted into hexane-1,6-dioic acid (adipic acid). Further, adipic acid or 6-oxohexanoic acid can be converted into 6-aminohexanoic acid, caprolactam, 6-aminohexanal or hexane-1,6-diamine (hexamethylenediamine). The present invention also provides methods for generating these compounds.

i) Hydrolyzing Oligomeric Esters and Lactones to Release Linear $C_6$ Components In one aspect, the production of 6-oxohexanoic acid from mixed organic waste streams involves hydrolyzing polymeric and oligomeric esters present in the waste streams, such as NVR and/or water wash. These dimeric, trimeric, tetrameric or oligomeric esters are comprised of linear $C_6$ molecules that can be converted to 6-hydroxyhexanoic acid, caproic acid and potentially 1,6-hexanedioic acid, after release from the polymers and oligomers. Thus, the invention provides a method of producing 6-hydroxyhexanoic acid from mixed organic waste streams of cyclohexane oxidation, comprising the use of a biocatalyst from the α,β-hydrolase fold family, such as carboxylesterases, including esterases/lipases and polyhydroxyalkanoate (PHA) depolymerases.

One step in the production of 6-oxohexanoic acid from polymeric esters comprised of linear $C_6$ molecules is the conversion of 6-hydroxyhexanoic acid to 6-oxohexanoic acid. In one aspect of the invention, a biocatalyst, such as a fatty alcohol oxidase or an alcohol dehydrogenase, is used to enzymatically convert 6-hydroxyhexanoic acid to 6-oxohexanoic acid.

Another step in the production of 6-oxohexanoic acid from polymeric esters comprised of linear $C_6$ molecules is the conversion of caproic acid to 6-hydroxyhexanoic acid. In one aspect of the invention, a biocatalyst, such as a ω-hydroxylase, is used to enzymatically convert caproic acid to 6-hydroxyhexanoic acid.

These enzymatic conversions can be combined into a single method, instead of two separate steps. In this aspect, 6-oxohexanoic acid is produced from mixed organic waste streams using a combination of enzymes, such as a carboxylesterase, a co-hydroxylase, and a fatty alcohol oxidase or alcohol dehydrogenase.

ii) Converting Linear $C_6$ Components to 6-Oxohexanoic Acid

One step in the production of 6-oxohexanoic acid from hexanoic acid is the conversion of hexanoic acid (caproic acid) to 6-hydroxyhexanoic acid (hydroxycaproic acid). Thus, in one aspect, the invention provides a method of producing 6-hydroxyhexanoic acid from the components present in mixed organic waste streams using an enzyme, such as a cytochrome P450, or an ω-hydroxylase or ω-oxygenase enzyme from the class EC 1.14.15.3. Although the use of a specific enzyme for a particular conversion is known (e.g., Coon, Biochemical & Biophysical Research Communications, 2005, 338:378-385), the inventors suprisingly discovered that these enzymes may be used to enzymatically convert components of mixed organic waste streams.

Additionally, 6-oxohexanoic acid can be produced indirectly from hexanoic acid or directly from 6-hydroxyhexanoic acid via the conversion of 6-hydroxyhexanoic acid to 6-oxohexanoic acid. In one aspect, the invention provides a method of producing 6-oxohexanoic acid from the components present in mixed organic waste streams, i.e., hexanoic acid or 6-hydroxyhexanoic acid, using an enzyme such as a fatty alcohol oxidase or an alcohol dehydrogenase from the class EC 1.1.1.-(Eurich et al., Applied & Environmental Microbiology, 2004, 70(8): 4872-4879).

These enzyme steps can be combined into a single method. Thus, in one aspect, the invention provides a method of producing 6-oxohexanoic acid from the mixed organic waste streams of cyclohexane oxidation, such as NVR and/or water wash, comprising the use of a combination of enzymes, such as (i) a cytochrome P450 or an ω-hydroxylase enzyme, and (ii) a fatty alcohol oxidase or an alcohol dehydrogenase.

iii) Converting Cyclic $C_6$ Components to 6-Oxohexanoic Acid

One step in the production of 6-oxohexanoic acid from cyclohexanol is the conversion of cyclohexanol to cyclohexanone. Thus, in one aspect, the invention provides a method of producing cyclohexanone from components of a mixed organic waste stream of cyclohexane oxidation, comprising the use of an enzyme such as an alcohol dehydrogenase or cyclohexanol dehydrogenase/ChnA from the class EC 1.1.1.-, for example EC 1.1.1.90, 1.1.1.245 and the like (Donoghue & Trudgill, Eur J. Bochem., 1975, 60:1-7).

After conversion of cyclohexanol to cyclohexanone, a subsequent step in the production of 6-oxohexanoic acid is the conversion of cyclohexanone to ϵ-caprolactone. Thus, in one aspect, the invention provides a method of producing ϵ-caprolactone from components of a mixed organic waste stream, comprising the use of an enzyme such as a Baeyer-Villiger monooxygenase, cyclohexanone monooxygenase/ChnB, e.g. 1.14.13.22, and the like (Kim et al., Biotechnol. Bioprocess Eng., 2008, 13:40-47).

Yet another step in the production of 6-oxohexanoic acid from cyclohexanol is the subsequent conversion of ϵ-caprolactone to 6-hydroxyhexanoic acid. Thus, in one aspect, the invention provides a method of producing 6-hydroxyhexanoic acid from the components of a mixed organic waste stream, comprising the use an enzyme such as a caprolactone lactonohydrolase, gluconolactonase/ChnC from the class EC 3.1.1.17, and the like (Cheng et al., Journal of Bacteriology, 2000, 182(17):4744-4751).

After conversion of ϵ-caprolactone to 6-hydroxyhexanoic acid, another step in the production of 6-oxohexanoic acid from cyclohexanol is the conversion of 6-hydroxyhexanoic acid to 6-oxohexanoic acid. Thus, in one aspect, the invention provides a method of producing 6-oxohexanoic acid from the components of a mixed organic waste stream, comprising the use of an enzyme such as a fatty alcohol oxidase or an alcohol dehydrogenase or ChnD. For example, the alcohol dehydrogenase may be selected from the class EC 1.1.1.2, such as 1.1.1.258 and the like (Cheng et al., Journal of Bacteriology, 2000, 182(17):4744-4751).

These enzyme steps can be combined into a single method. Thus, in one aspect, the invention provides a method of producing c-caprolactone from cyclohexanol and cyclohexanone molecules present in a mixed organic waste stream, comprising the use of a alcohol dehydrogenase and a Baeyer-Villiger monooxygenase. In another aspect, the invention provides a method of producing 6-hydroxyhexanoic acid from a mixed organic waste stream, comprising the use of a combination of enzymes such as an alcohol dehydrogenase, a Baeyer-Villiger monooxygenase and a caprolactone lactonohydrolase. In yet another aspect, the invention provides a method of producing 6-oxohexanoic acid from a mixed organic waste stream, comprising the use of a alcohol dehydrogenase, a Baeyer-Villiger monooxygenase, a caprolactone lactonohydrolase, and a fatty alcohol oxidase or an alcohol dehydrogenase. In a further aspect, the invention provides a method of producing 6-hydroxyhexanoic acid from 1,2-cyclohexanediol and cyclohexane-1,2-dione, which are present in the non-volatile residues and/or water wash of cyclohexane oxidation, comprising the use of a cyclohexane-1,2-diol dehydrogenase and a cyclohexane-1,2-dione acylhydrolase.

iv) Conversion of 6-Oxohexanoic Acid into Nylon Intermediates

As discussed herein, 6-oxohexanoic acid can be enzymatically converted into hexane-1,6-dioic acid (adipic acid) by the action of an aldehyde dehydrogenase. Thus, in one aspect, the invention provides a method of producing hexane-1,6-dioic acid (adipic acid) comprising producing 6-oxohexanoic acid using a biocatalyst, as set out supra, and further comprising enzymatic conversion of 6-oxohexanoic acid to hexane-1,6-dioic acid, using a biocatalyst such as an aldehyde dehydrogenase, for example from EC 1.2.1.4 and EC 1.2.1.63 and the like. The biocatalyst can be an isolated enzyme or a naturally occurring or non-naturally occurring host cell that expresses and secrets the enzyme.

As discussed herein, 6-oxohexanoic acid can be converted into 6-aminohexanoic acid by the action of an aminotransferase. Thus, in one aspect, the invention provides a method of producing 6-aminohexanoic acid comprising producing 6-oxohexanoic acid using a biocatalyst, as set out supra, and further comprising enzymatically converting 6-oxohexanoic acid to 6-aminohexanoic acid, using a biocatalyst such as a transaminase (EC 2.6.1.-) or a dehydrogenase, such as EC 1.4.1.- or the like. The biocatalyst can be an isolated enzyme or a naturally occurring or non-naturally occurring host cell that expresses and secrets the enzyme.

As discussed herein, 6-aminohexanoic acid can be converted to caprolactam by the action of an aminohydrolase. Thus, in one aspect, the invention provides a method of producing caprolactam using a biocatalyst to produce 6-aminohexanoic acid, as described supra, and further comprising enzymatic conversion of 6-aminohexanoic acid to caprolactam, using a biocatalyst such as an aminohydrolase, for example EC 3.5.2.- or the like. The biocatalyst can be an isolated enzyme or a naturally occurring or non-naturally occurring host cell that expresses and secrets the enzyme.

As discussed herein, 6-aminohexanoic acid can be converted to 6-aminohexanal by the action of an aldehyde dehydrogenase. Thus, in one aspect, the invention provides a method of producing 6-aminohexanal comprising using a biocatalyst to produce 6-aminohexanoic acid, as set out supra, and further comprising enzymatic conversion of 6-aminohexanoic acid to 6-aminohexanal, using a biocatalyst such as an aldehyde dehydrogenase. In another aspect, 6-aminocaproic acid is converted to 6-aminohexanal via multiple enzymatic steps, for example by forming 6-acetamidohexanoate, the corresponding acetyl-CoA or phosphate esters as intermediates. The biocatalyst can be an isolated enzyme or a naturally occurring or non-naturally occurring host cell that expresses and secrets the enzyme.

As discussed herein, 6-aminohexanal can be converted to hexamethylenediamine by the action of an aminotransferase or a amine oxidase. Thus, in one aspect, the invention provides a method of producing hexamethylenediamine comprising applying a biocatalyst to mixed organic waste streams to produce 6-aminohexanal, as set out supra, and further comprising enzymatic covnersion of 6-aminohexanal to hexamethylenediamine, using a biocatalyst such as an aminotransferase or amine oxidase. The biocatalyst can be an isolated enzyme or a naturally occurring or non-naturally occurring host cell that expresses and secrets the enzyme.

Methods to Increase the Relative Amount of Adipic Acid in Mixed Organic Waste Streams The present invention provides further means for improving the properties and composition of mixed organic waste streams by using a biocatalyst to reduce the complexity of a mixed organic waste stream, such as NVR, and increase the relative concentration of adipic acid in the stream, which facilitates recovery of adipic acid from the waste stream. In particular, the methods increase the relative concentration of adipic acid in a mixed organic waste stream, and reduce the amount of mono-acids and hydroxy-acids in the stream. Approximately 10% of adipic acid is lost in mixed organic waste streams as a result of oligomerization and/or diacids inseparably mixed with mono-acids and hydroxy-acids. However, the inventors have discovered that applying at least one biocatalyst to the organic waste stream can improve recovery of adipic acid.

In particular, the biocatalyst can hydrolyze at least a portion of the oligomeric esters into monomers, hydrolyze at least a portion of ε-caprolactone to 8-hydroxy-caproic acid, oxidize at least a portion of caproic acid, 6-hydroxycaproic acid, and 6-oxocaproic acid to adipic acid, and/or convert at least a portion of the cyclic C6 components of the waste stream to adipic acid.

The hydrolase capable of hydrolyzing oligomeric esters into monomers may be an isolated or immobilized enzyme. Alternatively, the hydrolase may be an endogenous or heterologous hydrolase secreted by a naturally occurring or non-naturally occurring host cell during fermentation and bioconversion.

These methods can reduce the complexity of NVR, and increase the relative concentration of adipic acid within the NVR waste stream, which facilitates recovery of adipic acid from NVR, by converting caproic acid, hydroxy-caproic acid, and cyclic C6 compounds (e.g., K and A) to adipic acid. A biocatalyst that utilizes less desirable components of NVR, e.g., C3-C5, for growth may further reduce the complexity of the waste stream. For example, a preferred method includes hydrolyzing the oligomeric esters present in the waste stream to monomers; converting the mono-acids and hydroxy-acids into diacids; removing C4 and C5 components from the mixture; catabolizing at least a portion of C3, C4, and C5 components present in said mixed organic waste stream; and/or catabolizing C6 components at a lower rate than C3, C4, and C5 components in the mixed organic waste stream. The biocatalyst may also be applied to COP acid and water wash waste streams, in addition to NVR, to perform a variety of enzymatic conversions, e.g., hydrolyzing lactones into hydroxy-acids and/or oxidizing linear C4-C6 monoacids and hydroxy-acids into diacids.

In one aspect, these methods can be used to enrich the relative of concentration of adipic acid in the mixed organic waste stream during fermentation. Then, the treated mixture can be removed from the fermenter and returned to the crystallization process, where adipic acid will crystallize from the mixture as a result of sufficient enrichment during fermentation. With such methods, an existing facility for cycloalkane oxidation can be modified to allow treatment of the waste stream with a biocatalyst that enriches adipic acid. There is no need to build an entirely new facility for such enrichment, which saves a significant amount of time and money.

Preferably, the methods for increasing the relative concentration of adipic acid and reducing the amount of mono-acids and hydroxy-acids is performed using a non-naturally occurring host cell as the biocatalyst, because these methods require two enzymatic pathways that are believed to not naturally co-exist in a host cell. In one aspect, the beta-oxidation pathway present in the biocatalyst may be impaired so that adipic acid is not degraded. For example, the host cell may be *Y. lipolytica* having the PDX genes knocked out, i.e., inactivated, such that the host cell beta-oxidation pathway is impaired, resulting in an accumulation of adipic acid.

Methods to Convert C6 Components and Precursors of Mixed Organic Waste Streams to α,ω-Difunctional C6 Alkanes The present invention provides further means for improving the properties and composition of mixed organic waste streams by using a biocatalyst to convert C6 components and precursors present in the waste stream to α,ω-difunctional C6 alkanes.

Figure 2:
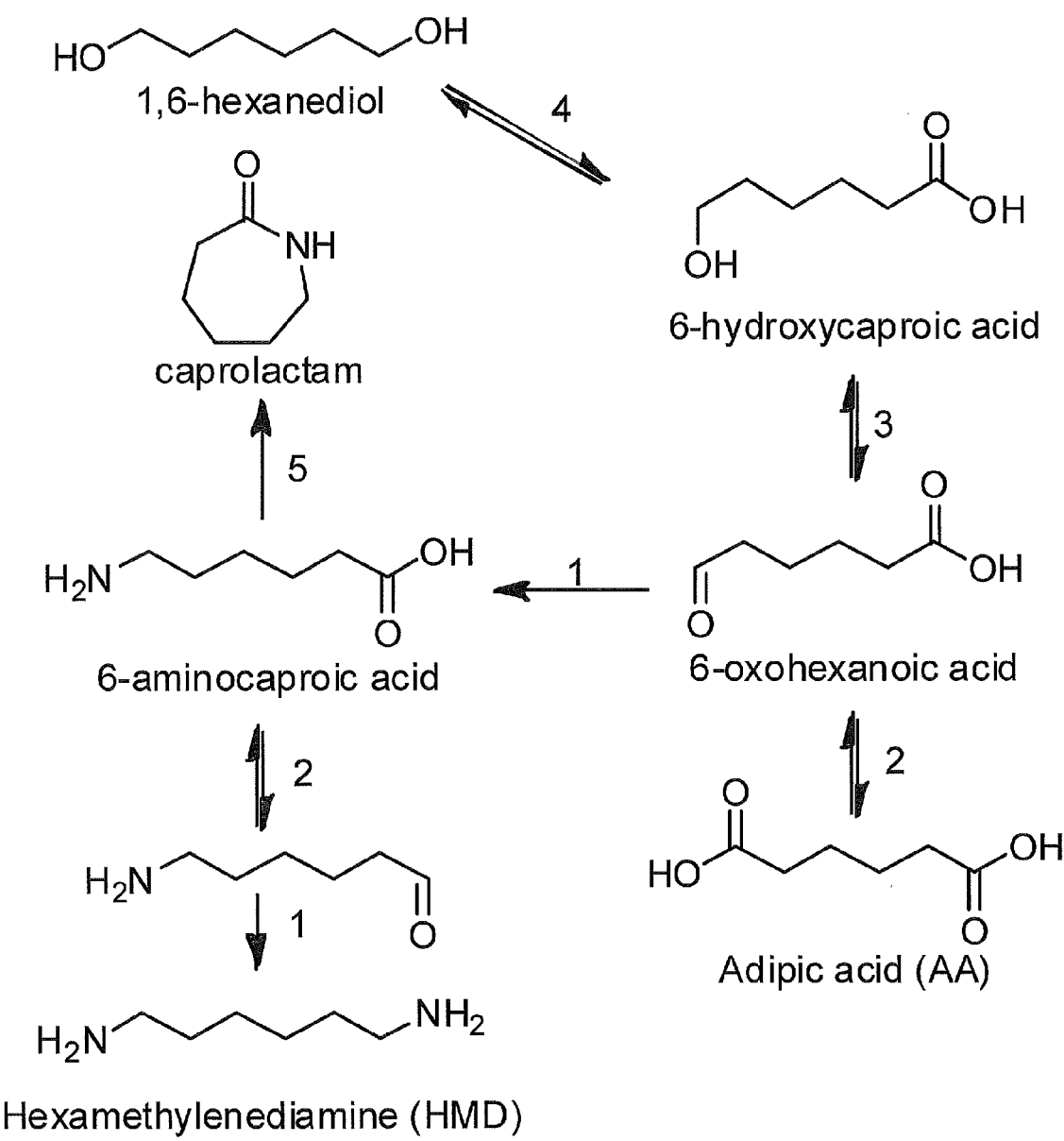
FIG. 2 is a schematic illustration which shows exemplary enzyme conversions for the conversion of 6-hydroxycaproic acid to 1,6-hexanediol and of 6-oxohexanoic acid to 6-aminohexanoic acid, which is then converted to caprolactam, or to hexane-1,6-diamine (hexamethylenediamine) via 6-aminohexanal. 1:1-aminotransferase EC 2.6.1.191, also aminotransferase from *Bacillus weihenstephanensis* KBAB4, *Pseudomonas aeruginosa* gi99510722; 2: Carboxylate reductase EC1.2.99.6 or aldehyde dehydrogenase EC 1.2.1.3/EC 1.2.1.31; 3: 6-hydroxyhexanoate dehydrogenase EC 1.1.1.258; 4: alcohol/aldehyde dehydrogenase EC 1.2.1.10; 5: amidohydrolase (EC 3.5.2.-), such as EC 3.5.2.11.

Enzymatic conversion of 6-hydroxycaproic acid to 1,6-hexanediol, adipic acid to 6-oxohexanoic acid, and 6-oxohexanoic acid to 6-aminocaproic acid is mediated by a series of different enzymes (see FIG. 2). In particular, 6-oxohexnaoic acid is converted into 6-aminocaproic acid by aminotransferase EC 2.6.1.19 (Enzymatic studies on the metabolism of beta-alanine disclosed in (Hayaishi et al. 1961 J. Biol. Chem. 236, p. 781-790) as well as aminotransferases disclosed in WO2009/113855 & WO2011/031147, herein incorporated by reference in their entirety), which show preparation of 6-aminoacproic acid from 5-formyl valeric acid and preparation of a compound comprising an amine group from an alpha-keto acid, respectively, using such enzymes. Similarly, 6-aminohexanal may be converted into hexamethylenediamine using these aminotransferases. 6-oxohexanoic acid may be converted into adipic acid by carboxylate reductase EC1.2.99.6 or aldehyde dehydrogenase EC 1.2.1.3 or EC 1.2.1.31. 6-aminocaproic acid in turn can be converted to hexamethylenediamine or caprolactam. In one aspect, 6-aminocaproic acid may be converted into 6-aminohexanal using these carboxylate reductases or aldehyde dehydrogenases. In another aspect, 6-oxohexanoic acid may be converted into 1,6-hexanediol via conversion into 6-hydroxycaproic acid by 6-hydroxyhexanoate dehydrogenase EC 1.1.1.258, which may be subsequently converted to 1,6-hexanediol by alcohol/aldehyde dehydrogenase EC 1.2.1.10. Additionally, 6-aminocaproic acid may be converted into caprolactam by an amidohydrolase (EC 3.5.2.-), such as EC 3.5.2.11.

In one aspect, the mixed organic waste stream is treated with a non-naturally occurring host cell capable of hydrolyzing at least a portion of the oligomeric esters into monomers; oxidising at least a portion of caproic acid to 6-hydroxycaproic acid; converting at least a portion of the cyclic C6 components to 6-hydroxycaproic acid or 6-oxocaproic acid; catabolizing at least a portion of C3, C4 and C5 components present in the mixed organic waste stream; and/or catabolizing C6 components at a lower rate than C3, C4 and C5 components in the mixed organic waste stream.

The hydrolase capable of hydrolyzing oligomeric esters into monomers may be an isolated or immobilized enzyme. Alternatively, the hydrolase may be an endogenous or heterologous hydrolase that is secreted by a naturally occurring or non-naturally occurring host cell during fermentation and bioconversion.

In addition, the host cell is capable of expressing at least one biosynthetic pathway enzyme to convert adipic acid, 6-hydroxycaproic acid or 6-oxohexanoic acid to 1,6-hexanediol, 6-aminocaproic acid, 8-caprolactam, or hexamethylenediamine.

In another aspect, the present invention provides methods for using microorganisms as host cell biocatalysts to biologically synthesize the enzymatic conversion of NVR components to difunctional alkanes. The use of microorganisms for biological production of adipic acid and difunctional alkanes from sources other than mixed organic waste streams has previously been demonstrated. See, WO2009/151728 and WO2010/068944, herein incorporated by reference in their entirety. The present invention provides applying a non-naturally occurring host cell, e.g., modified to contain a heterologous enzyme required for conversion of cyclic C6 components of NVR to 6-hydroxycaproic acid or 6-oxocaproic acid.

In another aspect, the non-naturally occurring host cell is further modified to produce 1,6-hexanediol. Optionally, such a 1,6-hexanediol producing host cell may also express particular enzymes involved in the production of 1,6-hexanediol. Preferably, the host cell expresses an aldehyde dehydrogenase, which catalyzes the conversion of 6-oxohexanoic acid to 6-hydroxycaproic acid, and a alcohol dehydrogenase, which catalyzes the conversion of 6-hydroxycaproic acid to 1,6-hexanediol.

In yet another aspect, the non-naturally occurring host cell further genetically modified to produce 6-aminocaproic acid. Optionally, such a 6-aminocaproic acid producing host cell may also express particular enzymes involved in the production of 6-aminocaproic acid. Preferably, the host cell expresses an aminotransferase able to convert 6-oxohexanoic acid to 6-aminocaproic acid. In one aspect, the host cell that expresses the aminotransferase is further genetically modified to express an amidohydrolase able to convert 6-aminocaproic acid to ε-caprolactam. In another aspect, the host cell that expresses the aminotransferase is further genetically modified to produce hexamethylenediamine via an aldehyde dehydrogenase, which is able to convert 6-aminocaproic acid to 6-aminohexanal, and a 1-aminotransferase, which is able to convert 6-aminohexanal to hexamethylenediamine.

Conversion and/or Degradation of C3, C-4 and C-5 Species

C-4 and C-5 monoacids (butyric acid and pentanoic acid) and/or hydroxy-acids (4-hydroxybutyric acid and 5-hydroxypentanoic acid) present in the NVR or water wash from cyclohexane oxidation are optionally converted via the same pathway consisting of a ω-hydroxylase, a alcohol dehydrogenase and an aldehyde dehydrogenase described for caproic acid and hydroxycaproic acid. Butyric acid and pentanoic acid are converted to the corresponding diacids, namely succinic acid and glutaric acid. This conversion reduces the complexity of the mixture of chemical species in the NVR or water wash from cyclohexane oxidation to a mixture predominantly consisting of C6, C5 and C4 diacids. By reducing the number of chemical species in the mixture, the resulting diacid mixture is recovered more easily from the fermentation broth for commercial application as diacids, or is optionally esterified by known methods to the corresponding dibasic esters, which has commercial use as a dibasic ester mixture, or is optionally separated into C6, C5 and C4 dibasic esters by known methods. Some or all of the C4 and C5 species present in the NVR or water wash from cyclohexane oxidation such as butyric acid, pentanoic acid, succinic acid, glutaric acid, 4-hydroxybutyric acid, and 5-hydroxypentanoic acid iscatabolized via β-oxidation to acetyl-CoA via the TCA cycle, thereby reducing the complexity of the chemical species and facilitating easier recovery of adipic acid, aminocaproic acid, caprolactam or hexamethylenediamine, while serving as a carbon source for biomass production and thus reducing the amount of fermentable carbon source that is required for biomass production. Thus, the invention provides a method of reducing the concentration of C-4 and C-5 species by catabolizing at least a portion of the C-4 and C-5 carbon species C3 species in the NVR or water wash from cyclohexane oxidation. Genetic engineering of the host can be performed to minimize the loss of caproic acid and/or adipic acid, which are catabolized via β-oxidation or via the TCA cycle.

To reduce degradation of caproic acid or adipic acid via the β-oxidation pathway of the host organism and thus improve the amount of useful products that can be recovered from the fermentation broth, the gene encoding enzymes acting on these substrates or their CoA esters can be knocked out or mutated to reduce its activity or change the substrate specificity of the enzymes encoded by these genes. To prevent or reduce activation of caproic acid or adipic acid to their corresponding CoA esters, it is useful to disrupt or mutate genes of the host strain encoding CoA ligases or CoA transferases acting on adipic acid or caproic acid if present in the host strain, belonging to the class EC 6.2.1.-, such as EC 6.2.1.23 acting on dicarboxylic acids with chain lengths of 5 to 16 carbons, and the like. Alternatively, it is also advantageous to prevent the activated CoA esters from entering the β-oxidation pathway by disrupting or mutating genes present in the host organism that encode acyl-CoA oxidases or acyl-CoA dehydrogenases acting on caproyl-CoA or adipoyl-CoA, such as EC 1.3.3.6 or EC 1.3.99.- and the like.

Non-Naturally Occurring Enzymes

In some embodiments, the enzymes used to perform conversions in the methods described herein are non-naturally occurring, i.e., the DNA encoding the enzyme has been mutated from the wildtype sequence to improve one or more of the enzyme's properties. Methods for mutagenesis of genes and protein engineering are well known in the art. Random and/or combinatorial mutagenic approaches may alternatively or additionally be used for the creation of libraries of mutations, including approaches such as DNA shuffling, STEP and error prone PCR, molecular evolution and mutator strains. A non-limiting list of mutagenic changes includes deletions, insertions, substitutions, rearrangements, point mutations, and suppressor mutations.

The products of the mutagenic methods should then be screened for the desired activity. Thus, in some embodiments, the enzyme used for hydrolysis of oligomeric ester components of a mixed organic waste steam or other enzymatic conversion, e.g., oxidation, is derived from an enzyme as described supra, e.g., in section 1(i)-(iv). As used herein, the term "derived" means that the enzyme contains one or more amino acid changes compared to the amino acid sequence of the wildtype enzyme, wherein the one or more changes includes deletions, insertions, substitutions, rearrangements, point mutations. The skilled person would understand that the EC classification system discussed in relation to the enzymes as described supra is highly specific, and depends on the specific substrates catalyzed by an enzyme. Accordingly, an enzyme that is derived from one of the enzymes as described may be classified in a different EC category than the wildtype enzyme.

In one aspect, the non-naturally occurring enzyme is derived from one or more of a P450 cytochrome oxidase, an ω-hydroxylase, ω-oxygenase enzyme or alkane-1-monooxygenase from the class EC 1.14.15.3; a fatty alcohol oxidase; an alcohol dehydrogenase from the class EC 1.1.1; a Baeyer-Villiger monooxygenase; a caprolactone lactonohydrolase; a fatty alcohol oxidase; an alcohol dehydrogenase; a cyclohexane-1,2-diol dehydrogenase; a cyclohexane-1,2-dione acylhydrolase; a carboxylesterases from the α,β-hydrolase fold family (EC 3.1.1.-); or combinations thereof.

In another aspect, the non-naturally occurring enzyme is derived from one or more of cyclohexanol dehydrogenase/ChnA from the class EC 1.1.1.245; cyclohexanone monooxygenase/ChnB from the class EC 1.14.13.22; gluconolactonase/ChnC from the class EC 3.1.1.17; ChnD from the class EC 1.1.1.2; cyclohexane-1,2-diol dehydrogenase from EC 1.1.1.174; cyclohexane-1,2-dione acylhydrolases EC 3.7.1.10 or EC 3.7.1.11; lipases (EC 3.1.1.3); esterases (EC 3.1.1.1); cutinases (EC3.1.1.74); polyhydroxyalkanoate (PHA) depolymerases (EC 3.1.1.75 & EC 3.1.1.76); 1,4-lactonases (EC 3.1.1.25); gluconolactonases (EC 3.1.1.17); laccases (EC 1.10.3.2); or combinations thereof.

The enzymes used in the present methods may be improved with respect to a number of parameters. (Dalby, P. A (2003). Optimising enzyme function by directed evolution. Current Opinion in Structural Biology, 13, 500-505). The enzyme may be improved over the wildtype enzyme with regard to the rate of reaction, so that the enzyme is able to convert more substrate to product in a defined period of time. This is advantageous because it decreases the time taken to perform the method of the invention. In an alternative, the enzyme may be improved over the wildtype enzyme with regard to the solvent stability of the enzyme in the presence of organic solvents. This is advantageous because in some embodiments, the method of the invention may be performed, in whole or in part, in a biphasic system, or a mixed solvent system (for example a mixed water/cyclohexanol and cyclohexanone system). In a further alternative, enzyme may be improved over the wildtype enzyme with regard to its activity at elevated temperatures. This is advantageous because it means that the method may be performed, in whole or in part, at temperatures which increase the rate of reaction (but which would have inactivated the wildtype enzyme).

In a further alternative, the enzyme is engineered to reduce product inhibition and or substrate inhibition. This advantageously permits higher concentrations of the product and or substrate to be present in the reaction. In a further alternative the substrate reactivity of the enzyme may be altered. This means that the engineered enzyme is capable of reacting with a substrate that the wildtype enzyme cannot. Such enzymes are typically employed where a wildtype enzyme that is capable of performing the desired reaction is not known, or is not suitable. The substrate specificity may also be changed by engineering the enzyme so that it is able to accept and react with a substrate that the wildtype enzyme cannot accept. In yet a further alternative, the enzyme is engineered to shift its pH optimum to a more acidic or a more alkaline pH. This means that the enzyme can be employed at a pH suitable for the process requirements.

In a further alternative, the gene encoding the enzyme used in the claims methods is codon optimized. Thus, the DNA sequence encoding the enzyme is altered so that the codon for each amino acid uses the most prevalent tRNA for that amino acid in the host cell in which the enzyme is to be expressed.

In another alternative, the polypeptide may be engineered to include a tag for easy purification (e.g., His-tag, GST-tag, Flag tag). In another alternative, the polypeptide may be engineered to include a localization sequence to target the polypeptide to a specific cellular location, e.g., an organelle, extracellularly, cell membranes or the periplasm.

These various alternatives, e.g., codon optimization, modification to include a localization sequence and/or purification tag, and modification to alter activity at temperature, substrate inhibition, etc., may be combined in a single engineered enzyme.

Combinations of Enzymes

In any of the methods or compositions described herein, multiple types of enzymes may be present. For example, any combination of, e.g., 2, 3, 4, 5, 6, 7, 8, 9, 10, 11 or 12, the enzyme types discussed herein may be used. Suitable enzymes include, but are not limited to: Cytochrome P450 or ω-hydroxylase (omega-hydroxylase), a fatty acid oxidase or primary alcohol dehydrogenase, an aldehyde dehydrogenase or ChnE, a alcohol dehydrogenase or ChnA, a gluconolactonase or Baeyer Villiger monooxygenase, a cyclohexane-1,2-dione acylhydrolase, a cyclohexane-1,2-diol dehydrogenase, a carboxylesterase or esterase or lipase or polyhydroxyalkanoate depolymerase, a transaminase or 6-aminocaproate dehydrogenase, an amidohydrolase, an aldehyde dehydrogenase, and a diamine oxidase or diamine transaminase.

Host Cell Biocatalysts

The present invention relates to the use of biocatalysts to enzymatically convert the compounds found in mixed organic waste streams, e.g., the non-volatile residues or water wash waste streams of cycloalkane oxidation, such as cyclohexane oxidation, to compounds which are useful in the synthesis of nylons.

The biocatalysts that are used in the methods of the invention may be introduced into the reaction in a variety of forms. In one aspect, each enzyme is in the same form. In another aspect, the enzymes are provided in different forms.

Host cells biocatalysts that express one or more enzymes useful in the claimed methods may be used as the biocatalyst. The host cells that are used typically possess a number of properties: they may be easily genetically modified, are tolerant of the conditions used in the method of the invention, and grow to cells densities which are industrially useful. Optionally, the whole cell may be a single celled microorganism, or may be a cell of a cell line. The whole cell may be of a wildtype genotype. In this instance, the enzyme that is used to catalyze one or more steps in the claimed method is naturally present in the whole cell and is expressed at a level that has industrial use in the methods of the invention. In an alternative, the host organism has been genetically modified to express the enzyme at a level that has industrial use in the methods of the invention. The enzyme may be sourced from the cell in which it is expressed. In an alternative, the enzyme is sourced from a different strain or species of cell.

In one aspect, the whole cell is a prokaryote. In another alternative it is a eukaryote. Typically, single celled microorganisms are used.

The term prokaryotic cell includes gram positive and gram negative bacteria. Examples of gram negative bacteria which may be used with the methods of the invention are *Escherichia coli*, *Rhodopseudomonas palustris*, sphingomonads, pseudomonads, and other bacteria belonging to *Salmonella*, *Burkholderia*, *Moraxella*, *Acaligenes*, *Psychrobacter*, *Thermotoga*, *Acinetobacteria*, *Rhodobacter*, *Azoarcus*, and *Rhodospirillum* genera. Examples of gram positive bacteria which may be used with the methods of the invention are streptococci, lactobacilli, and other bacteria belonging to *Nocardia*, *Bacillus*, *Rhodococcus*, *Chlostridium*, *Streptomyces*, and *Arthobacter* genera.

Eukaryotic host cells include those from yeast and other fungi. Examples of eukaryotic host cells which may be used with the methods of the invention are from *Yarrowia lipolytica*, *Candida* genera such as *Candida tropicalis*, *C. albicans*, *C. cloacae*, *C. guillermondii*, *C. intermedia*, *C. maltosa*, *C. parapsilosis*, *C. zeylenoides*, yeasts belonging to the *Rhodotorula*, *Rhizopus*, *Trichosporon*, and *Lipomyces* genera, and other fungi belonging to *Aspergillus*, *Exophiala*, *Mucor*, *Trichoderma*, *Cladosporium*, *Phanerochaete*, *Cladophialophora*, *Paecilomyces*, *Scedosporium*, and *Ophiostoma* genera.

The host cell biocatalyst contain an additional enzymatic pathway, either naturally or via genetic modification, that performs an enzymatic conversion that is particularly useful in conjunction with other claimed enzymatic conversions that improve the properties and compositions of the mixed organic waste streams. For example, a naturally occurring host cell biocatalyst may contain two enzymatic pathways that are required for increasing the relative amount of adipic acid in a mixed organic waste stream by oxidizing at least a portion of the linear C4-C6 monoacids, hydroxy-acids, and oxo-acids present in the stream to their corresponding diacids. Such a process requires the host cell cytochrome p450 pathway as well as additional optional enzymes. The presence of additional endogenous or heterologous enzymatic pathways in a host cell is particularly useful for increasing the relative amount of diacids in a mixed organic waste stream, increasing the relative concentration of adipic acid and reducing the amount of monoacids and hydroxyacids in the waste stream, and/or converting C6 components and precursors present in the waste stream to α,ω difunctional alkanes.

In one aspect, the naturally or non-naturally occurring host cell that performs an enzymatic conversion of C4-C6 or cyclic C6 monoacids, hydroxyacids, or oxo-acids to diacids via the oxo-acid, has an endogenous or heterologous omega oxidation pathway that is capable of one of more of the following conversions:

conversion of butyric acid, valeric acid, and/or adipic acid to their corresponding diacid (i.e., succinic acid, glutaric acid, and/or adipic acid, respectively);

conversion of butyric acid, valeric acid, and/or adipic acid to their corresponding hydroxy-acid (i.e., 4-hydroxybutyric acid, 5-hydroxyvaleric acid, and/or 6-hydroxycaproic acid, respectively);

conversion of 4-hydroxybutyric acid, 5-hydroxyvaleric acid, and/or 6-hydroxycaproic acid to their corresponding oxo-acid (i.e., 4-oxobutanoic acid, 5-oxopentanoic acid, and/or 6-oxohexanoic acid, respectively); or conversion of 4-oxobutanoic acid, 5-oxopentanoic acid, and/or 6-oxohexanoic acid to the corresponding diacid (i.e., succinic acid, glutaric acid, and/or adipic acid, respectively).

A host cell with an endogenous of heterologous omega-oxidation pathway capable of converting aliphatic fatty acids to diacids via hydroxyl-acids and oxo-acids may be an n-alkane utilizing yeast or bacterium. Exemplary the n-alkane utilizing yeast include *Yarrowia lipolytica, Candida tropicalis, C. albicans, C. cloacae, C. guillermondii, C. intermedia, C. maltosa, C. parapsilosis, C. zeylenoides*, or combinations thereof, or yeasts of the *Rhodotorula, Rhizopus, Trichosporon, Debaryomyces and Lipomyces* genera or combinations thereof. Exemplary n-alkane utilizing bacteria include *Pseudomonas fluorescens, P. putida, P. aeroginosa, P. oleoverans, Marinobacter hydrocarbonoclasticus, Acinetobacter* sp. such as *A. venetianus, Oleiphilus messinensis, Arthrobacter viscosus, Cupriavidus metallidurans, Rhodococcus* sp. such as *R. rhodochrous* and *R. erythropolis, Sphingomona spaucimobilis, Burkholderia cepacia, Delftia acidovorans, Alcanivorax diesolei* or combinations thereof.

In another aspect, the naturally or non-naturally occurring host cell that enzymatically converts at least a portion of cyclic C6 components present in the mixed organic waste stream into 6-hydroxycaproic acid, 6-oxohexanoic acid, or adipic acid has an endogenous or heterologous pathway that is capable of (i) converting cyclohexanol to 6-oxohexanoic acid, (ii) converting 1,2-cyclohexanediol to 6-oxohexanoic acid, and/or (iii) converting 6-oxohexanoic acid to adipic acid.

In converting cyclohexanol to 6-oxohexanoic acid, the host cell catalyzes conversion of cyclohexanol to cyclohexanone; conversion of cyclohexanone to 6-caprolactone; conversion of c-caprolactone to 6-hydroxyhexanoic acid; and/or conversion of 6-hydroxyhexanoic acid to 6-oxohexanoic acid.

In converting 1,2-cyclohexanediol to 6-oxohexanoic acid, the host cell catalyzes conversion of cyclohexane-1,2-diol to cyclohexane-1,2-dione, or conversion of cyclohexane-1,2-dione to 6-oxohexanoic acid.

Modification of Host Cell Biocatalysts

The biocatalysts used in the methods of the invention may be unmodified host cells of the species in which the enzyme naturally occurs. However, it may be necessary to genetically modify the host cell to produce an engineered cell. As used herein, an engineered cell means a cell that has been manipulated so that its genome has been altered from the genome of a wildtype cell. The alteration of the genome includes the introduction and deletion of plasmids. In one aspect, the genetic modification is the introduction of a nucleic acid into the genome of the cell. See, FIG. 3. The nucleic acid introduced into the cell may comprise a nucleic acid sequence from another species or organism, for example a DNA sequence that is not present in the wildtype genome of the whole cell. In other instances, the introduced DNA sequence may be a further copy of a DNA sequence in the genome of the whole cell. In some alternatives, the genetic modification is the deletion of DNA sequence from the genome of the whole cell. In another aspect, the genetic modification is the modification of the genome of the cell.

In one alternative, the engineered cell is a prokaryote. In another alternative it is a eukaryote. Typically, single celled microorganisms are used.

The term prokaryotic cell includes gram positive and gram negative bacteria. Examples of gram negative bacteria which are suitable for use as engineered cells of the invention include *Escherichia coli, Rhodopseudomonas palustris, sphingomonads, pseudomonads*, and other bacteria belonging to *Salmonella, Burkholderia, Moraxella, Acaligenes, Psychrobacter, Thermotoga, Acinetobacteria, Rhodobacter, Azoarcus*, and *Rhodospirillum* genera. Examples of gram positive bacteria which are suitable for use as engineered cells of the invention include streptococci, lactobacilli, and other bacteria belonging to *Nocardia, Bacillus, Rhodococcus, Chlostridium, Streptomyces*, and *Arthobacter* genera.

Typically eukaryotic engineered cells are yeasts and other fungi. Non-limiting examples of eukaryotic engineered cells include *Yarrowia lipolytica, Candida* genera such as *Candida tropicalis, C. albicans, C. cloacae, C. guillermondii, C. intermedia, C. maltosa, C. parapsilosis, C. zeylenoides*, yeasts belonging to the *Rhodotorula, Rhizopus, Trichosporon*, and *Lipomyces* genera, and other fungi belonging to *Aspergillus, Exophiala, Mucor, Trichoderma, Cladosporium, Phanerochaete, Cladophialophora, Paecilomyces, Scedosporium*, and *Ophiostoma* genera. In one alternative, the host cell is *Yarrowia lipolytica*.

i) Introduced Nucleic Acid Sequences

The nucleic acids introduced into the cell may comprise one or more of a number of elements. Typically, one of the elements will be a gene encoding an enzyme that is used in the method of the invention, e.g. a cytochrome P450, a ω-hydroxylase (omega-hydroxylase), a fatty acid oxidase, a primary alcohol dehydrogenase, a ketoreductase, a Baeyer-Villiger monooxygenase, a caprolactone hydroxylase, a dione hydrolase, an esterase/lipase, an aldehyde dehydrogenase, an aminotransferase, an amidohydrolase, or an engineered version of any of these types of enzyme. In some alternatives, the nucleic acid encodes a protein that is not an enzyme that functions in the method of the invention, such as a chaperone or a protein that acts as an activator or repressor of a gene.

Typically, the nucleic acid will be designed so that the polypeptide is operably linked to a promoter. As used herein, the term "operably linked," as used herein, means that the element is placed in position such that it is able to direct the expression of the polynucleotide or polypeptide. This may be arranged by operably linking a promoter element to the one or more polypeptides that are being expressed on the introduced nucleic acid sequence, so establishing the operable link prior to the introduction of the nucleic acid into the cell. In order to ensure the operable linkage of a promoter to the one or more enzymes, the promoter should be placed to the 5' of the enzyme and no in frame termination codons should be present in the sequence between the promoter and the enzyme. Alternatively, the nucleic acid may be designed such that when it is introduced, a gene sequence in the nucleic acid is placed in the host cell's genome in a manner so that it is operably linked to a promoter already present in the host cell's genome and therefore the enzyme may be expressed from that promoter.

ii) Expression of Multiple Enzymes in a Whole Cell

In some embodiments, a single strain of whole cell is used to express more than one of the enzymes used in the methods of the invention. In this instance, the multiple enzymes may be encoded by the same introduced nucleic acid. In an alternative, the enzymes may be encoded on separate introduced nucleic acid fragments. The enzymes may all be expressed from a single promoter (for example by arranging the enzymes in the of an operon). In an alternative, the enzymes may be expressed from multiple separate promoters. In some instances, the multiple separate promoters may be induced by the same chemical (for example, each of the multiple enzymes may be expressed from the yeast GAL promoter, thus meaning that each gene is inducible with galactose). Other suitable promoters are known in the art. In an alternative, each of the genes encoding an enzyme used in the method of the invention is under the control of a different promoter. Thus, different enzymes can be introduced individually through the use of different inducing compounds. In another alternative, an intermediate approach is used, wherein a number of enzymes are under the control of the same promoter, and a number of enzymes are under the control of different promoters. This alternative may be particularly advantageous when numerous enzyme pathways have been generated in a whole cell and it is desirous to control each member of a pathway in concert with the other pathway members, but to control each pathway separately.

iii) Chaperone Systems

When a cell has been engineered to express a protein under non-natural conditions (for example, when a protein that is native to a species is expressed at levels above the natural level, or in an alternative, when a protein from a different species is expressed in a host cell) in some instances that protein will not be expressed in an active form. Instead it may fold incorrectly, and accumulate as a non-functional "inclusion body" aggregates. In this instance, the cells used to express the protein may be subjected to genetic modification to further express chaperone proteins which are able either to prevent the mis-folding of the protein, or are able to refold it from the aggregated state.

The inclusion of such chaperone proteins is advantageous because it increases the quantity of active protein per cell, and therefore increases the overall efficiency of the method of the invention. The expressed chaperone may be a chaperone protein of the host cell. In an alternative, the chaperone may be from the same species/strain as the protein. Typical chaperone proteins for expression include members of the GroEL/GroES family, and members of the DnaJ/DnaK/GrpE family. Homologs of the archetypal K coli GroEL/GroES and DnaJ/DnaK/GrpE proteins have been identified in other prokaryotic species, and eukaryotic homologs are also known (GroEL and GroES correspond to the eukaryotic proteins Hsp60 and Hsp10, and DnaJ, DnaK and GrpE correspond to the eukaryotic proteins Hsp70, Hsp40 and Hsp24, respectively). These proteins have been identified in a number of species of yeast (for example, *Saccharomyces cerevisiae*). The choice of appropriate chaperone proteins for coexpression with an enzyme used in the method of the invention will be evident to the skilled person following the teachings herein.

Metabolic Engineering of Whole Cells

Metabolic engineering is the process of optimizing the parameters in a whole cell in order to increase the ability of a cell to produce a compound. The whole cells used in the method of the present invention optionally have been engineered to optimize the output of diacids, or alternatively adipic acid or 6-oxohexanoic acid, 1,6-hexanedoil, 6-aminohexanoic acid, caprolactam, and hexamethylenediamine.

Metabolic engineering to increase the ability of a cell to produce a compound is principally performed via two avenues. The first is to optimize the enzymes in the pathway producing the desired product from the starting material. It is possible to determine the concentration of each intermediate in the pathway using techniques known to the skilled person (for example, two dimensional electrophoresis, the use of isotopically labelled precursors, and nuclear magnetic resonance (NMR) spectroscopy), and therefore determine which of the enzyme conversions is the rate limiting step—that is to say which step in the reaction scheme is the slowest. This can be determined by observing a build up of an intermediate, which indicates that the enzyme acting upon this intermediate is limiting the overall rate of conversion. In this instance, the rate at which this intermediate is reacted should therefore be increased.

As an example, in a method of the present invention, conversion may be the production of hexane-1,6-dioic acid from hexanoic acid. This conversion (as shown in FIG. 2) requires the use of three enzymes: a cytochrome P450 to convert hexanoic acid to 6-hydroxyhexanoic acid, an alcohol dehydrogenase to convert 6-hydroxyhexanoic acid to 6-oxohexanoic acid and an aldehyde dehydrogenase to the 6-oxohexanoic acid to hexane-1,6-dioic acid.

If the rate of production of 6-hydroxyhexanoic acid from hexanoic acid by the cytochrome P450 is less than the rate at which the subsequent conversions in the pathway are be performed (i.e. by the alcohol dehydrogenase and the aldehyde dehydrogenase), then the rate of production of the 6-hydroxyhexanoic acid should be increased. This can be performed by a number of means. Firstly, the expression level of the cytochrome P450 may be increased. Optionally, this may be achieved by placing the gene encoding the enzyme under the control of a strong promoter, e.g., the T7 promoter if the enzyme is being expressed in *E. coli* or the TEF promoter if the enzyme is being expressed in yeast.

The second option is to increase the number of copies of the gene encoding the enzyme that are present in cell, for instance by placing the gene on a multicopy plasmid, or by incorporating multiple copies of the gene into the chromosome of the host cell (these copies may be incorporated at the same location in the chromosome or in different locations in the chromosome).

Thirdly, the cytochrome P450 enzyme may be subjected to mutagenesis to evolve the enzyme to react at a faster rate or to codon optimize the enzyme to increase its expression. This description is purely exemplary, and the same process may be performed to optimize the expression of the other enzymes which are used in the method of the invention (i.e. a ω-hydroxylase (omega-hydroxylase), a fatty acid oxidase, a primary alcohol dehydrogenase, a ketoreductase, a Baeyer-Villiger monooxygenase, a caprolactone hydroxylase, a dione hydrolase, an esterase/lipase, an aldehyde dehydrogenase, an aminotransferase, an amidohydrolase or an engineered version of any of these types of enzyme.

The production of hexan-1,6-dioic acid can also be increased by inactivating or reducing the activity of any enzymes which are capable of diverting the substrate, any of the intermediates, or the product into a metabolic pathway other than that which is the aim of the method. In the exemplified pathway discussed supra, both hexanoic acid and hexane-1,6-dioic acid may be acted upon by acyl-CoA ligase and/or CoA transferase enzymes. Once ligated to CoA, the compound may then be fed into the β-oxidation (beta-oxidation) pathways of the cell, resulting in the breakdown of that compound. Thus in some embodiments, the whole cell that is used in the methods of the invention has been engineered to delete one of more acyl-CoA ligase and/or CoA transferase enzymes that are capable of ligate CoA to hexanoic acid, 6-hydroxyhexanoic acid, 6-oxohexanoic acid or hexane-1,6-dioic acid.

In an alternative, the acyl-CoA ligase and/or CoA transferase enzyme is not deleted, but is instead engineered so that it can no longer act on the substrate, intermediates, or product (i.e. it can no longer accept linear $C_6$ molecules as substrates), but retains any ability to ligate CoA to other molecules, typically $C_3$-$C_5$ chains.

In one aspect, high yields of C6 components is achieved by decreasing the rate of catabolism of C6 components within the host cell. Such an approach may be particularly useful for methods involving (i) increasing relative concentration of adipic acid is increased and decreasing the amount of monoacids and hydroxy-acids in the mixed organic waste stream, and/or (ii) converting C6 components and precursors present in the mixed organic waste stream to α,ω-difunctional alkanes. In particular, catabolism of caproic acid, hydroxycaproic acid, and adipic acid by the host cell biocatalyst present in the mixture may be reduced by reducing degradation to acetyl-CoA through beta-oxidation.

The decrease in the rate of host cell catabolism of C6 compounds present in the mixed organic waste stream can be achieved by deleting or inhibiting enzymes in the host cell biocatalyst that activate caproic acid, hydroxycaproic acid, and adipic acid to their corresponding CoA esters. For example, the deletion or inhibition of host cell enzymes such as CoA ligases and transferases can decrease the rate at which these compounds are catabolized. By way of further example, deletion or inhibition of host cell enzymes such as acyl-CoA oxidases and acyl-CoA dehydrogenases can also decrease the rate at which caproic acid, hydroxycaproic acid, and adipic acid to their corresponding CoA esters via the host cell's beta-oxidation pathway.

In one aspect, the transport of species in NVR or COP acid into and out of the cell to improve uptake of substrates and secretion of products is optimised by metabolic engineering. This is achieved by expressing additional transporters of monoacids, or by engineering of transporters to improve the uptake rate of the monoacids. Alternatively, the first enzyme acting on the monoacids, such as a CytP450, may be displayed on the cell surface to transform the monoacid into a hydroxyacid that is taken up into the cell at a higher rate than the monoacid.

Use of $C_3$-$C_5$ Molecules as a Carbon Source by Growing Whole Cell Biocatalysts The mixed organic waste stream of a cyclohexane oxidation process that is used as the starting material in the methods of the invention comprise a mixture of oxidized hydrocarbon molecules. The claimed methods improve the properties and composition of the mixed organic waste stream by applying at least one biocatalyst to the stream, which enzymatically converts undesirable components present in the waste stream into more desirable products, such that the treated waste stream can be used in subsequent chemical and/or enzymatic processing to provide a high yield of the desired product, in the highest possible purity. As described above, the resulting products of cyclohexane oxidation include the breakdown products of the original $C_6$ molecule, including pentanoic acid, 5-hydroxypentanoic acid, butanoic acid, 4-hydroxybutanoic acid, and propanoic acid, which are found in NVR and/or water wash. In order to improve the properties of NVR and/or water wash, a whole cell biocatalyst is applied to the waste stream to utilize the unwanted compounds that are present in the stating material.

In one aspect, the complexity of the mixed organic waste stream, e.g., NVR, can be reduced by decreasing the presence of C3-C6 components in the waste steam. One way to achieve the reduced complexity is to select a host cell biocatalyst that can utilize the $C_3$-$C_5$ components of the mixed organic waste stream as a carbon source for growth. Such a reduction in the complexity of the mixed organic waste stream may be useful to directly increase the relative concentration of adipic acid as well as indirectly increase the relative concentration of adipic acid by facilitating recovery of adipic acid from caproic acid, hydroxy-caproic acid, and cyclic C6 compounds, e.g., K and A.

Pentanoic acid, butanoic acid, and propanoic acid can be used as a carbon source by a cell by the ligation of CoA (coenzyme A) to the molecule and the metabolism of the CoA-ligated molecule into the beta oxidation pathway of the cell. Thus, in some embodiments, the whole cell biocatalyst used in the methods of the invention comprises an acyl-CoA ligase and/or CoA transferase which are capable of ligating CoA to pentanoic acid, butanoic acid, and/or propanoic acid. Additionally, 5-hydroxypentanoic acid and 4-hydroxybutanoic acid, which are frequently also present in the non-volatile residues and/or water wash of cyclohexane oxidation that is used as the starting material in the methods of the invention, can also be metabolized by whole cells to further improve the purity of the product of the method of the invention. 5-hydroxypentanoic acid can be oxidized to 5-oxopentanoic acid by an alcohol dehydrogenase, and 4-oxopentanoic acid can in turn be oxidized to pentane-1,5-dioic acid (glutaric acid) by an aldehyde dehydrogenase. Ligation of CoA to pentane-1,5-dioic acid by an appropriate acyl-CoA ligase and/or CoA transferase results in the compound being metabolized via the beta oxidation pathway of the cell. 4-hydroxybutanoic acid can be oxidized to 4-oxobutanoic acid by an alcohol dehydrogenase, which can in turn be oxidized to butane-1,4-dioic acid (succinic acid) by an aldehyde dehydrogenase. Succinic acid is a central component in the tricarboxylic acid cycle (also known as the citric acid cycle or the Krebs cycle). Propionic acid can also be catabolized to pyruvate and B-alanine.

Pre-Treatment of Mixed Organic Waste Streams to Remove Inhibitory Compounds

The inventors have identified valerolactone as the primary inhibitory compound present in mixed organic waste streams, and confirmed that valerolactone is responsible for preventing the growth of a NVR-tolerant host cell. Based on the identification of valerolactone as the key inhibitory component of NVR, the waste stream can be treated appropriately to remove valerolactone from the waste stream or diminish the amount valerolactone present in the waste stream, as to permit suitable host cell's to grow in the presence of NVR.

In one aspect, the mixed organic waste stream is pre-treated with either free or immobilized enzymes that hydrolyze inhibitory compounds, or otherwise effectively remove inhibitory compounds from the stream. Such removal of inhibitory compounds alleviates inhibition of host cell growth in the mixed organic waste stream.

The non-volatile residues, COP acid, or water wash streams may undergo pre-treatment to remove inhibitory compounds prior and/or to hydrolyze the polymeric esters prior to its use as substrate. For instance, the alkyl hydroperoxides present in the water wash, may be removed by treatment with a suitable biocatalyst, such as a peroxidase/catalase, e.g. KatA, KatG and other enzymes in the class EC 1.11.1-, including alkyl hydroperoxide reductases (for example Ahpl in yeast or AhpC in bacteria), EC 1.11.1.15 and other alkyl hydroperoxide reductases (e.g. EC 1.8.1.- and EC 1.6.99.3), with or without electron donors such as AhpD or AhpF. A combination of carboxylesterases (to hydrolyze the polymeric esters in the mixture) and enzymes acting on alkyl hydroperoxides may be used as an enzyme preparation added to the stream prior to feeding it into the bioreactor, or by feeding the untreated stream into a 'pre-fermenter' containing a microbial culture capable of hydrolysing the polymeric esters by secretion of lipases/esterases and simultaneously reducing the organic hydroperoxides prior to feeding the supernatant into the second bioreactor for the production of valuable compounds.

Additionally, mixed organic waste streams may be treated with a lactone hydrolase or other enzymes (host cell biocatalysts or enzymes isolated from a host cell) that is capable of removing the inhibitory lactone components from the stream, thereby improving the growth of a host cell using the stream as a carbon source. The growth of microorganisms in mixed organic waste streams may be compromised by the presence of such inhibitory compounds. In particular, various strains of *Y. lipolytica* that were grown in a culture containing NVR were unable to attain steady state growth as a result of valerolactone accumulation. See, Example 4. However, a host cell that expresses and secretes a lactone hydrolase, which converts valerolactone to hydroxyvaleric acid, may successfully grow in NVR because the inhibitory compound has been removed from the medium. See, Example 5.

Selection of Host Cells Tolerant to Mixed Organic Waste Streams

Alternatively, to improve growth of the biocatalyst in a culture containing a mixed organic waste stream, a host cell may be selected that it tolerant to the mixed organic waste stream, e.g., able to grow in a culture containing NVR, COP acid, or water wash waste stream.

Furthermore, a tolerant host cell may be grown in a culture including a certain percentage by volume of treated mixed organic waste stream. Use of a tolerant host cell in combination with a pre-treated mixed organic waste stream, e.g., application of a hydrolase to remove lactone compounds, like valerolactone, may significantly improve growth of the host cell in medium containing the waste stream material.

In one aspect, the biocatalyst is a naturally occurring or non-naturally occurring host cell that is tolerant to a mixed organic waste stream, such as NVR. Preferably, the host cell is tolerant to at least 1% of the mixed organic waste stream by volume. For example, the host cell biocatalyst is capable of achieving stead state growth in a culture containing at least 1% NVR.

In another aspect, the tolerance of the host cell to the mixed organic waste stream is improved by the reduction in the amount of inhibitory compounds present in the mixed organic waste stream. As discussed above, pre-treatment of the waste stream with a 1,4-lactonease class of enzyme (EC 3.1.1.25) to covert valerolactone to hydroxycaleric acid in the medium may promote cell growth in the presence of the remaining waste stream components. In addition, the gluconolactonase class of enzymes (EC 3.1.1.17) may also be used to convert lactones into their corresponding acid form, hydroxy carboxylic acid. See, Example 5.

In one aspect, the inhibitory compounds present in the mixed organic waste streams are lactones, and the amount of lactones in the mixed organic waste stream is reduced by treatment of the stream with one or more enzymes that are capable of hydrolyzing a lactone to the corresponding hydroxyl-acid before or during treatment of the mixed organic waste stream with a naturally occurring or non-naturally host cell that is capable of mediating the conversions necessary to increase the relative amount of diacids, increase the relative concentration of adipic acid and reduce the amount of mono-acid and hydroxy-acid, and/or convert C6 components and precursors to a, co difunctional alkanes.

Separation and Recovery of Products

The invention also provides for the separation and/or recovery of the monomeric components (e.g., diacids, adipic acid) described herein. For example, the invention provides for methods of separating adipic acid or adipic acid derivatives from the reaction mixture after conversion of 6-carbon components of the mixed organic waste stream, e.g., 6-oxohexanoic acid, to adipic acid. These separated products can be further purified by removal of the C4 and C5 diacid and/or derivatives that could be separated in the initial step.

In one aspect, adipic acid is separated from other components by crystallization of the adipic acid from a concentrated reaction mixture or by esterification and distillation of the adipate diesters from the reaction mixture.

As discussed supra, a biocatalyst can be used to convert linear C4-C6 monoacid and hydroxyacid components, as well as cyclic C6 components, into a mixture of C4-C6 diacids that can be subsequently separated into C4, C5, and C6 diacids. In one aspect, the diacids mixture is esterified prior to separation into C4, C5, and C6 diacids.

Compositions of a Mixed Organic Waste Stream and Biocatalyst

The invention also provides compositions comprising a mixed organic waste stream of a cyclohexane oxidation process and a biocatalyst. In one aspect, the mixed organic waste stream is NVR, water wash/COP acid, or caustic wash stream.

In one aspect, the biocatalyst is an isolated enzyme or an enzyme secreted by a naturally occurring or non-naturally occurring host cell. The composition may comprise one or more enzymes selected from the enzymes detailed in the previous sections, or a non-naturally occurring variant thereof.

In one aspect, the composition comprises a host cell biocatalyst that is tolerant to the mixed organic waste stream. In other words, the biocatalyst is able to grow in a culture containing the mixed organic waste stream to densities that are industrially useful. Preferably, the host cell is tolerant to NVR. In another aspect, the host cell is tolerant to at least 1% of the mixed organic waste stream by volume. Therefore, the host cell is able to grow in a culture containing 1% of the mixed organic waste stream by volume, to reach densities that are industrially useful.

Omega oxidation ($\omega$-oxidation) is an alternative pathway to beta oxidation ($\beta$ oxidation) for fatty acid metabolism. The $\omega$-oxidation pathway involves the oxidation of the $\omega$ carbon, i.e., the carbon most distant from the carboxyl group of the fatty acid, unlike the $\beta$ oxidation pathway that involves the $\beta$ carbon. The $\omega$-oxidation process is normally a minor catabolic pathway for medium-chain fatty acids, i.e., C10-12, but the pathway becomes more important when $\beta$-oxidation is defective. The $\omega$-oxidation process involved hydrozylation of the $\omega$ carbon, and successive oxidation, yielding adipic acid and other products, e.g., succinic acid.

In one aspect, the naturally or non-naturally occurring host cell biocatalyst comprises an endogenous or heterologous $\omega$-oxidation pathway that is able to convert aliphatic fatty acids to diacids via hydroxyl-acids and oxo-acids. Preferably, the host cell biocatalyst with the $\omega$-oxidation pathway is an n-alkane utilizing yeast or bacterium.

A skilled artisan is aware of numerous n-alkane utilizing yeast or bacterium that are suitable for used in the claimed methods. In one aspect, exemplary n-alkane utilising yeast include *Yarrowia lipolytica, Candida tropicalis, C. albicans, C. cloacae, C. guillermondii, C. intermedia, C. maltosa, C. parapsilosis, C. zeylenoides*, or combinations thereof, yeasts of the *Rhodotorula, Rhizopus, Trichosporon, Debaryomycesand Lipomyces* genera or combinations thereof. In another aspect, exemplary n-alkane utilising bacteria include *Pseudomonas fluorescens, P. putida, P. aeroginosa, P. oleoverans, Marinobacter hydrocarbonoclasticus, Acinetobacter* sp. such as *A. venetianus, Oleiphilus messinensis, Arthrobacter viscosus, Cupriavidus metallidurans, Rhodococcus* sp. such as *R. rhodochrous* and *R. erythropolis, Sphingomona spaucimobilis, Burkholderia cepacia, Delino acidovorans, Alcanivorax diesolei* or combinations thereof.

Fermentation Process

The fermentation process of the invention may be performed in batch, fed-batch or continuous mode. In fed batch mode, the process may be performed with partial drops. Alternatively, chemostat fermentation may be employed, with or without cell retention. See, Example 3. Furthermore, components in the waste stream may be fed as sole carbon and energy source, or a co-feed of glycerol or sugar or other suitable fermentable carbon or energy source may be used as additional source of energy and carbon to obtain higher biomass. Carbon source limiting cultivation may be employed to reduce the toxicity of species in NVR and COP acid. In a preferred embodiment, cultivation is performed within a pH range of 5-8, more preferably between pH 6 and pH 7.5 to overcome growth inhibition by undissociated organic acids.

The following examples are not intended to limit the invention in any way.

EXAMPLES

Example 1

Hydrolysis of Oligomeric Esters in NVR, COP acid & Water Wash

Commercial lipases (free and immobilized) and esterases from different classes based on the topography of their binding sites were selected to screen for hydrolysis of oligomeric esters in NVR and COP acid (Table 1 and 2). Based on the results of this screen, the Lipase Engineering database (LED) (Widmann et al., BMC Genomics 2010, 11:123) and other bioinformatics resources were used to identify additional candidate enzymes to screen for the hydrolysis of oligomeric esters, and, in particular, enzymes that are thermostable or active at low pH. People skilled in the art will understand that it is also possible to change the pH optimum and stability of enzymes with the desired activity or to alter the substrate specificity of enzymes with the desired pH and stability properties or both, by enzyme engineering using rational design or directed evolution techniques.

Screening methods for hydrolysis of oligomeric esters in NVR and COP acid with commercially available lipases and esterases were verified using commercially available caprolactonediol (CPL) polymers with a range of molecular weights. Both agar plate assays where radial enzyme diffusion produces clearance zones if the oligomer in the agar is hydrolyzed, and biotransformation reactions assayed by HPLC with UV detection or LC-MS to quantify the concentrations of monomers were used to identify candidate enzymes. The two screening methods provide complementary information: the size of the clearance zones observed with plate assays is indicative of overall hydrolytic activity (endo and exo cleavage) to hydrolyze oligomers to smaller esters that are soluble, while liquid chromatography provides data about the increase in monomer concentration thus identifying enzymes that hydrolyze terminal monomers of the oligomers.

For plate assays, agar plates (1.5% agarose) containing 1-4% polycaprolactone (PCL), NVR or COP acid (v/v) was prepared with 50 mM citrate, Tris/HCl, or phosphate buffers to assay enzymes for hydrolytic activity at pH 3, 5, 5, 7 & 8. The molecular weight of PCL is 530 g/mol. Wells with a ca. 3 mm diameter were made in the plates, and enzyme added (1 U/well). Clearance zones were measured after 24 hours. See, Tables 1 and 2 showing the results comparing the activity of commercial lipases and esterases, respectively, for hydrolysis of oligomers in NVR, COP acid and caprolactone polymers.

Figure 5:
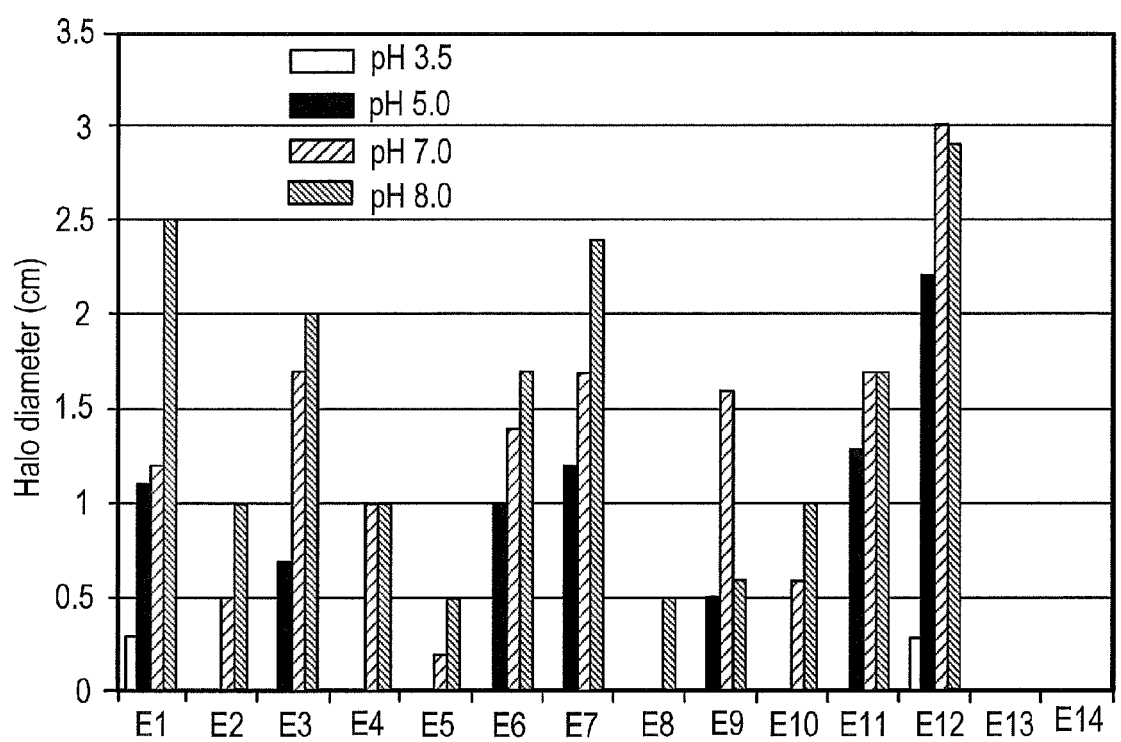
FIG. 5 shows hydrolysis of polycaprolactone diol polymer (2%, w/v, MW=530 g/mol) by selected esterases at different pH. The esterase from *Mucor miehei* (E1) and *Rhizopus oryzae* (E12) was active at pH 3.5. The esterase from *Streptomyces diostotochromogenes* (E8) is an alkaline esterase and only displayed activity at pH>8.
Figure 6:
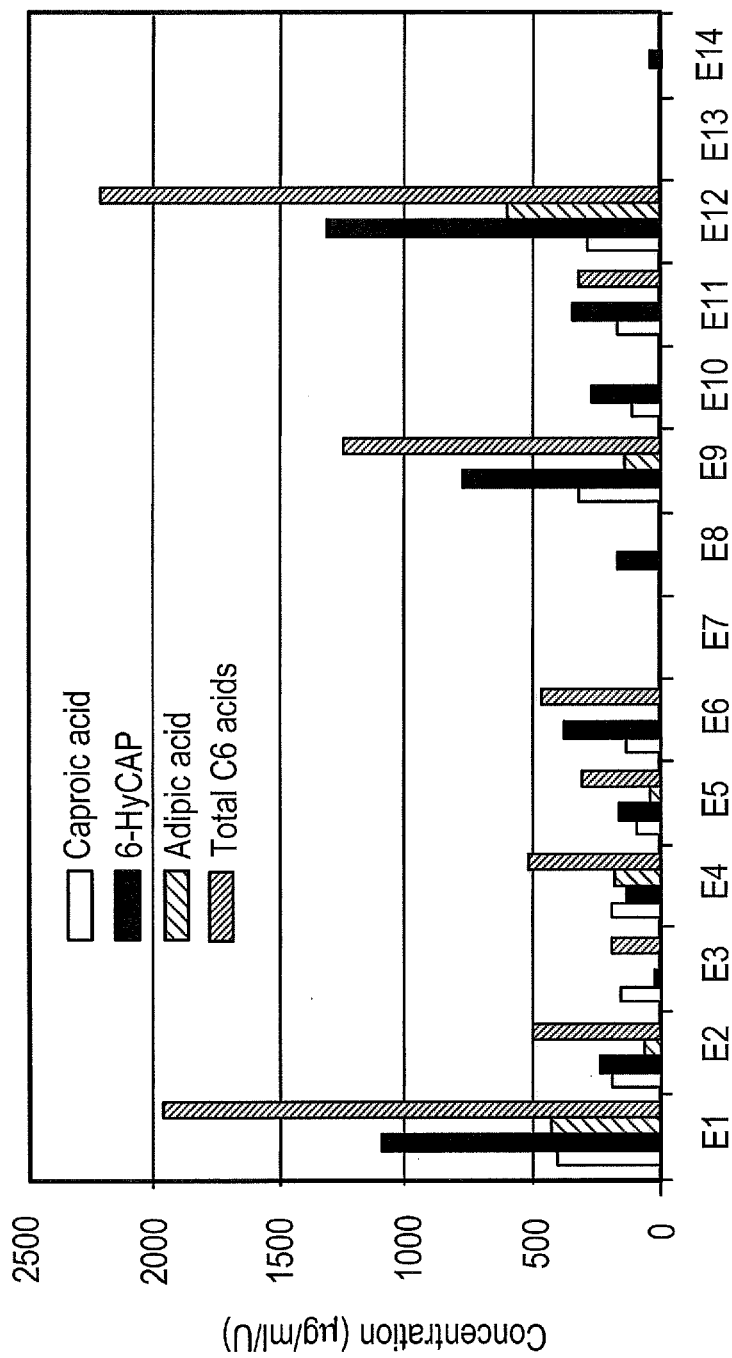
FIG. 6 shows an increase in the concentration of caproic acid, 6-hydroxycaproic acid, adipic acid and total acids in NVR reaction mixture (2% v/v) in phosphate buffer (100 mM, pH 7.0) treated for 16 hours with selected esterases during biotransformation assays.
Figure 7:
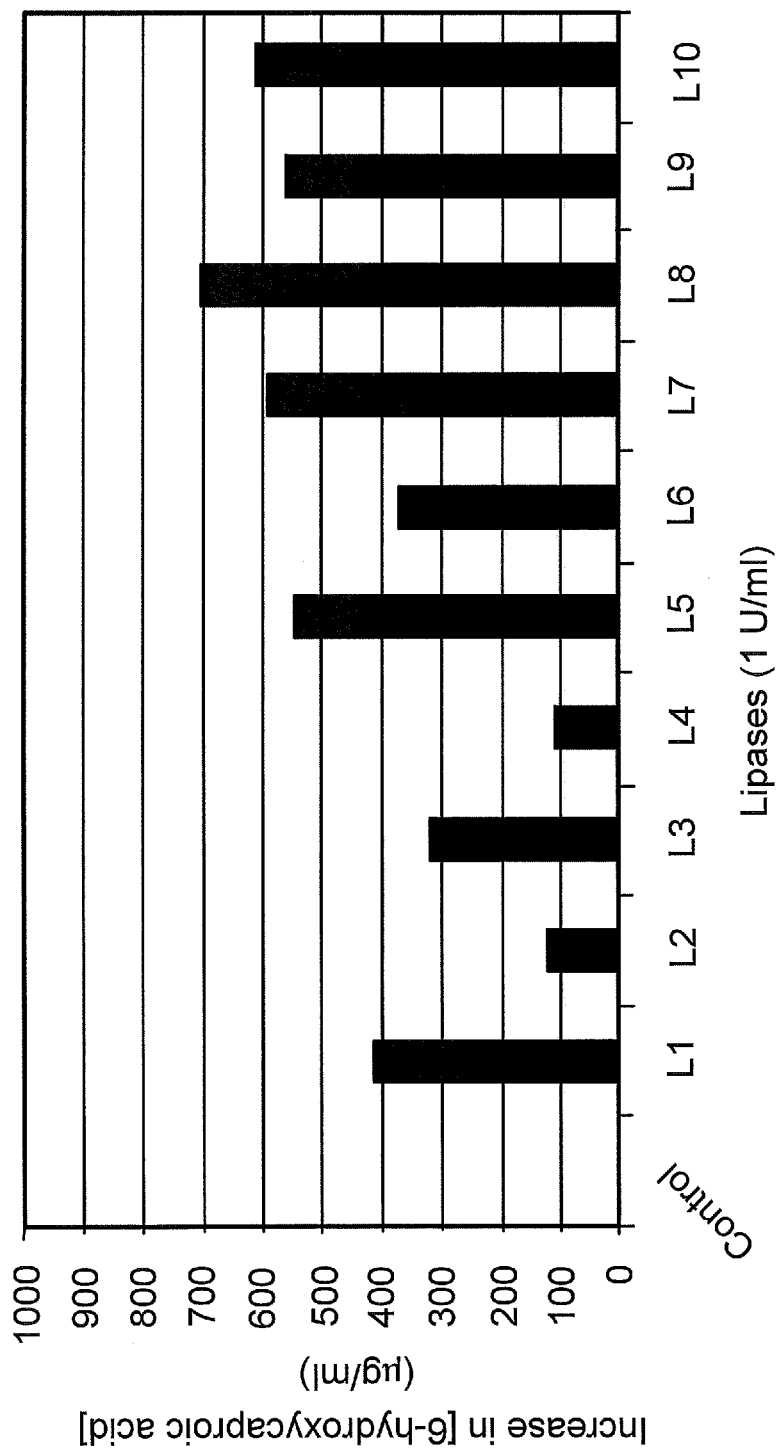
FIG. 7 shows the increase in the concentration of 6-hydroxycaproic acid in NVR reaction mixture (2% v/v) in phosphate buffer (100 mM, pH 7.0) treated for 16 hours with selected lipases during biotransformation assays
Figure 8:
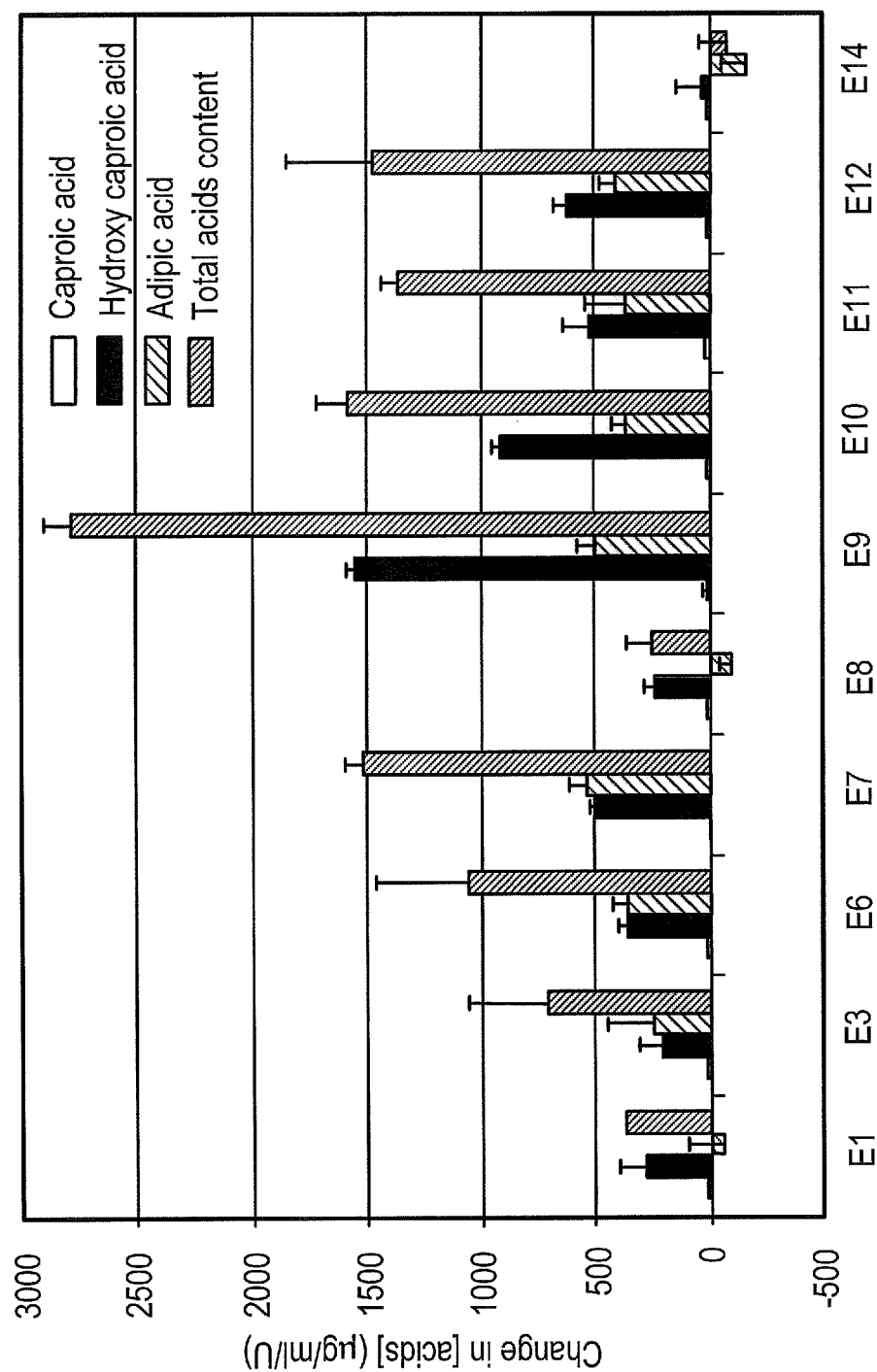
FIG. 8 shows an increase in the concentration of caproic acid, hydroxycaproic acid, adipic acid and total acids in COP acid (4% v/v) in phosphate buffer (100 mM, pH 7.0) treated for 16 hours with selected esterases during biotransformation assays.
Figure 9:
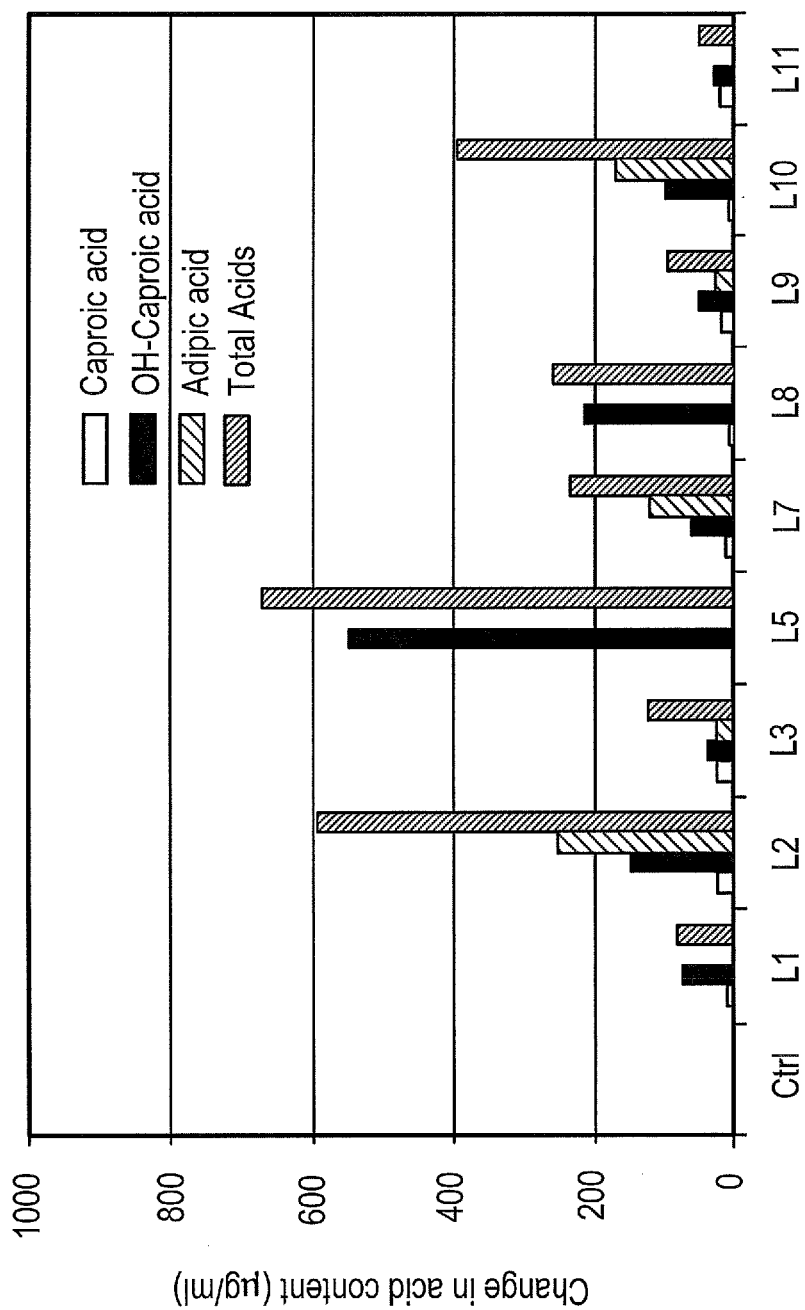
FIG. 9 shows an increase in the concentration of caproic acid, hydroxycaproic acid, adipic acid and total acids in COP acid (4% v/v) in phosphate buffer (100 mM, pH 7.0) treated for 16 hours with selected lipases during biotransformation assays.

Biotransformation reactions with unbound commercial esterases and lipases were performed with the same buffers and concentrations of substrates as for the plate assays. Reactions were started by addition of commercial enzyme preparations (1 U/ml). In the case of immobilised lipases, ChiralVision Immozyme™ lipase kit was used (enzymes covalently bound to polyacrylic beads) for hydrolysis of oligomeric esters in NVR. Immobilised enzyme (100 mg) was incubated with 2% NVR (v/v) in 1 ml phosphate buffer pH 7.0. Biotransformation reactions were stopped after 16 hours by inactivation of the enzymes at 100° C. for 10 min, centrifuged, filtered and analyzed by HPLC or LC-LC-MS. See, FIG. 4 showing typical clearance zones on agar plates and FIG. 5 comparing the relative activity as measured by the diameter of the clearance zone of esterases at different pH.

HPLC analysis was performed on a Shimadzu HPLC 2100 system with DAD detector monitoring at 210 nm. Separation was performed on a Synergi Fusion RP column (250 mm×4.6 mm) at a flow rate of 0.9 ml/min and samples was eluted using phosphoric acid and acetonitrile.

LC-MS analysis was performed on an Agilent 1290 Infinity UHPLC system coupled with an Agilent 6530 Accurate—Mass Q-TOF LC/MS.

LC conditions for acids and lactones:
Column: 100×2 mm Synergi Fusion RP column (Phenomenex)
Column oven temperature: 40° C.
Injection volume: 2 µL
Eluent: A: 5 mM ammonium acetate containing 0.1% acetic acid
B: acetonitrile containing 5% water
Gradient:

| Time(min) | % Mobile Phase A | % Mobile Phase B | Flow Rate |
|---|---|---|---|
| 0.00 | 99 | 1 | 0.300 mL/min |
| 1.00 | 99 | 1 | |
| 6.00 | 80 | 20 | |
| 7.50 | 60 | 40 | |
| 8.00 | 60 | 40 | |
| 8.20 | 99 | 1 | |
| 10.00 | 99 | 1 | |

MS Q-TOF Conditions: Ion Source: ESI (Electro Spray Ionization). Polarity mode: Negative (acids) and positive (lactones).

Figure 10:
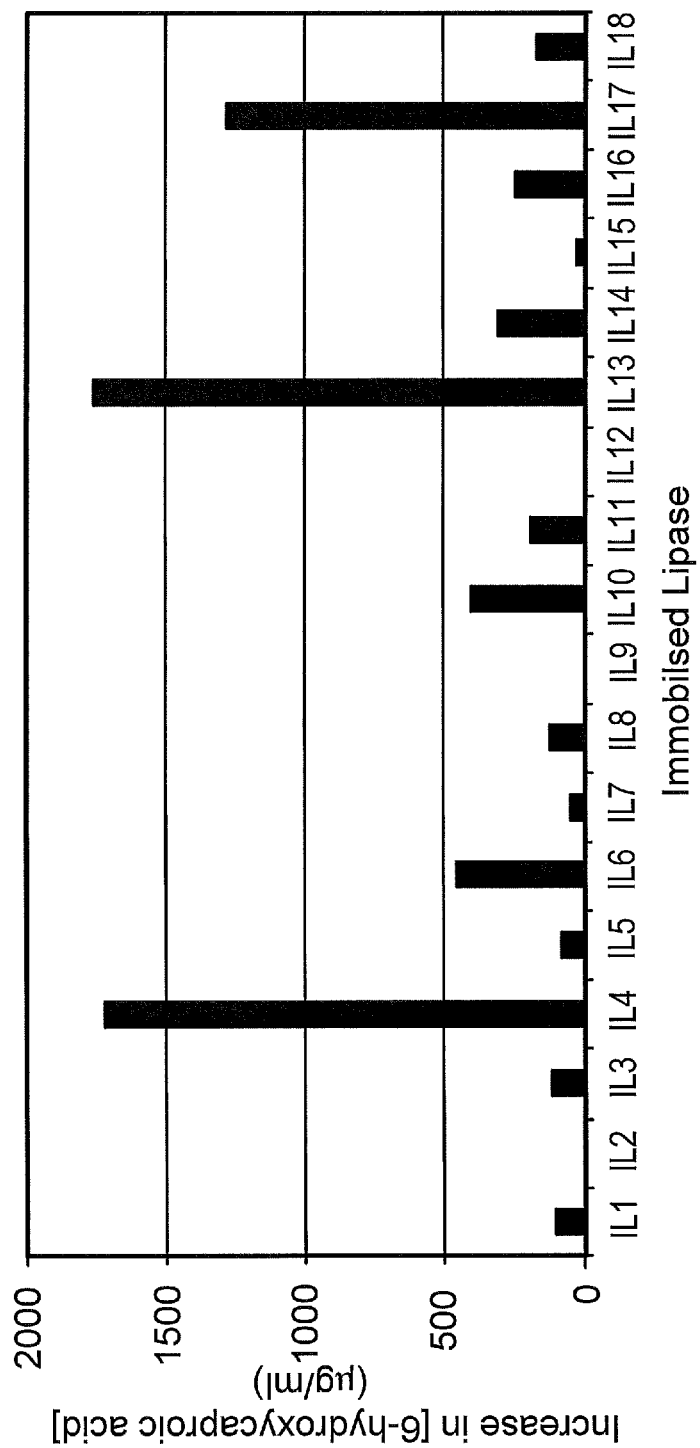
FIG. 10 shows an increase in the concentration of 6-hydroxycaproic acid, in NVR (4% v/v) in phosphate buffer (100 mM, pH 7.0) treated for 16 hours with immobilized lipases during biotransformation assays.

FIGS. 6, 7, 8, and 9 shows the increase in the concentration of monomers (caproic acid, hydroxycaproic acid, adipic acid and total acids) due to hydrolysis of oligomeric esters in NVR and COP acid by the action of commercial lipases and esterases as assayed by LC and LC/MS. The release of monomers from oligomeric esters in NVR by immobilized lipases as measured by LC/MS is depicted in FIG. 10.

TABLE 1

Commercial esterases and lipases evaluated for the hydrolysis of oligomers in NVR and COP acid.

| Esterases | | Lipases | |
|---|---|---|---|
| E1 | *Mucor miehei* | L1 | *Thermomyces lanuginosus* |
| E2 | *Methylobacterium populi* | L2 | *Burkholderia cepacia* |
| E3 | *Pseudomonas fluorescens* | L3 | *Penicillium camemberti* |
| E4 | *Pelobacter propionicus* | L4 | *Thermus thermophiles* |
| E5 | *Nocardia forcinico* | L5 | *Candida antarctica* lipase A |
| E6 | Cholesterol esterase *Pseudomonas* sp. | L6 | *Chromobacterium viscosum* |
| E7 | *Bacillis steorothermophilus* | L7 | *Rhizomucor miehei* |
| E8 | *Streptomyces diostotochromogenes* | L8 | *Mucor meihei* |
| E9 | Esterase from horse liver | L9 | *Rhizopus niveus* |
| E10 | Esterase from hog liver | L10 | *Pseudomonas fluorescens* |
| E11 | *Candida lipolytica* | L11 | *Candida rugosa* lipase III |
| E12 | *Rhizopus oryzae* | L12 | *Aspergillis niger* |
| E13 | *Bacillus* sp. | L13 | *A. niger* amanolipase A |
| E14 | *Saccharamyces cerevisiae* | L14 | Procine pancrean lipase II |

TABLE 2

Immobilised lipases evaluated for the hydrolysis of oligomers in NVR and COP acid.

| No. | Source | Synonym |
|---|---|---|
| IL1 | *Alcaligenes* sp. | Lipase QLM |
| IL2 | *Aspergillus niger* | Lipase A |
| IL3 | *Bacillus subtilis* | Lipase |
| IL4 | *Candida antarctica*, A | CaLA |
| IL5 | *Candida antarctica*, B | CaLB |
| IL6 | *Candida antarctica*, B | CaLBY |
| IL7 | *Candida cylindracea* | Lipase OF |
| IL8 | *Candida rugosa* | CRL |
| IL9 | Lipex 100L | Lipex 100L |
| IL10 | *Mucor javanicus* | Amano M |
| IL11 | Novozymes 51032 | 51032 |
| IL12 | *Pseudomonas cepacia* | Amano PS |
| IL13 | *Pseudomonas fluorescens* | Amano AK |

TABLE 2-continued

Immobilised lipases evaluated for the hydrolysis of oligomers in NVR and COP acid.

| No. | Source | Synonym |
|---|---|---|
| IL14 | Resinase HT | Resinase HT |
| IL15 | *Rhizomucor miehei* | Lipozyme |
| IL16 | *Rhizopus niveus* | Lipase |
| IL17 | *Rhizopus oryzae* | Amano F-AP15 |
| IL18 | *Thermomyces lanuginosa* | Lipolase |

TABLE 3

Comparison of the hydrolytic activity of commercial esterases assayed by measuring the clearance zone diameter on agar plates containing Polycaprolactone (PCL) polymer (MW 530 g/mol), NVR or COP acid

| | Substrate Clearance Zone Diameter | | | | | |
|---|---|---|---|---|---|---|
| Esterase | 2% (v/v) PCL diol pH = 5 | 2% (v/v) PCL diol pH = 7 | 2% (v/v) PCL diol pH = 8 | 2% (v/v) NVR pH = 7 | 2% (v/v) NVR pH = 8 | 4% (v/v) COP acid pH = 7 |
| E1 | 1.1 | 1.2 | 2.5 | 1.7 | 2.3 | 2.4 |
| E2 | 0 | 0.5 | 1 | 0 | 1 | 0 |
| E3 | 0.7 | 1.7 | 2 | 1.2 | 1.4 | 1.9 |
| E4 | 0 | 1 | 1 | 0 | 0 | — |
| E5 | 0 | 0.2 | 0.5 | 0 | 0 | — |
| E6 | 1 | 1.4 | 1.7 | 1.2 | 1.5 | 1.5 |
| E7 | 1.2 | 1.7 | 2.4 | 1.5 | 1.5 | 1.1 |
| E8 | 0 | 0 | 0.5 | 0 | 0 | 1.6 |
| E9 | 0.5 | 1.6 | 0.6 | 0 | 0.8 | 2.8 |
| E10 | 0 | 0.6 | 1 | 0 | 0.5 | 1.0 |
| E11 | 1.3 | 1.7 | 1.7 | 0.5 | 1.7 | 1.4 |
| E12 | 2.2 | 3 | 2.9 | 1 | 0.8 | 2 |
| E13 | 0 | 0 | 0 | 1.6 | 0.5 | 1.0 |
| E14 | 0 | 0 | 0 | 0 | 0 | 0 |

TABLE 4

Comparison of the hydrolytic activity of commercial lipases assayed by measuring the clearance zone diameter on agar plates containing Polycaprolactone (PCL) polymer (MW 530 g/mol), NVR or COP acid.

| | Substrate Clearance Zone Diameter | | | | | | |
|---|---|---|---|---|---|---|---|
| Lipase | 2% (v/v) PCL diol pH = 5 | 2% (v/v) PCL diol pH = 7 | 2% (v/v) PCL diol pH = 8 | 1% (v/v) NVR pH = 7 | 2% (v/v) NVR pH = 7 | 2% (v/v) NVR pH = 8 | 4% (v/v) COP acid pH = 7 |
| L1 | 1 | 1.6 | 2 | 0.5 | 3 | 1.5 | 1.1 |
| L2 | 0 | 1.6 | 1 | 0.5 | 1.5 | 1.4 | 0.8 |
| L3 | 0 | 1.4 | 0.7 | 0.3 | 0 | 0 | 0 |
| L4 | 0.5 | 0 | 0 | 0 | — | — | 0 |
| L5 | 0.5 | 0 | 3 | 0 | — | — | 0.8 |
| L6 | 2.5 | 3.1 | 3 | 1.6 | 2.0 | 1.7 | 2.2 |
| L7 | — | — | — | 1.7 | — | — | 2.2 |
| L8 | — | — | — | 1.5 | — | — | 2.2 |
| L9 | — | — | — | 0 | — | — | 1.0 |
| L10 | — | — | — | 1 | — | — | 2.3 |
| L11 | — | — | — | 1 | — | — | 0.5 |
| L12 | — | — | — | 1.5 | 0 | — | 1.7 |
| L13 | — | — | — | 1.2 | 0 | — | 1.0 |
| L14 | — | — | — | 0 | — | — | — |

The results of the plate assays shows hydrolysis of oligomeric esters present in both NVR and COP acid in a pH range of pH 5-8 by several selected esterases and lipases. The esterases from *Mucor miehei* displayed high hydrolytic activity on plates across a wide pH range for both NVR and COP acid oligomers. Esterases from *Pseudomonas fluorescens, Bacillis steorothermophilus, Candida lipolytica* and *Rhizopus oryzae* displayed excellent hydrolytic activity for the synthetic polycaprolactonediol substrates, as well as for the oligomers in NVR and COP between pH 5-8. In addition, esterase from horse liver displayed excellent hydrolysis of COP acid oligomers. Similarly, the lipase from *Thermomyces lanuginosus* and *Chromobacterium viscosum* displayed high hydrolytic activity for both synthetic, NVR and COP acid oligomers across a wide pH range. In addition, the lipases from *Rhizomucor miehei, Mucor miehei, Pseudomonas fluorescens, Burkholderia cepacia,* and *Aspergillus niger* hydrolyzed the oligomers in both NVR and COP acid, producing large clearance zones. See, Table 3, 4 and FIG. 4.

The biotransformation assays shows a marked increase in monomer concentration when oligomeric esters in NVR and COP acid are treated with different lipases and esterases. However, the highest release of monomers as measured by LC/MS suggests the importance of selecting a combination of hydrolases for maximum release of monomers from COP acid and NVR oligomers. See, FIGS. 6, 7, 8 and 9. The esterase from horse liver (E9) displayed excellent release of monomers from both NVR and COP acid, but on plate assays the relative size of the clearance zone indicated only moderate hydrolytic activity. This would thus be an excellent choice of enzyme to use in combination with the esterase from *Mucor miehei* (E1) or *Rhizopus* oryzae (E12) to treat NVR or COP acid. The lipases from *Burkholderia* cepacia (L2) and *Candida antarctica* A (L5) displayed excellent release of monomeric acids from oligomeric acids in COP acid.

Overall, NVR and COP acid oligomers were hydrolyzed with good activity by several of the selected free lipases and esterases, and most of the enzymes retain excellent activity across a wide pH range (pH 5-8). See, FIG. 4A-C and FIG. 5.

Immobilized lipases (Table 2, FIG. 10) from *Candida antarctica* A (IL4), *Pseudomonas fluorescens* (1113) and *Rhizopus oryzae* (IL 17) displayed similar high exo-hydrolytic activities for oligomeric esters in NVR as the free lipases (L5, L10).

Hydrolysis of oligomers in NVR and COP acid by lipase variants obtained by directed evolution and expressed in a lipase deficient strain of Y lipolytica showed that improved lipase variants with higher activities can be obtained through directed evolution, and that cells secreting lipases into the medium can efficiently hydrolyse oligomeric esters.

Figure 11:
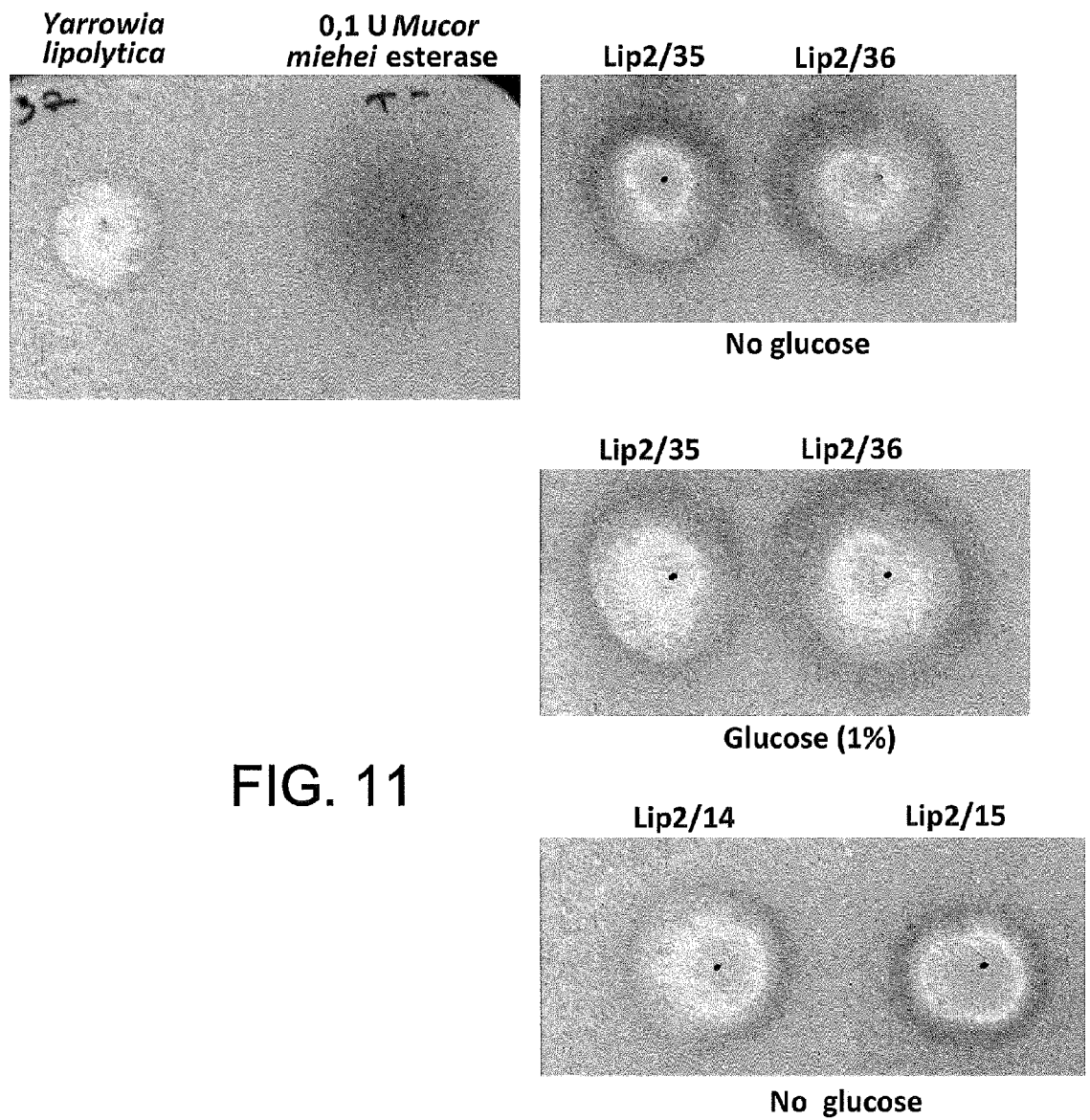
FIG. 11 shows photographs of representative clearance plate assays testing the ability of recombinant *Y. lipolytica* yeast strains, expressing variants of the endogenous Lip2 lipase created by directed evolution, to hydrolyze oligomeric esters. *Y. lipolytica* untransformed host and *Mucor miehei* esterase was used as controls to judge the relative activity of the secreted lipase variants. Variant 15 and 36 displayed high activity as judged by the size of the halo around the colony.

Hydrolysis of oligomeric esters was evaluated using drop plates as described above and yeast strains expressing variants of Lip2 (Bordes et al., 2011. Isolation of a thermostable variant of Lip2 lipase from *Yarrowia lipolytica* by directed evolution and deeper insight into the denaturation mechanisms. Journal of Biotechnology, 156: 117-124) was cultured overnight in YNB medium, diluted to OD600 1.0 and 5 µl was dropped onto agarose plates. The YNB agarose plates contained oleic acid (2%), polycaprolactone triol (2%) (Sigma 200387), 50 mM phosphate pH 7.0 with or without glucose (0.5%). Plates were incubated for 72 h at 28° C. and analysed for clearance zones surrounding the cells. The host strain with the major extracellular lipases deleted and 0.1 U of *Mucor miehei* esterase were used as controls. Strains expressing several variants of the library of LIP2 mutant lipases displayed significant hydrolysis of oligomeric esters as assayed by clear zones surrounding the cells. See, FIG. 11.

Example 2

Selection of Host Cells that Can Catabolize the Major C4 and C5 Components in NVR Removing C4 and C5 monoacids (butyric acid and valeric acid) and hydroxyacids from NVR, either by converting it to the corresponding diacids or by utilizing it for growth via n-oxidation is important to produce either a C4-C6 diacid mixture or adipic acid from NVR. In order to produce a diacid mixture from NVR, accumulation of the diacids from the mono-acids via ω-oxidation and a low consumption rate of the diacids compared to the monoacids are desirable. This example demonstrates selection of a host cell microorganism that can catabolize the major C4 and C5 components of mixed organic waste streams.

A mixed culture of *Yarrowia lipolytica* strains (72 total strains) were used as a starter culture for chemo-stat cultivation to select strains for their ability to efficiently utilize butyric acid and valeric acid. This was done by feeding the mono-acids as sole source of carbon during the chemo-stat cultivation. The consumption rates of the monoacids compared to that of the corresponding diacids (succinic acid & glutaric acid) was determined.

Figure 12:
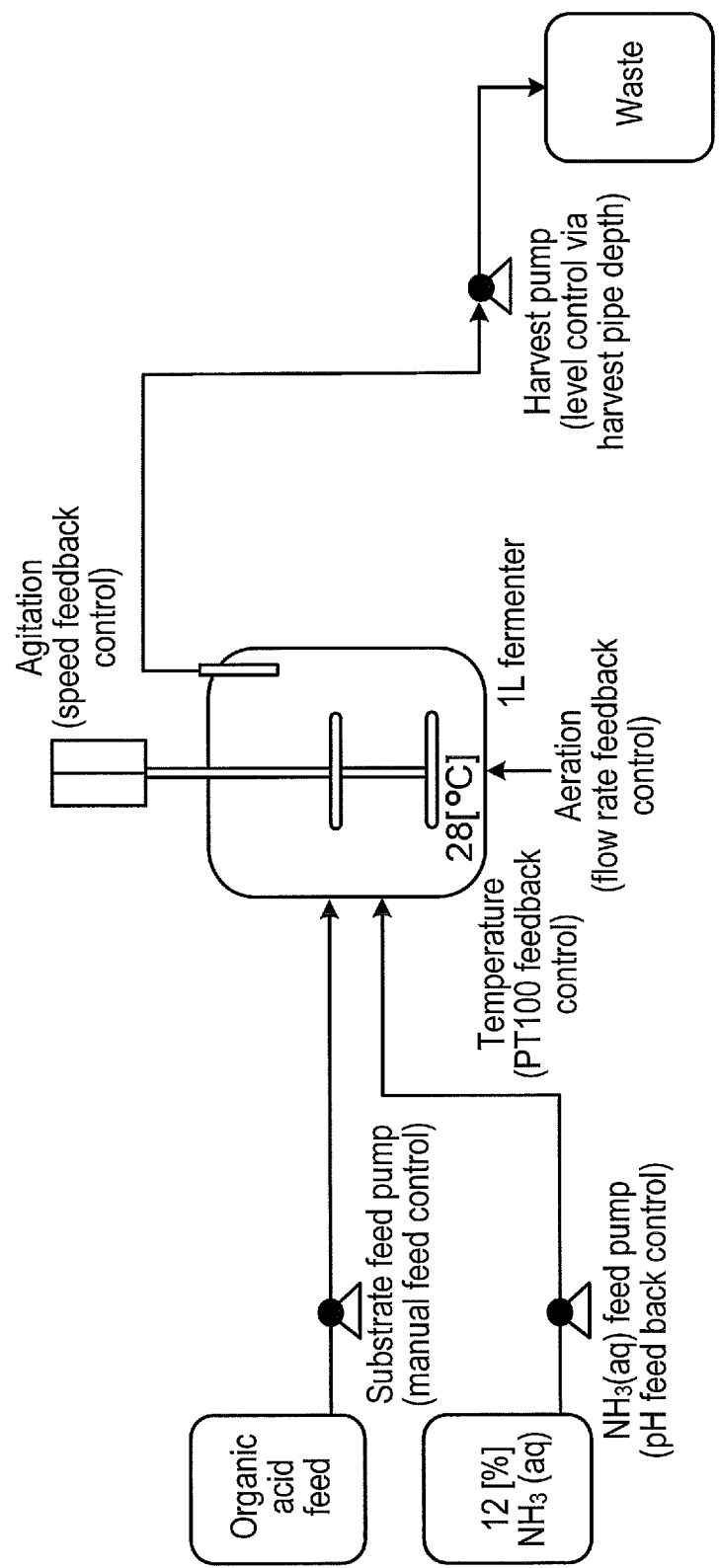
FIG. 12 is a schematic illustration of the chemo-stat fermentation set-up used to select strains that can catabolize butyric acid and valeric acid present in NVR.

A chemo-stat fermentation was set up, as shown in FIG. 12, with a 1 L jacketed glass fermenter. The experimental set-up provided for a Nutrient Feed containing C4 and C5 carbon sources prevalent in NVR and a Base Feed (12% (v/v) $NH_3$ (aq)), both filter sterilized into the fermenter via peristaltic pumps. Furthermore, a peristaltic pump allowed for biomass harvest from the fermenter.

The chemo-stat's control philosophy entailed manual feed control of the Nutrient Feed via the pump's variable speed drive, pH control via the Base Feed, temperature control via cooling water supply to the fermenter's jacket, fixed aeration, and agitation rates via the respective feedback loops and level control via the harvest pipe depth using the harvest pump.

The initial charge minimal media was prepared (6.7 g/L yeast nitrogen base without amino acids, 16.5 g/L glucose $H_2O$, 1 mL/L antifoam) and the Nutrient Feed containing the C4 and C5 acids was prepared (A1: 6.7 g/L yeast base without amino acids; 10 g/L valeric acid; 0.4 g/L succinic acid; 2.3 g/L butyric acid; 0.8 g/L glutaric acid; and 1 mL/L antifoam; A2: 6.7 g/L yeast base without amino acids; 30 g/L valeric acid; 1.2 g/L succinic acid; 6.9 g/L butyric acid; 2.3 g/L glutaric acid; and 1 mL/L antifoam). The control parameters for the fermenter were set up (A1 and A2: 1 vvm aeration, pH 7.0, DO calibration at pH 7.0 and 1 vvm to 100% saturation, 28° C., 750 rpm initial agitation until glucose depletion, max rpm final agitation after glucose depletion, manual antifoam).

Figure 13:
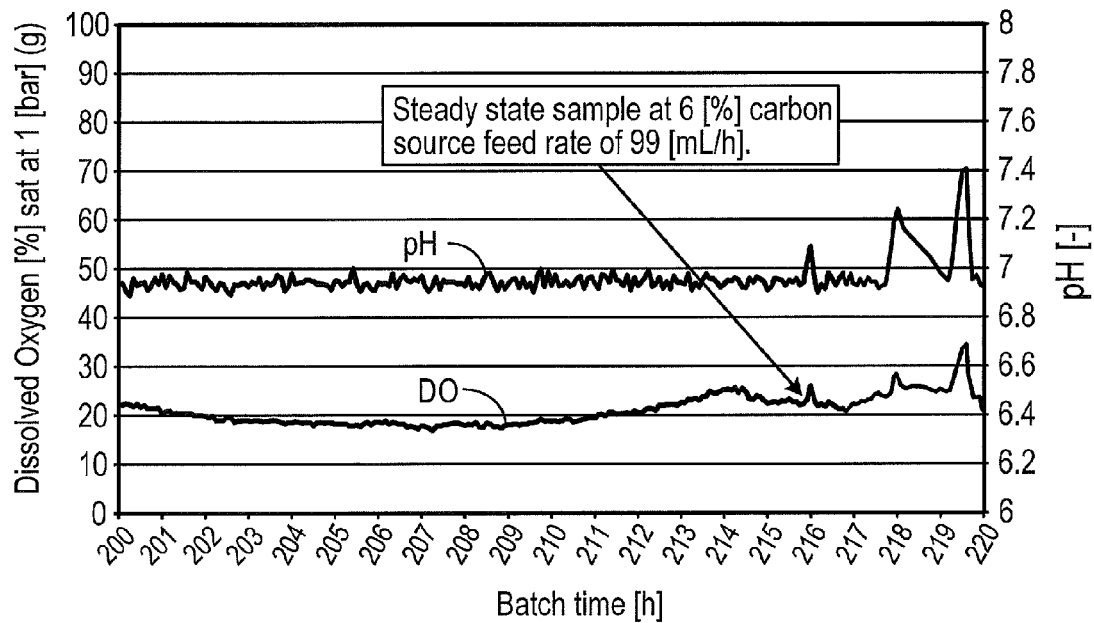
FIG. 13 is a graphical representation showing that chemostat steady state was attained at a dilution rate of about 0.1 [h$^{-1}$].
Figure 14:
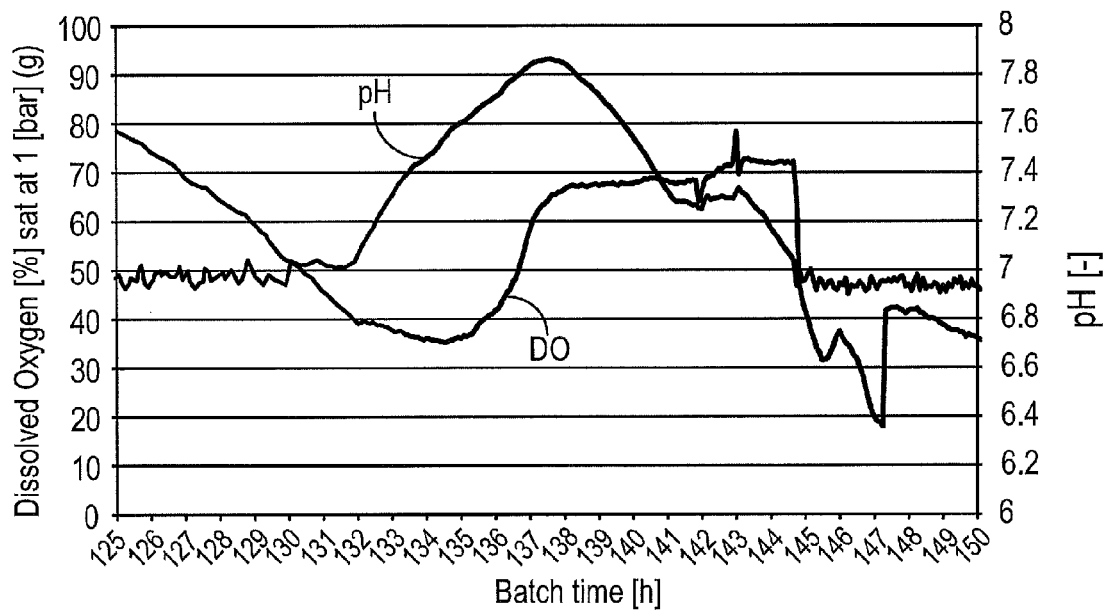
FIG. 14 is a graphical representation showing the pH disturbance during the approach to steady state at a dilution rate of about 0.1 [h$^{-1}$].
Figure 15:
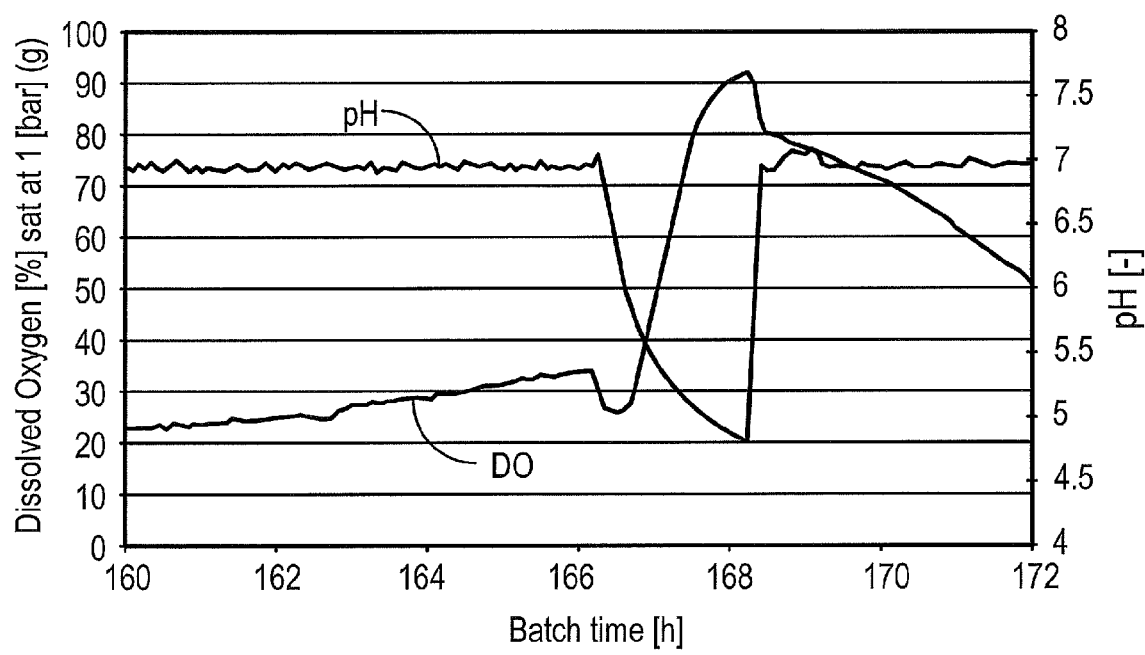
FIG. 15 is a graphical representation showing the results from a pH excursion drift experiment at near steady state at a dilution rate of about 0.1 [h$^{-1}$].

The fermenter was inoculated with a 10 [%] (v/v) inoculum from a mixture of 72 wild-type *Yarrowia lipolytica* strains using 750 µL from each shake flask that was grown overnight from a cryopreserved stock. Cultures were grown in batch phase on glucose until steady state was reached. Nutrient feed was commenced and steady state was attained at a dilution rate of ~0.1 [$h^{-1}$] at a dissolved oxygen (DO) concentration of ~20 [%] of saturation (FIG. 13). Prior to attaining this steady state at 0.1 [$h^{-1}$], a pH disturbance was incurred, as shown in FIG. 14, and a pH excursion drift change experiment was undertaken as shown in FIG. 15. Samples were taken before each increase in dilution rate to select strains capable of utilizing organic acids efficiently.

Results:

A mixed culture of ~13 *Yarrowia lipolytica* strains (based on visual assessment of colony morphology) able to efficiently utilize butyrate and valerate as sole carbon source has been isolated from the original 72 strains.

Strains unable to catabolize butyrate and valerate efficiently were washed out of the chemostat fermenter owed to an uncompetitive growth rate. Table 5 shows the instantaneous consumption rates of butyric, valeric, succinic and glutaric acid.

TABLE 5

| Component | Consumption rate [μmol/((g DCW) · h)] |
| --- | --- |
| Butyric acid | 162 |
| Valeric acid | 440 |
| Succinic acid | 7.3 |
| Glutaric acid | −5.1 |

As shown in FIG. 14, the dissolve oxygen (DO) concentration, as an indicator of oxygen uptake rate at fixed oxygen transfer rate, increases sharply from ~35% saturation to ~70% saturation as the pH increases from 7.0 to 8.0. Given that oxygen consumption is an indicator of growth rate and thus carbon source consumption in an obligate aerobe, such as *Yarrowia lipolytica*, cultivation at pH>8.0 is not feasible using NVR carbon species as sole carbon and energy source.

As shown in FIG. 15, the dissolve oxygen (DO) concentration, as an indicator of oxygen uptake rate at fixed oxygen transfer rate, increases sharply from ~20% sat. to 90% sat. as the pH decreases from 7.0 to 5.0. Given that oxygen consumption is an indicator of growth rate and thus carbon source consumption in an obligate aerobe, such as *Yarrowia lipolytica*, cultivation at pH<5.0 is not feasible using NVR carbon species as sole carbon and energy source.

Despite the broad growth pH range of *Yarrowia lipolytica* of 2.0<pH<9.0 (Gonzalez-Lopez, C.I. (2002), Genetic control of extracellular protease synthesis in the yeast *Yarrowia lipolytica*. Genetics, 160: 417-427), the growth rate on the prevalent carbon sources in NVR is significantly inhibited at pH>8.0 and pH<5.0.

The consumption of the C4 and C5 monoacids was excellent, while the diacids were utilized much less efficiently and accumulated in the broth. HPLC quantification of the broth components clearly indicated that a portion of butyric acid and valeric acid was utilized for growth, while the rest was transformed via the endogenous ω-oxidation pathway to the diacids, succinic acid and buturic acid. See, Table 5. Therefore, host cell microorganisms, such as *Yarrowia lipolytica*, can be used to consume less desirable components, e.g., C4 and C5 monoacids, of a mixed organic waste stream.

Example 3

Chemo-Stat Fermentation with Cell Retention Using NVR as Carbon and Energy Source for *Yarrowia lipolytica*

Figure 16:
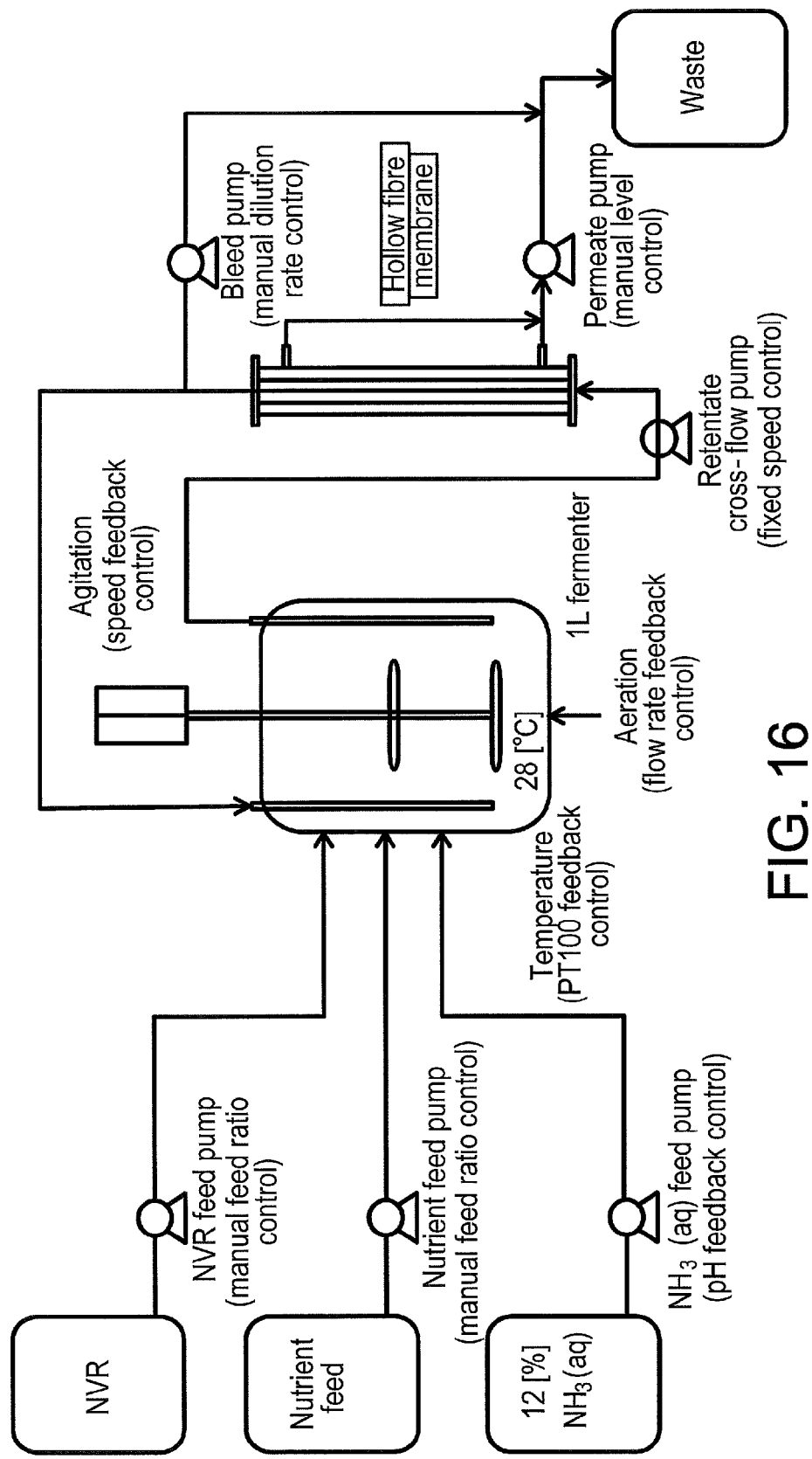
FIG. 16 shows the chemo-stat with cell retention experimental set-up used to study cell retention of *Y. lipolytica* grown in NVR as a carbon and energy source.

A chemo-stat fermentation with cell retention was set up, as shown in FIG. 16, with a 1 L jacketed glass fermenter and a 225 [cm$^2$] polyethersulfone 0.2 [μm] hollow fibre membrane. The experimental set-up provided for a NVR Feed, Nutrient Feed and Base Feed (12 [%] (v/v) NH$_3$(aq)) that was filter sterilized into the fermenter via peristaltic pumps. Furthermore, a peristaltic pump provided the necessary cross-flow retentate flow rate to the hollow fibre membrane, a peristaltic pump allowed withdrawal of permeate and a peristaltic pump allowed for a biomass bleed from the fermenter.

The chemo-stat's control philosophy entailed manual feed ratio control of the NVR Feed to Nutrient Feed rates, pH control via the Base Feed, temperature control via cooling water supply to the fermenter's jacket, fixed aeration & agitation rates via the respective feedback loops, fixed cross-flow rate via the retentate pump's variable speed drive, manual level control via the permeate pump and manual dilution rate control via the bleed pump.

The initial charge minimal media was prepared (6.7 g/L yeast base without amino acids+(NH$_4$)$_2$SO$_4$, 15 g/L glucose, 75 mg/L citric acid (Mr=210 g/mol), 5.8 g/L sodium citrate (Mr=294.1 g/mol), 10.7 g/L K$_2$HPO$_4$ (Mr=174 g/mol), 5.2 g/L KH$_2$PO$_4$ (M=136.1 g/mol), and 2 mL/L antifoam) and the Nutrient Feed was prepared (6.7 g/L yeast base without amino acids+(NH$_4$)$_2$SO$_4$, 75 mg/L citric acid (Mr=210 g/mol), 5.8 g/L sodium citrate (Mr=294.1 g/mol), 10.7 g/L K$_2$HPO$_4$ (Mr=174 g/mol), 5.2 g/L KH$_2$PO$_4$ (M=136.1 g/mol), and 2 mL/L antifoam). The control parameters for the fermenter were set up (A1 and A2: 1 vvm aeration, pH 7.0, DO calibration at pH 7.0 and 1 vvm to 100% saturation, 28° C., 750 rpm initial agitation until glucose depletion, 1250 rpm final agitation after glucose depletion, manual antifoam).

The fermenter was inoculated with a 10% (v/v) inoculum from a wild-type *Yarrowia lipolytica* shake flask that was grown overnight from a cryopreserved stock. The batch exponential growth phase commenced for approximately 8 hours until glucose depletion.

Figure 17:
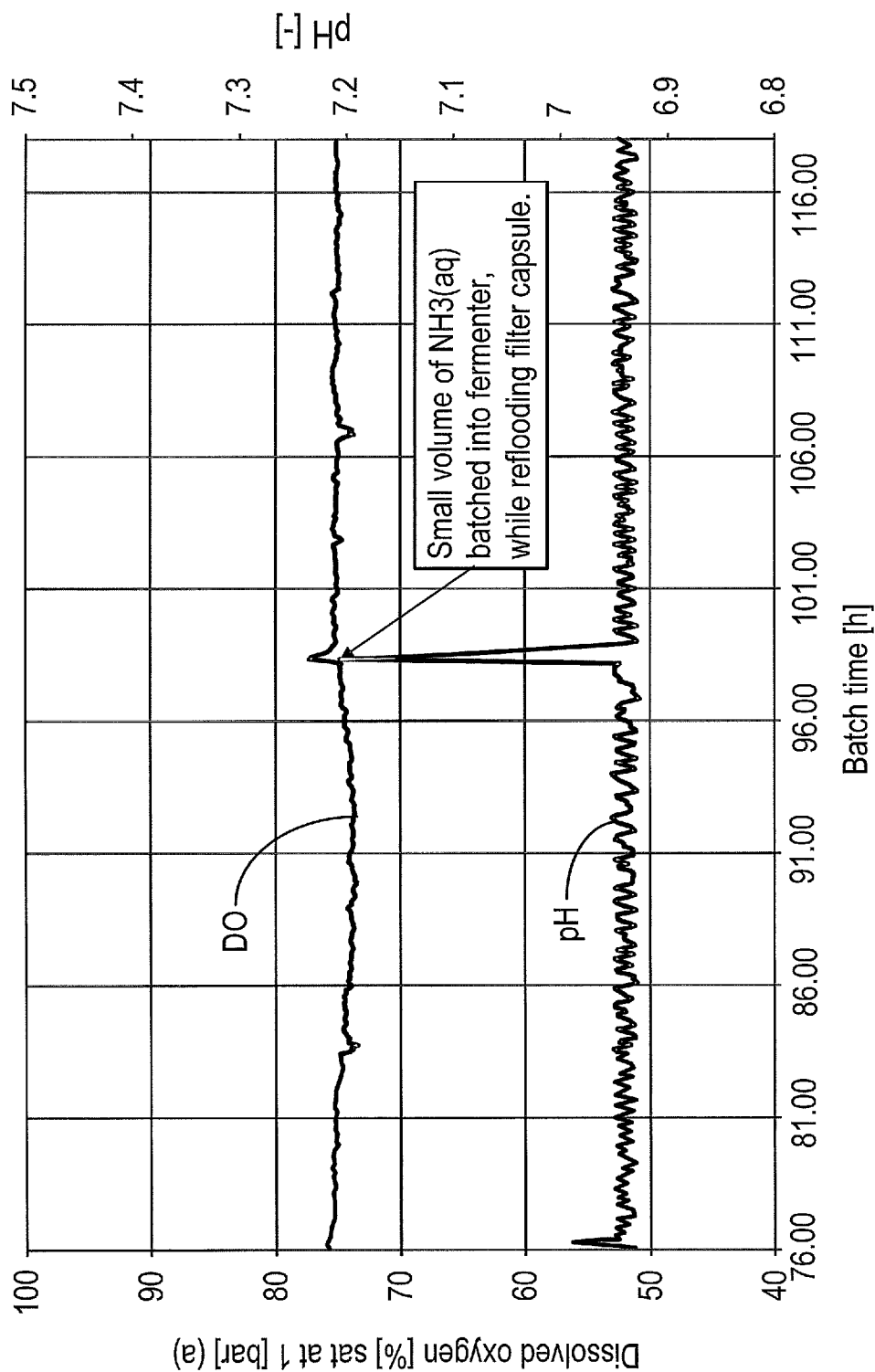
FIG. 17 shows the steady state chemostat cultivation with cell retention using 2 [%] (v/v) NVR at a flow rate of ~215 [mL/h] and an effective biomass dilution rate of 0.025 [h$^{-1}$].

After glucose depletion, a steady state was attained with an effective 2% (v/v) NVR feed at a Nutrient Feed flow rate of ~215 [mL/h] and an effective biomass dilution rate of ~0.025 μl, as shown in FIG. 17.

The NVR carbon species identified in the NVR Feed and permeate samples via HPLC retention times were γ-butyrolactone, butyric acid, succinic acid, δ-valerolactone, valeric acid, 5-hydroxyvaleric acid, glutaric acid, caproic acid, 6-hydroxycaproic acid and adipic acid.

Table 6 summarizes the NVR species with net catabolism or biosynthesis by wild-type *Yarrowia lipolytica*. In particular, catabolism of C4, C5, and C6 monoacids was observed by *Yarrowia lipolytica* during steady state chemo-stat cultivation with cell retention using 2% (v/v) NVR at a flow rate of ~215 [mL/h] and an effective biomass dilution rate of ~0.025 [h$^{-1}$].

TABLE 6

| NVR species | Synthesis (S), Catabolism (C) & Non-metabolized (NM) | Flux [% of valerate uptake] |
| --- | --- | --- |
| γ-butyrolactone | NM | 0 |
| butyric acid | C | 7 |
| succinic acid | S | 17 |
| δ-valerolactone | NM | 0 |
| valeric acid | C | 100 |
| 5-hydroxyvaleric acid | S | 32 |
| glutaric acid | S | 12 |
| caproic acid | C | 42 |
| 6-hydroxycaproic acid | S | 18 |
| adipic acid | C | 18 |

From Table 6, it can be seen that a net synthesis of succinic acid and glutaric acid was achieved at steady state, showing that a portion of the linear C4-C6 species were oxidized to the corresponding dicarboxylic acids by the wild-type *Yarrowia lipolytica* culture.

It can also been seen from Table 6 that a net synthesis of 5-hydroxyvaleric acid and 6-hydroxycaproic acid demonstrates carbon overflow into ω-oxidation, indicative of a saturated β-oxidation pathway. Therefore, the catabolism of C4-C6 NVR species is attenuated in the wild-type *Yarrowia lipolytica* culture.

Moreover, Table 6 shows that a portion of the linear C4-C6 monocarboxylic acids were catabolized; notably butyric, valeric and caproic acid. Therefore, a portion of the C4-C6 NVR species was catabolized by the wild-type *Yarrowia lipolytica* culture.

It can also be seen in Table 6 that the catabolism of the C6 components, caproic and adipic acid have steady state fluxes at 42% and 18% of the catabolism of the C5 component valeric acid respectively. The lower steady state flux of butyric acid at 7% of the catabolism of valeric acid is a consequence of carbon source limiting conditions for butyric acid, given the low concentration in the NVR Feed. Therefore, caproic and adipic acid were catabolized at a lower rate than valeric acid by the wild-type *Yarrowia lipolytica* culture.

Finally, Table 6 shows that there was a net catabolism of caproic acid and a net synthesis of 6-hydroxycaproic acid indicative of ω-oxidation activity. Therefore, a portion of the caproic acid was oxidized to 6-hydroxycaproic acid by the wild-type *Yarrowia lipolytica* culture.

Table 7 shows enrichment of adipate and dicarboxylic acids on a mass basis during steady state chemo-stat cultivation with cell retention using 2% (v/v) NVR at a flow rate of ~215 [mL/h] and an effective biomass dilution rate of 0.025 $[h^{-1}]$.

TABLE 7

| Feed | Adipic acid purity on total identified NVR species by HPLC [%] (m/m) | Dicarboxylic acid purity on total identified NVR species by HPLC [%] (m/m) |
|---|---|---|
| NVR to fermentation | 8.1 | 12.6 |
| Steady state broth concentration between a batch time of 103-118 [h] | 5.7 | 15.1 |

It can be seen from Table 7 that the steady state broth purity of dicarboxylic acids on a identified NVR species basis increased relative to the dicarboxylic acid purity in NVR.

The steady state dissolved oxygen (DO) concentration <100 [%] of saturation at an effective NVR feed concentration of 2% (v/v) demonstrates maintenance of culture viability for effective NVR feed concentrations >1% (v/v). See, FIG. 17. The steady state dissolved oxygen (DO) concentration <100% at an effective biomass dilution rate of ~0.025 $[h^{-1}]$ demonstrates a measureable growth rate in effective NVR feed concentrations >1% (v/v).

This example demonstrates that wild-type *Yarrowia lipolytica* cultured in NVR is capable of oxidizing linear C4-C6 species to the corresponding dicarboxylic acids, and attenuating catabolism of C4-C6 NVR species. Moreover, wild-type *Yarrowia lipolytica* culture was able to selectively catabolize NVR components, as caproic and adipic acid were catabolized at a lower rate than valeric acid. Additionally, catabolism of caproic acid resulted in the production of useful intermediates, e.g., 6-hydroxycaproic acid.

Example 4

Identification of Valerolactone as an Inhibitory Compound in NVR

Thirteen *Y. lipolytica* strains were selected for their ability to consume butyric and valeric acid. The strains were cultivated in a chemo-stat on 2.5% (v/v) NVR as sole energy and carbon source in different conditions, including C-source limiting and pH stat. In each case, the culture failed to reach steady state and was washed out. All components known to be present in NVR, including heavy metals, were evaluated and tested for toxicity, but none explain the severe inhibitory effect observed during feed of NVR as sole carbon source. HPLC analysis of the components in the broth showed that an unknown compound accumulated in the broth and was not consumed at all.

Figure 18:
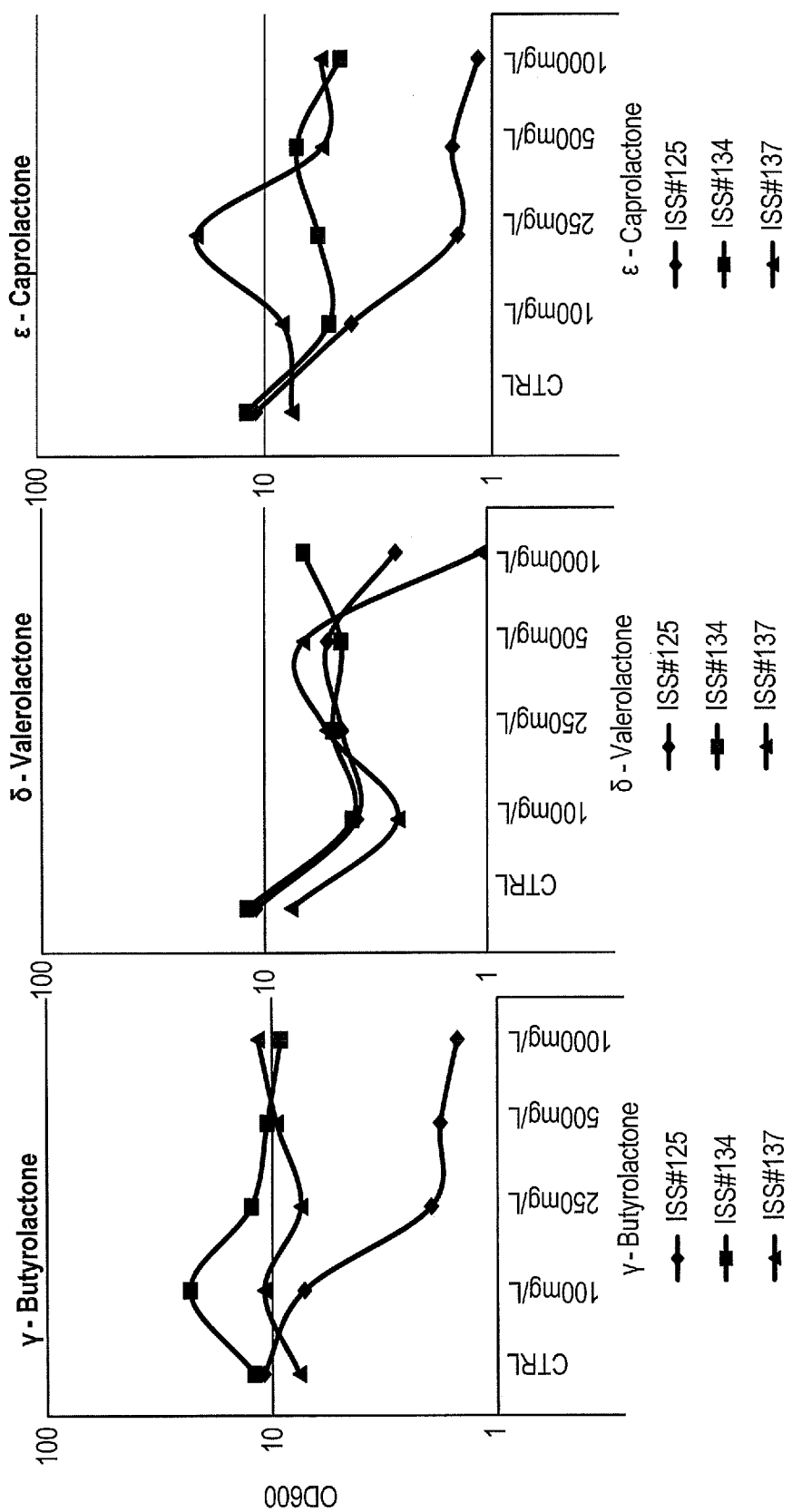
FIG. 18 shows growth of selected yeasts in the presence of 0.1-1 g/L lactones. Iss #125 is *S. cerevisiae* (control). Iss #134 is isolated from plates after slow growth on 3% (v/v) NVR+YPD media. Iss #137 is isolated from chemo-stat using synthetic NVR component feed.
Figure 19:
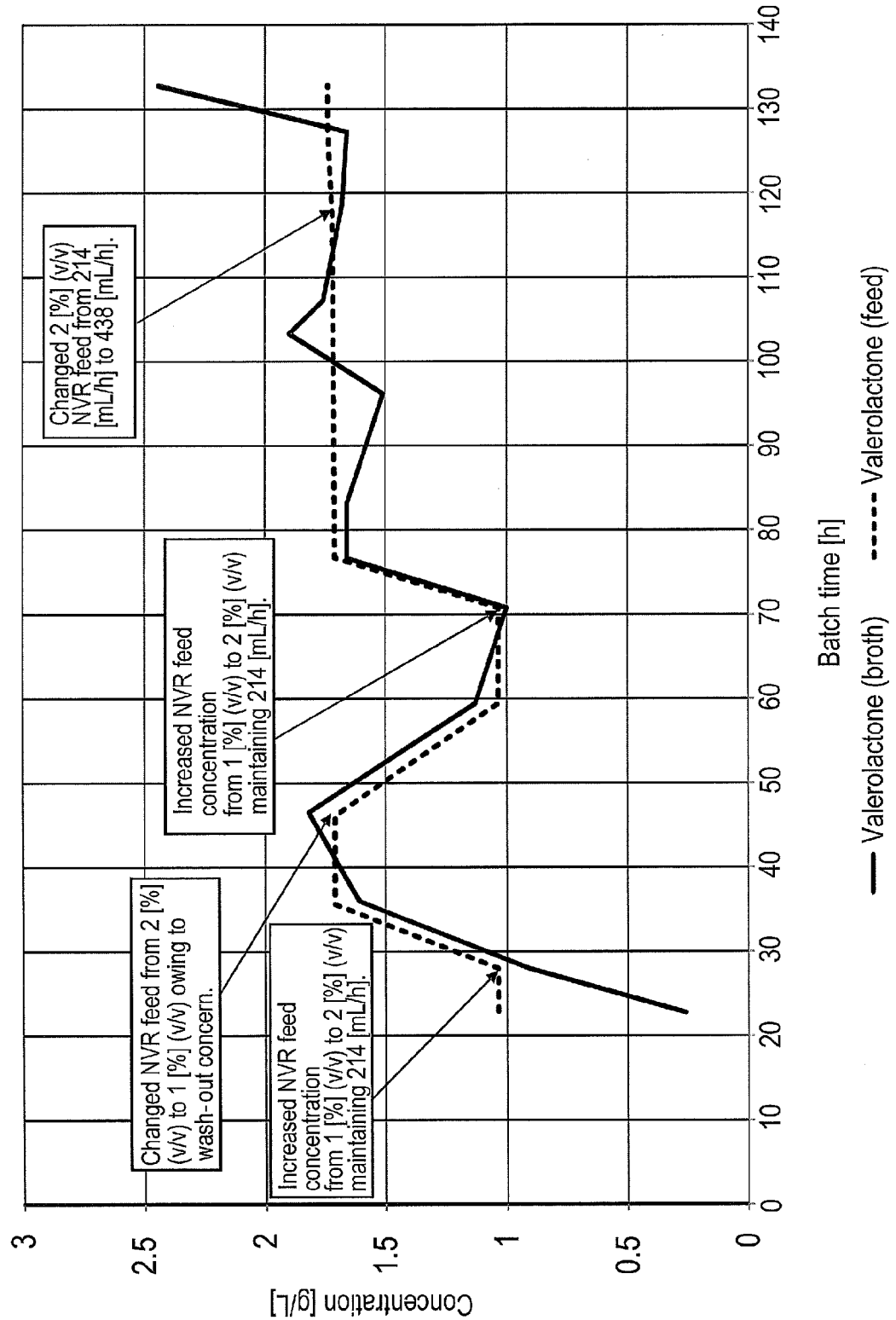
FIG. 19 shows an accumulation of valerolactone in a cell retention chemo-stat using 1-2% NVR as sole carbon source.

When *Y. lipolytica* strains previously adapted to NVR on agar plates containing 3% NVR were exposed to butyrolactone, valerolactone and caprolactone at concentrations between 0.1 and 1 g/L, it was found that valerolactone was inhibitory, especially to the strain selected by chemostat culture for growth on C4 and C5 acids (FIG. 18). A cell retention chemo-stat was required to avoid cell wash-out. In one such cell retention chemo-stat, at a 2% (v/v) effective NVR feed, valerolactone accumulates to ca. 1.7 g/L in the broth (FIG. 19), which from the inhibitory studies will completely inhibit growth. HPLC analysis confirmed that NVR contains a high concentration (ca. 92 g/L) of valerolactone.

This example identified valerlactone as an important inhibitory compound present in NVR. The presence of valerolactone was confirmed to inhibit the growth of NVR-tolerant host cells.

Example 5

Figure 20:
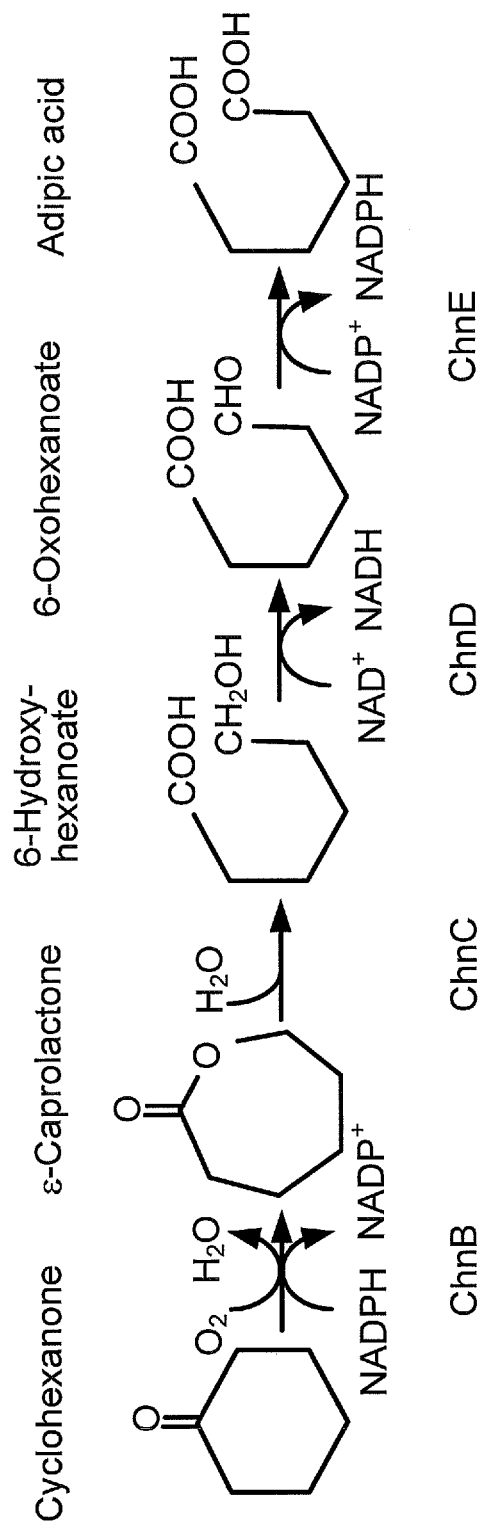
FIG. 20 shows the genes involved in oxidation of cyclohexanone to adipic acid including ChnC that catalyze the conversion of caprolactone to 6-hydroxycaproic acid. Several enzymes calssed as ChnC also catalyze the conversion of valerolactone to 5-hydroxyvaleric acid.

Lactone Hydrolases Remove Valerolactone from NVR by Converting it to 5-Hydroxyvaleric Acid, and Conversion of Cyclohexanol/Cyclohexanone in NVR to Adipic Acid The hydrolysis of lactones is catalyzed by the 1,4-lactonase class of enzymes (EC 3.1.1.25) and gluconolactonases (EC 3.1.1.17), which mediate the interconversion between the lactone and acid forms of hydroxy carboxylic acids. Microbial cells that are able to grow on cyclohexanol or cylcohexanone as sole carbon source, convert cyclohexanone to adipic acid via ε-caprolactone. The hydrolysis of ε-caprolactone to 6-hydroxyhexanoate is catalyzed by ChnC (FIG. 20).

Lactonases (ChnC) form organisms with a cyclohexanol degradation pathway are known to be able to convert 8-valerolactones to 5-hydroxyvaleric acid can be cloned and expressed as secreted enzymes in a host with a ω-oxidation pathway. This may allow the host, such as *Y. lipolytica*, to detoxify NVR by converting 8-valerolactone to 5-hydroxyvaleric acid, and subsequently converting the formed 5-hydroxyvaleric acid to glutaric acid. See, Example 7 for general methods to express heterologous hydrolases in *Y. lipoytica* targeted for extracellular secretion.

Similarly, the gene cluster comprised of ChnB, ChnC, Chn D, and ChnE can be expressed in *Y. lipolytica* or other suitable host cells to convert the cyclohexanol/cyclohexanone present in NVR to adipic acid. Suitable sources of gene clusters for conversion of cyclohexanone to adipic acid, or Chn C to convert 8-valerolactones to 5-hydroxyvaleric acid include the following:

Acintobacter acetyl-hydrolase (ChnC) (GenBank Accession AAG10029.1, SEQ ID NO:1).

A gene cluster in *Acinetobacter* SE19, which utilizes cyclohexanol as a sole carbon source, contains 13 open reading frames, including ChnC which is responsible for the hydrolysis step (FIG. 1, Cheng Q, Thomas S M, Kostichka K, Valentine J R, Nagarajan V (2000). Genetic analysis of a gene cluster for cyclohexanol oxidation in *Acinetobacter* sp. Strain SE19 by in vitro transposition. Journal of Bacteriology. 182: 4744-4751). Upon mutation in *Acinetobacter*, the accumulation of caprolactone demonstrated that chnC encodes caprolactone hydrolase. Onakunle et al (1997) report this lactonase as having strong specificity towards, ε-caprolactone, with some activity towards δ-lactones. (Onakunle O A, Knowles C S, Bunch A W. (1997). The formation and substrate specificity of bacterial lactonases capable of enantioselective resolution of racemic lactones. Enzyme and Microbial Technology. 21: 245-251).

*Brevibacterium epidermidis* HCU Lactonohydrolase (ChnC2) (GenBank Accession AAK73167.2, SEQ ID NO:2).

*Brevibacterium epidermidis* HCU are able to grow on cyclohexanol and are proposed to contain two different ε-caprolactone hydrolases (Brzostowicz P C, Blasko M S, Rouviere PE (2002). Identification of two gene clusters involved in cyclohexanone oxidation in *Brevibacterium epidermidis* strain HCU. Applied and Microbiological Biotechnology. 58:781-789). These share only 21% identity with one another, the Cluster 1 gene is most closely related to the *Rhodococcus caprolactonases* (below). The gene from Cluster 2 shares closest homology with 5-valerolactonases, including that from *Comomonas* sp. NCIMB 9872 and this lactone hydrolase was isolated from bacteria capable of growing on 0.1% cyclopentanol as its sole carbon source (Ishikawa T, Nishikawa H, Gao Y, Sawa Y, Shibata H, Yabuta Y, Maruta T, Shigeoka S (2008). The pathway via D-galacturonate/L-galactonate is significant for ascorbate biosynthesis in *Euglena gracilis*: identification and functional characterization of aldonolactonase. Journal of Biological Chemistry. 283: 31133-31141) and has a strong preference for δ-valerolactone (10× greater than for ε-caprolactone), as reported by Onakunle et al. (Onakunle O A, Knowles C J, Bunch A W (1997) The formation and substrate specificity of bacterial lactonases capable of enantioselective resolution of racemic lactones. Enzyme and Microbial Technology. 21: 245-251). The gene from Cluster 1 is closer to the caprolactone hydrolases.

*Rhodococcus* sp. Phi2 Caprolactone Hydrolase (ChnC) (GenBank Accession AAN37290.1, SEQ ID NO:3).

Brzostowicz et al., (2003) identified a partial gene cluster in *Rhodococcus* sp. Phi2 from a microbial community enriched for growth on cyclohexanone in a wastewater bioreactor. (Brzostowicz P C, Walters D M, Thomas S M, Nagarajan V, Rouvie're P E (2003) mRNA differential display in a microbial enrichment culture: simultaneous identification of three cyclohexanonemonooxygenases from three species. Applied and Environmental Microbiology. 69: 334-342). The cluster contains the four genes required for oxidation of cyclohexanone to adipic acid and the caprolactone hydrolase is closely related to the equivalent protein in *Arthrobacter* sp BO2, which was also identified in the same study. Bennett et al purified a caprolactone hydrolase from *Nocardia globerula* CL 1 which was induced in the presence of cyclohexanol. (Bennett A P, Strang E J, Trudgill P W, Wong V K (1988). Purification and properties of ε-caprolactone hydrolases from *Acinetobacter* NCIB 9871 and *Nocardia globevula* CU. Journal of General Microbiology. 134: 161-168). This protein exhibited maximum activity against ε-caprolactone and δ-valerolactone (40% activity relative to that with ε-caprolactone). *Nocardia globerula* and *Rhodococcus* are both in the Nocardiaceae family.

*Euglena gracilis* Lactonase (GNL) (GenBank Accession BAF94304.1, SEQ ID NO:4).

Ishikawa et al., (2008) report the activities of a purified aldonolactonase from the photosynthetic algae *Euglena gracilis* which hydrolyzes Glucono-δ-lactone, galactono-γ-lactone and glucono-γ-lactone.

The LIP2 gene encodes the main extracellular lipase activity of *Y. lipolytica* (Pignede G, Wang H, Fudalej F, Gaillardin C, Seman M, Nicaud J M (2000). Characterization of an extracellular lipase encoded by LIP2 in *Yarrowia lipolytica*. Journal of Bacteriology. 182: 2802-2810) and its cDNA sequence encodes a pre-pro enzyme containing a 13 amino acid signal sequence, a stretch of four dipeptides (X-Ala or X-Pro) that are substrates of a diaminopeptidase and a 12 amino acid pro-region containing a KR (Lys-Arg) site, substrate for the Xprendoprotease (FickersP, Marty A, Nicaud J M (2011). The lipases from *Yarrowia lipolytica*: Genetics, production, regulation, biochemical characterization and biotechnological applications. Biotechnology Advances 29: 632-644). At the early stage of growth the extracellular lipase is mainly associated with the cell wall before being released in the culture broth at the end of the growth phase (FickersP, Nicaud J M, Gaillardin C, Destain J, Thonart P (2004). Carbon and nitrogen sources modulate lipase production in the yeast *Yarrowia lipolytica*. Journal of Applied Microbiology 96:742-9). Consequently, the signal sequence of LIP2 is suitable for fusion with other 1 proteins to enable secretion.

Based on reports in the art that lactonases convert δ-valerolactones to 5-hydroxyvaleric acid, lactonases can be cloned and expressed as secreted enzymes in a host cell that also contains an ω-oxidation pathway to mediate removal of valerolactone from NVR via conversion to 5-hydroxyvaleric acid. Additionally, based on reports in the literature that microbial genes, e.g., ChnB, ChnC, Chn D, and ChnE, are responsible for utilization of cyclohexanol or cylcohexanone as a sole carbon source, these genes can be cloned and expressed in another host cell, e.g., *Y. lipolytica*, to convert cyclohexanone to adipic acid via ε-caprolactone.

Therefore, a lactonase, e.g., ChnC, may be expressed in a host, cell such as Y lipolytica, to remove the growth inhibition components from NVR by converting δ-valerolactone to 5-hydroxyvaleric acid, which can be subsequently converted to glutaric acid via the ω-oxidation pathway. In such a manner, a host cell may modify the properties of the mixed organic waste stream such that the waste stream is suitable for growth of the microorganism.

Example 6

Conversion of Caproic Acid and Hydroxycaproic Acid to Adipic Acid by *Y. lipolytica* and Accumulation of Adipic Acid in Strains with PDX Genes Encoding Acyl-CoA Oxidase Disrupted

*Yarrowia lipolytica* wild type (W29 or Pold (Mata ura3-302-270, xpr2-322, Ura⁻, Leu)) and mutant strains with various PDX gene deletions (Table below) were pre-cultured in YPD (3 ml) for 16 hours and used to inoculate shake flasks containing 10% production media (Y1T2D102, pH6.8-see general methods) to a final $OD_{600}$ of 0.05.

TABLE 8

Yeast strains used in this study
Yeast Strains and Phenotypes

JMY339, W29 (Mata, wild-type)
Pold (Mata ura3-302 leu2-270 xpr2-322, Leu⁻Ura⁻)
JMY117, MTLY24 (Mata ura3-302, xpr2-322, Δpox5)
JMY1283, MTLY32 (Mata ura3-302, xpr2-322 Δpox2 Δpox5)
JMY1284, MTLY36 (Mata ura3-302, xpr2-322 Δpox2 pox3 Δpox5)
MTLY40 (Mata ura3-302, xpr2-322 Δpox2Δpox3Δpox4Δpox5)
MTLY92 (Mata ura3-302, xpr2-322, TABLE 8-continued Yeast strains used in this study
Yeast Strains and Phenotypes ΔleuΔpox1Δpox2Δpox3Δpox4Δpox5pox6::hph)
JMY1233, MTLY95a (Mata ura3-302, xpr2-322, Δleu2Δpox1-6)
Candida maltosa (class 1, optional)

Strains were cultivated for 48 hours, harvested by centrifugation and resuspended to 200 mg/ml in phosphate buffer (50 mM. pH 7.0 containing glucose (10 mM), glucose-6-phosphate (6.7 mM), 0.4 U Glc6P dehydrogenase and NADPH (5 mM). Reactions were started by the addition of NVR (4%) and stopped after 24 hours by addition of 100 ul 6M $H_2SO_4$ and supernatants analysed by LC-MS.

Figure 21:
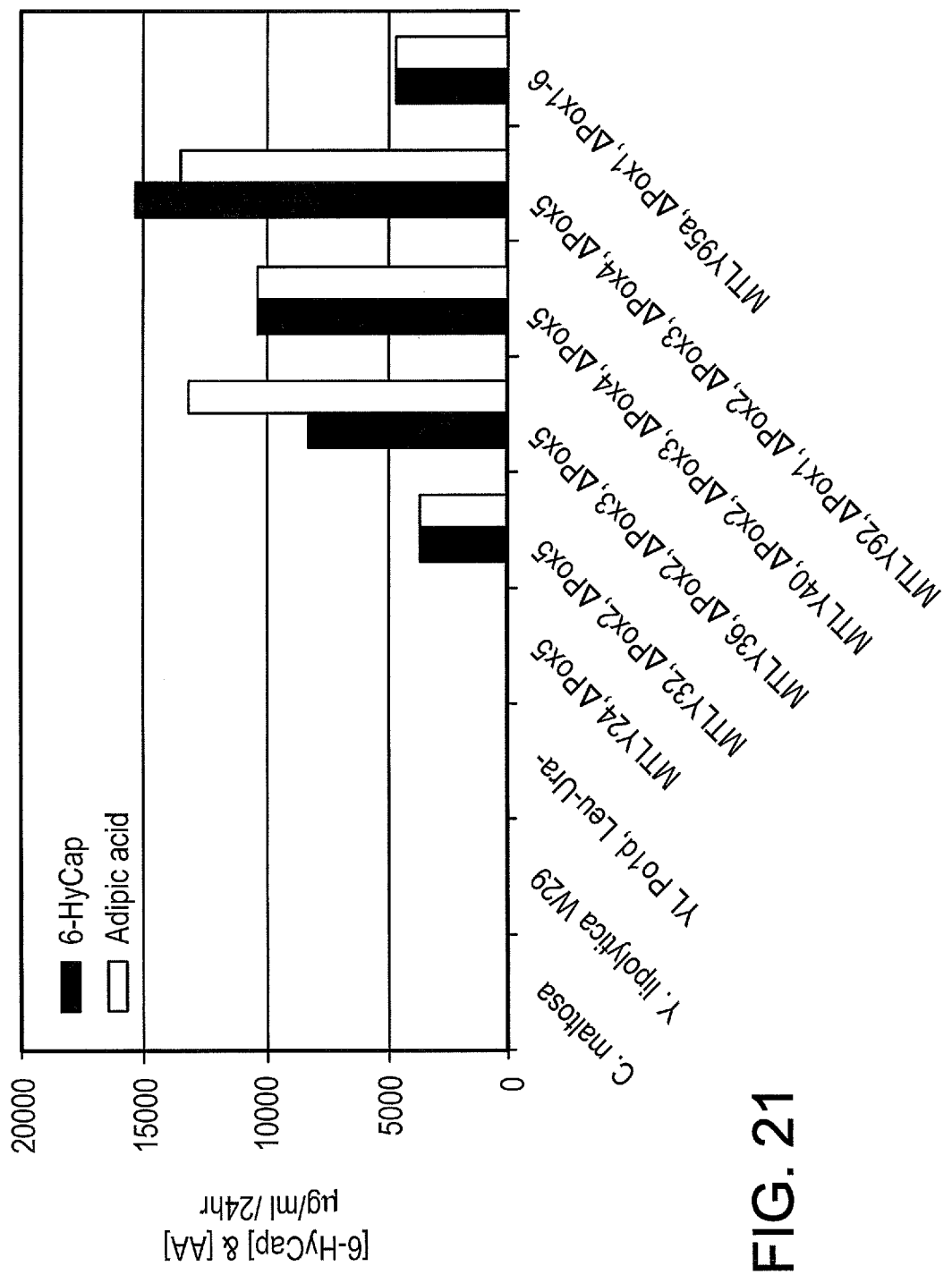
FIG. 21 illustrates that 6-hydroxycaproic acid and adipic acid accumulate in reaction supernatants of *Y. lipolytica* strains with impaired β-oxidation (various PDX mutants when incubated with NVR (4%), while no accumulation is observed in parent and wild type strains. Deletion of PDX genes encoding acyl-CoA oxidases thus prevents degradation of both adipic acid and 6-hydroxycaproic acid in NVR through β-oxidation.
Figure 22:
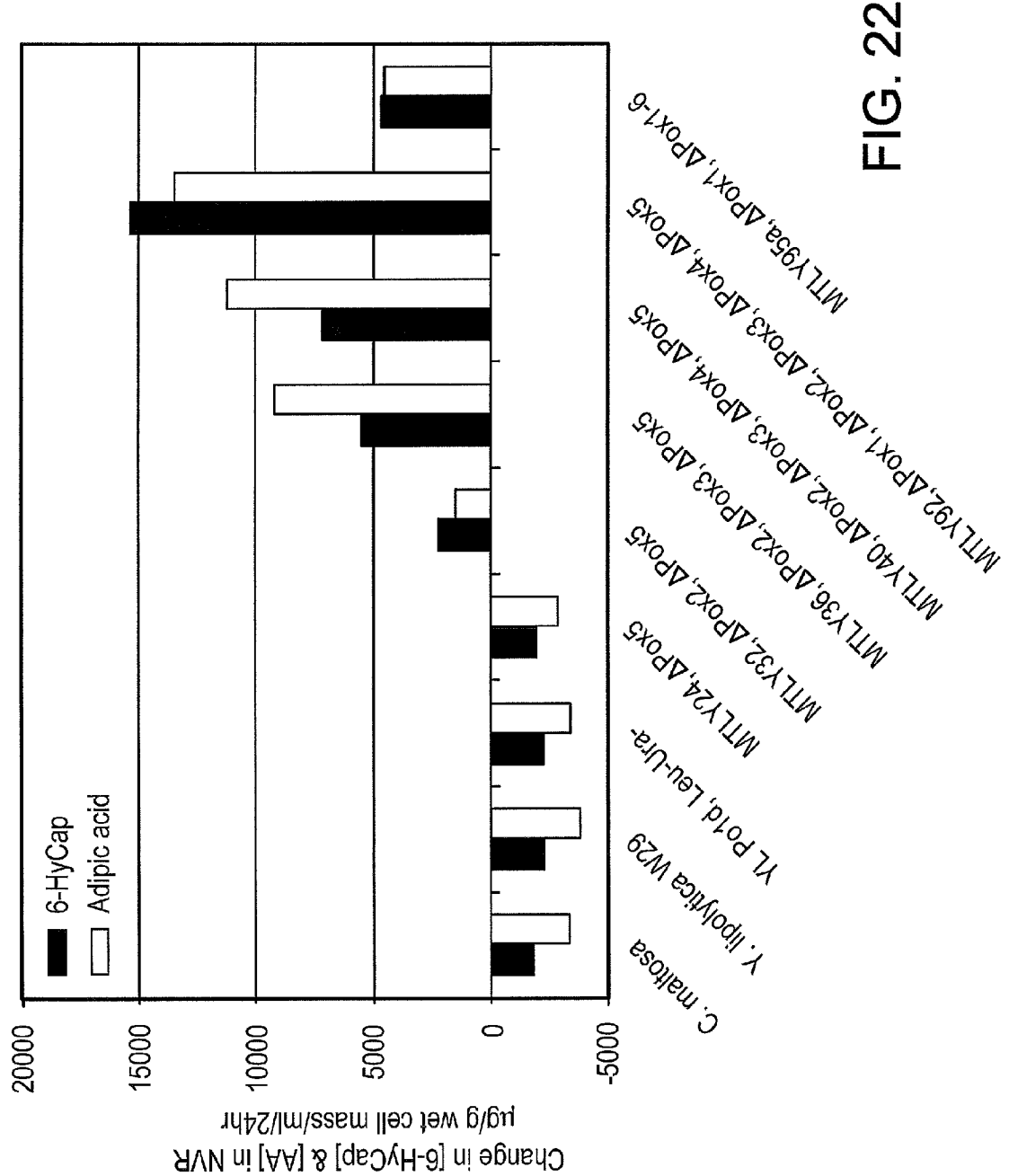
FIG. 22 illustrates that 6-hydroxycaproic acid and adipic acid in NVR are degraded by parent and wild type strains, while PDX mutants accumulate both acids. PDX 3 has the greatest effect on the degradation of C6 components.

The results clearly show that 6-hydroxycaproic acid and adipic acid accumulate in reaction supernatants of strains with impaired β-oxidation (PDX mutants) while no accumulation is observed in parent and wildtype strains. Deletion of PDX genes thus prevents degradation of both adipic acid and 6-hydroxycaproic acid in NVR through β-oxidation, as depicted in FIG. 1, and illustrated in FIGS. 21 and 22. Catabolism of 6-hydroxycaproic acid and adipic acid by parent and wildtype strains can thus be prevented by identifying the PDX genes involved in catabolism of C6 components in NVR via β-oxidation and deleting those PDX genes in the host strain. In *Yarrowia lipolytica*, PDX3 has the greatest effect on C6 components.

Example 7

General Methods for Cloning of Genes and Expression of Enzymes Targeted for Extracellular Secretion in *Y. lipolytica*

The LIP2 gene encodes the main extracellular lipase activity of *Y. lipolytica* (Pignede G, Wang H, Fudalej F, Gaillardin C, Seman M, Nicaud J M (2000). Characterization of an extracellular lipase encoded by LIP2 in *Yarrowia lipolytica*. Journal of Bacteriology. 182: 2802-2810) and its cDNA sequence encodes a pre-pro enzyme containing a 13 amino acid signal sequence, a stretch of four dipeptides (X-Ala or X-Pro) that are substrates of a diaminopeptidase and a 12 amino acid pro-region containing a KR (Lys-Arg) site, substrate for the Xprendoprotease (FickersP, Marty A, Nicaud J M (2011). The lipases from *Yarrowia lipolytica*: Genetics, production, regulation, biochemical characterization and biotechnological applications. Biotechnology Advances 29: 632-644). At the early stage of growth the extracellular lipase is mainly associated with the cell wall before being released in the culture broth at the end of the growth phase (Fickers P, Nicaud J M, Gaillardin C, Destain J, Thonart P (2004). Carbon and nitrogen sources modulate lipase production in the yeast *Yarrowia lipolytica*. Journal of Applied Microbiology 96:742-9). Consequently, the signal sequence of LIP2 is suitable for fusion with other proteins to enable secretion.

Standard molecular techniques were applied, according to Sambrook et al., (Molecular Cloning—a Laboratory Manual, Cold Spring Harbor Laboratory Press, 1989). Target DNA sequences encoding for the respective hydrolases (esterases, lipases, cutinases, lactonases) were first codon-optimized, according to the frequency of codon usage in the expression host *Yarrowia lipolytica*. Subsequently, the codon-optimized hydrolase gene sequences were designed to fuse/replace their original signal peptide sequences with *Yarrowia lipolytica* lipase 2 (Lip2) prePro DNA sequence at the 5' arm side for efficient protein expression, secretion, and procession. A BamHI site together with a consensus sequence (CACA) at the translation initiation site, and an AvrII site plus two stop codons were also engineered at both the 5' arm and the 3' arm sides respectively, to facilitate cloning the target genes into the yeast expression vectors (Gasmi et al., (2011) Appl Microbiol Biotechnol 89:109-119). All the hydrolase genes were synthesized, and finally cloned in the pEX-A vector (pEX-A Hydrolases) by Eurofins MWG operon (Germany).

Figure 3:
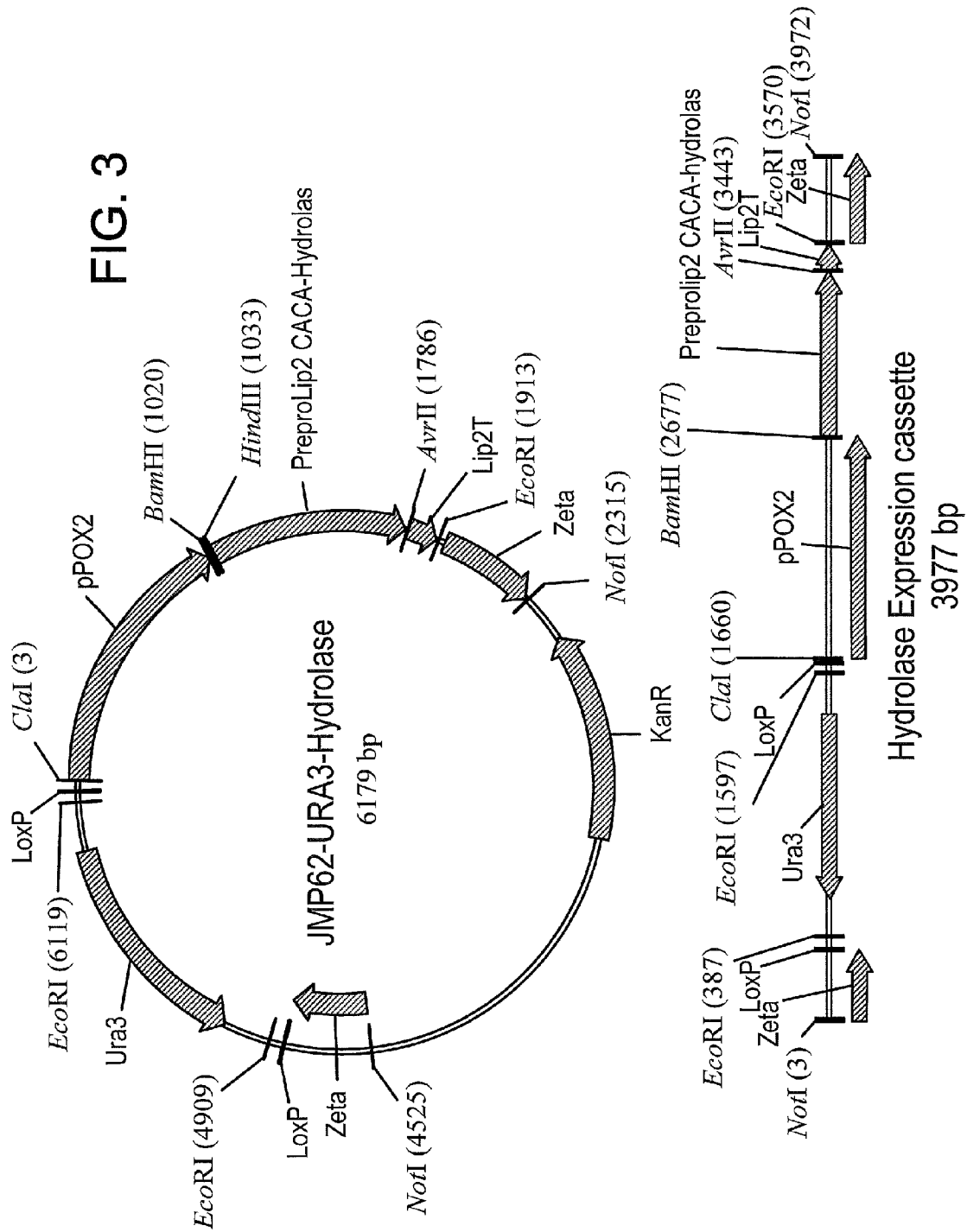
FIG. 3 is a schematic diagram of the expression vector construct used for expression of enzymes targeted for extracellular secretion in the host strain *Yarrowia lipolytica*.

The fragments carrying the prePro Lip2_Hydrolases (esterases, lipases, cutinase, or lactonase) were rescued from the pEX-A_Hydrolases plasmids with BamHI/AvrII restriction enzymes, purified and subcloned into the *Yarrowia lipolytica* expression vector, JMP62 URAex (JME 803), which contains a strong inducible Pox promoter, a Lip2 gene terminator, a Ura3 selectable marker, as well as Zeta-docking sequences for random chromosomal integration (see FIG. 3 for a schematic plasmid map of the JMP62-hydrolase expression vectors and of the hydrolase expression cassettes).

The expression vectors with target hydrolases were digested with the restriction enzyme, NotI, and subjected to electrophoresis. The expression cassettes were extracted from the gel and used for transformation of *Yarrowia lipolytica*.

A lipase deficient strain of *Yarrowia lipolytica*, JMY1212 (MATA ura3-302 leu2-270-LEU2-zeta xpr2-322 Δlip2Δlip7Δlip8, Leu⁺, Ura⁻), was transformed using lithium acetate method as described by Le Dall et al., 1994 (Multiple-copy integration in the yeast *Yarrowia lipolytica*. Current Genetics 26:38-44). *Yarrowia lipolytica* transformants were obtained upon selection for Ura+ on YNB medium plates. Independent colonies were selected from each transformed strain with respective hydrolase.

Yeast strains were grown in rich medium YPD (10 g/l yeast extract, 10 g/l bactopeptone, 10 g/l glucose) or in Y1T2D1O$_2$ medium (1% yeast extract, 2% tryptone, 1% glucose, 2% oleic acid, and 50 mM sodium phosphate buffer, pH 6.8) for inducible expression. Protein expression and enzymatic hydrolytic activity towards oligomeric esters were determined with modified method, as described by ((Pignede et 42000 Appl. Environ. Microbiol. 66:3283-3289).

Accordingly, using these standard cloning techniques, *Y. lipolytica* can be modified to express and secrete enzymes that catabolize oligomeric ester components of mixed organic waste streams into monomers, and further enzymatically process the monomer components into desirable compounds.

Example 8

Conversion of Components in NVR to α,ω-Difunctional C6 Alkanes

FIG. 2 shows the enzymatic conversion of 6-hydroxycaproic acid to 1,6-hexanediol, adipic acid to 6-oxohexanoic acid, and 6-oxohexanoic acid to 6-aminocaproic acid. 6-aminocaproic acid in turn can be converted to hexamethylenediamine or caprolactam.

Conversion of 6-oxohexanoic acid to 6-aminocaproic acid (reaction 1 in FIG. 2) catalyzed by beta-alanine-aminotransferases (EC 2.6.1.19) has been documented (.Enzymatic studies on the metabolism of beta-alanine (Hayaishi et al.,. 1961 J. Biol. Chem. 236, p. 781-790) and further examples of 1-aminotransferases are disclosed in WO2009/113855 (The preparation of 6-aminocaproic acid from 5-formyl valeric acid) and WO2011-031147 (Preparation of a compound comprising an amine group from an alpha-keto acid). Enzymes that are suitable to catalyze the conversion of adipic acid to 6-oxohexanoic acid (reaction 2 in FIG. 2) include carboxylate reductases (EC 1.2.99.6) or aldehyde dehydrogenase (EC 1.2.1.3 and EC 1.2.1.31). Enzymes that are suitable to catalyze the conversion of 6-oxohexanoic acid to 6-hydroxyhexanoic acid include 6-hydroxyhexanoate dehydrogenase (EC 1.1.1.258). Enzymes that are suitable to catalyze the conversion of 6-hydroxyhexanoic acid to 1,6-hexanediol (reaction 4 in FIG. 2) include bifunctional alcohol/aldehyde dehydrogenases (EC 1.2.1.10), while enzymes that are suitable to catalyze the conversion of 6-aminohexanoic acid to caprolactam (reaction 5 in FIG. 2) include amidohydrolase (EC 3.5.2.-), such as EC 3.5.2.11. Predicted enzymes suitable to catalyze conversions 2, 3, 4, and 5 in FIG. 2 have been disclosed (WO2009/151728: Microorganisms for the production of adipic acid and other compounds, WO2010/068944: Biological synthesis of difunctional alkanes from carbohydrate feedstocks).

All documents cited herein, including, but not limited to, patents, published patent applications, and non-patent literature, are incorporated by reference herein in their entirety.

The invention claimed is:

1. A method for enriching monomer content in a cycloalkane oxidation process mixed organic waste stream, comprising:
    (a) combining a biocatalyst with a mixed organic waste stream from a cycloalkane oxidation process, wherein the biocatalyst is esterase (EC 3.1.1.1), cutinase (EC 3.1.1.74), polyhydroxyalkanoate (PHA) depolymerase (EC 3.1.1.75 & EC 3.1.1.76), 1,4-lactonase (EC 3.1.1.25), or gluconolactonases (EC 3.1.1.17), or combinations thereof; and
    (b) enzymatically converting lactone, dimeric and/or oligomeric components of said mixed organic waste stream into monomeric components.

2. The method according to claim 1, further comprising treating said mixed organic waste stream with at least one hydrolase enzyme, a naturally or non-naturally occurring host cell which:
    a. hydrolyzes oligomeric esters into monomers, and
    b. increases the amount of monomer components.

3. The method according to claim 2, wherein treatment with the hydrolase reduces the viscosity of the mixed organic waste stream to improve the efficiency of burning the stream and/or prepare the stream for further chemical or biological treatment.

4. The method according to claim 3, further comprising burning the treated mixed organic waste stream for fuel value or to produce a syngas.

5. The method according to claim 3, further comprising performing an esterification to produce mixed esters or polyols, hydrogenation to produce diols, oxidation to produce diacids, reductive amination, sulfonation, or treating with NH$_4$OH or polyamines.

6. The method according to claim 2, wherein the hydrolyzing oligomeric esters into monomers is performed concurrently with additional separation, chemical conversion, or enzymatic conversion by a biocatalyst.

7. The method according to claim 1, further comprising:
    treating said mixed organic waste stream with a naturally or non-naturally occurring host cell which:
    a. hydrolyzes at least a portion of oligomeric esters into monomers;
    b. hydrolyzes at least a portion of lactones into hydroxy-acids; or
    c. oxidizes at least a portion of linear C4-C6 monoacids, hydroxy-acids and oxo-acids to the corresponding diacids, and
    increasing the amount of diacids.

8. The method according to claim 7, further comprising esterifying the diacids prior to separation into C4, C5, or C6 diacids.

9. The method according to claim 1, further comprising:
    treating said mixed organic waste stream with a non-naturally occurring host cell, which:
    a. hydrolyzes at least a portion of oligomeric esters into monomers;
    b. hydrolyzes at least a portion of ε-caprolactone to 6-hydroxy-caproic acid;
    c. oxidizes at least a portion of caproic acid, 6-hydroxycaproic acid and 6-oxocaproic acid to adipic acid;
    d. converts at least a portion of the cyclic C6 components to adipic acid;
    e. catabolizes at least a portion of C3, C4 and C5 components; or
    f. catabolizes C6 components at a lower rate than C3, C4 and C5 components, and increasing the concentration of adipic acid and reducing the amount of mono-acids and hydroxyacids.

10. The method according to claim 1, further comprising:
    treating said mixed organic waste stream with a non-naturally occurring host cell which:
    a. hydrolyzes at least a portion of oligomeric esters into monomers;
    b. oxidizes at least a portion of caproic acid to 6-hydroxycaproic acid;
    c. converts at least a portion of the cyclic C6 components to 6-hydroxycaproic acid or 6-oxocaproic acid;
    d. catabolizes at least a portion of C3, C4 and C5 components; or
    e. catabolizes C6 components at a lower rate than C3, C4 and C5 components; and expressing at least one biosynthetic pathway enzyme to convert adipic acid, 6-hydroxycaproic acid or 6-oxohexanoic acid to 1,6-hexanediol, 6-aminocaproic acid, ε-caprolactam or hexamethylenediamine, and
    converting C6 components and precursors present in said stream to α, ω-difunctional C6 alkanes.

11. The method according to claim 10, wherein the non-naturally occurring host cell which converts oligomeric esters, caproic acid, and cyclic C6 compounds to 6-hydroxycaproic acid, 6-oxohexanoic acid, and adipic acid also produces 1,6-hexanediol.

12. The method according to claim 11, where the non-naturally occurring host cell producing 1,6-hexanediol expresses an aldehyde dehydrogenase catalyzing the conversion of 6-oxohexanoic acid to 6-hydroxycaproic acid, and an alcohol dehydrogenase catalyzing the conversion of 6-hydroxycaproic acid to 1,6-hexanediol.

13. The method according to claim 10, wherein the non-naturally occurring host cell which converts oligomeric esters, caproic acid, and cyclic C6 compounds to 6-hydroxycaproic acid, 6-oxohexanoic acid, or adipic acid also produces 6-aminocaproic acid.

14. The method according to claim 13, where the non-naturally occurring host cell producing 6-aminocaproic acid expresses an aminotransferase which converts 6-oxohexanoic acid to 6-aminocaproic acid.

15. The method according to claim 14, where the non-naturally occurring host cell producing 6-aminocaproic acid also expresses an amidohydrolase which converts 6-aminocaproic acid to ε-caprolactam.

16. The method according to claim 14, where the non-naturally host cell producing 6-aminocaproic acid also produces hexamethylenediamine via an aldehyde dehydrogenase which converts 6-aminocaproic acid to 6-aminohexanal, and a 1-aminotransferase which converts 6-aminohexanal to hexamethylenediamine.

17. The method according to claim 1, wherein the mixed organic waste stream from a cycloalkane oxidation process further comprises a non-volatile residue (NVR), water wash, a concentrated water extract (COP acid), a caustic wash stream, or combinations thereof.

18. The method according to claim 1, further comprising adding an isolated enzyme or an enzyme secreted by a naturally occurring or non-naturally occurring host cell, and said enzyme is a P450 cytochrome oxidase, an w-hydroxylase, w-oxygenase enzyme or alkane-1-monooxygenase from the class EC 1.14.15.3; a fatty alcohol oxidase; an alcohol dehydrogenase from the class EC 1.1.1.-; a Baeyer-Villiger monooxygenase; a caprolactone lactonohydrolase; a fatty alcohol oxidase; an alcohol dehydrogenase; a cyclohexane-1,2-diol dehydrogenase; a cyclohexane-1,2-dione acylhydrolase; or a carboxylesterase from the α,β-hydrolase fold family (EC 3.1.1.-).

19. The method according to claim 1, further comprising adding an isolated enzyme or an enzyme secreted by a naturally occurring or non-naturally occurring host cell, wherein said enzyme is a cyclohexanol dehydrogenase/ChnA from the class EC 1.1.1.245; cyclohexanone monooxygenase/ChnB from the class EC 1.14.13.22; gluconolactonase/ChnC from the class EC 3.1.1.17; ChnD from the class EC 1.1.1.2; cyclohexane-1,2-diol dehydrogenase from EC 1.1.1.174; cyclohexane-1,2-dione acylhydrolase from EC 3.7.1.10 or EC 3.7.1.11; or combinations thereof.

20. The method according to claim 2, 7, 9, or 10, further comprising hydrolyzing of oligomeric esters into monomers by an isolated or immobilized hydrolase, or an endogenous or heterologous hydrolase secreted by a naturally or non-naturally occurring host cell during fermentation and bioconversion.

21. The method according to claim 2, 7, 9, or 10, further comprising catalyzing hydrolysis of oligomeric esters into monomers by a hydrolase that is active at acidic pH, a physiological pH, or an alkaline pH.

22. The method according to claim 7, 9 or 10, where the naturally or non-naturally occurring host cell that converts C4-C6 or C6 monoacids, hydroxy-acids and oxo-acids to diacids via the oxo-acid, has an endogenous or heterologous w-oxidation pathway which catalyzes one or more of the following conversions:
   a. conversion of butyric acid, valeric acid, and/or adipic acid to succinic acid, glutaric acid, and/or adipic acid;
   b. conversion of butyric acid, valeric acid, and/or adipic acid to 4-hydroxybutyric acid, 5-hydroxyvaleric acid, and/or 6-hydroxycaproic acid;
   c. conversion of 4-hydroxybutyric acid, 5-hydroxyvaleric acid, and/or 6-hydroxycaproic acid to 4-oxobutanoic acid, 5-oxopentanoic acid, and/or 6-oxohexanoic acid; or
   d. conversion of 4-oxobutanoic acid, 5-oxopentanoic acid, and/or 6-oxohexanoic acid to succinic acid, glutaric acid, and/or adipic acid.

23. The method according to claim 22, where the endogenous or heterologous ω-oxidation pathway converts aliphatic fatty acids to diacids via hydroxyl-acids and oxo-acids, and said naturally or non-naturally occurring host cell is an n-alkane utilizing yeast or bacterium.

24. The method according to claim 23, where the n-alkane utilizing yeast is Yarrowia lipolytica, Candida tropicalis, C. albicans, C. cloacae, C. guillermondii, C. intermedia, C. maltosa, C. parapsilosis, C. zeylenoides, or combinations thereof, or yeasts of the Rhodotorula, Rhizopus, Trichosporon, Debaryomyces and Lipomyces genera or combinations thereof; and wherein the n-alkane utilizing bacteria is Pseudomonas fluorescens, P. putida, P. aeroginosa, P. oleoverans, Marinobacter hydrocarbonoclasticus, Acinetobacter venetianus, Oleiphilus messinensis, Arthrobacter viscosus, Cupriavidus metallidurans, Rhodococcus erythropolis, Sphingomona spaucimobilis, Burkholderia cepacia, Delftia acidovorans, Alcanivorax diesolei or combinations thereof.

25. The method according to claim 9 or 10, wherein the naturally or non-naturally occurring host cell which converts at least a portion of the cyclic C6 components of the waste stream into 6-hydroxycaproic acid, 6-oxohexanoic acid or adipic acid has an endogenous or heterologous pathway which catalyzes one or more of the following conversions:
   I. cyclohexanol to 6-oxohexanoic acid, wherein one or more of the following conversions are catalyzed:
      a. conversion of cyclohexanol to cyclohexanone;
      b. conversion of cyclohexanone to ε-caprolactone;
      c. conversion of ε-caprolactone to 6-hydroxyhexanoic acid; or
      d. conversion of 6-hydroxyhexanoic acid to 6-oxohexanoic acid;
   II. 1,2-cyclohexanediol to 6-oxohexanoic acid, wherein one or more of the following conversions are catalyzed:
      a. conversion of cyclohexane-1,2-diol to cyclohexane-1,2-dione; or
      b. conversion of cyclohexane-1,2-dione to 6-oxohexanoic acid; and
   III. 6-oxohexanoic acid to adipic acid.

26. The method according to claim 2, 7, 9, or 10, wherein the naturally or non-naturally occurring host cell is tolerant to a non-volatile residue (NVR).

27. The method according to claim 2, 7, 9, or 10, wherein the naturally or the non-naturally occurring host cell is tolerant to at least 1% of the mixed organic waste stream from a cycloalkane oxidation process by volume.

28. The method according to claim 27, further comprising improving the tolerance of the host cell to the mixed organic waste stream by reducing the amount of inhibitory compounds in said mixed organic waste stream from a cycloalkane oxidation process.

29. The method according to claim 28, wherein the inhibitory compounds include lactones, and wherein the method further comprises reducing the amount of lactones in the mixed organic waste stream from a cycloalkane oxidation process by treating with one or more biocatalysts which hydrolyze the lactones to the corresponding hydroxyl-acids before or during treatment of the mixed organic waste stream with the naturally or non-naturally occurring host cell.

30. The method according to claim 29, wherein the biocatalyst which hydrolyze the lactones is an enzyme expressed by the naturally or non-naturally occurring host cell and secreted during fermentation.

31. The method according to claim 9 or 10, wherein the lower rate of catabolism of C6 compounds by the non-naturally occurring host cell provides a higher yield of C6 components from the mixed organic waste stream from a cycloalkane oxidation process.

32. The method according to claim 31, further comprising reducing the degradation of caproic acid, hydroxycaproic acid, and adipic acid to acetyl-CoA through β-oxidation by the non-naturally occurring host cell.

33. The method according to claim 32, wherein degradation of caproic acid, hydroxycaproic acid and adipic acid through β-oxidation is reduced by deleting or inhibiting one or more enzymes that use caproic acid, hydroxycaproic acid and adipic acid to generate CoA esters as a substrate.

34. The method according to claim 33, comprising reducing degradation of caproic acid, hydroxycaproic acid, and adipic acid through β-oxidation by deleting or inhibiting one or more enzymes that oxidize CoA esters.

35. The method according to claim 34, wherein the enzyme or enzymes is or are chosen from CoA ligases, CoA transferases, acyl-CoA oxidases, and acyl-CoA dehydrogenases.

36. The method according to claim 7, 9, or 10, further comprising crystallizing adipic acid.

37. The method according to claim 7, 9, or 10, wherein the natural or non-natural host cell utilizes carbon sources at pH 5.0-8.0.

38. The method according to claim 1, 2, 7, 9, 10, 17, 18, or 19, further comprising recovering or separating said monomeric components, diacids, adipic acids, or α,ω-difunctional C6 alkanes.

* * * * *